(12) United States Patent
Witola et al.

(10) Patent No.: US 12,396,969 B2
(45) Date of Patent: Aug. 26, 2025

(54) COMPOUNDS AND METHODS FOR THE TREATMENT OF PARASITIC INFECTIONS

(71) Applicant: THE BOARD OF TRUSTEES OF THE UNIVERSITY OF ILLINOIS, Urbana, IL (US)

(72) Inventors: William Harold Witola, Champaign, IL (US); Kun Li, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 864 days.

(21) Appl. No.: 17/616,771

(22) PCT Filed: Jun. 5, 2020

(86) PCT No.: PCT/US2020/036336
§ 371 (c)(1),
(2) Date: Dec. 6, 2021

(87) PCT Pub. No.: WO2020/247758
PCT Pub. Date: Dec. 10, 2020

(65) Prior Publication Data
US 2022/0313631 A1    Oct. 6, 2022

Related U.S. Application Data

(60) Provisional application No. 62/858,551, filed on Jun. 7, 2019.

(51) Int. Cl.
*C07C 50/24*    (2006.01)
*A61K 9/00*    (2006.01)
(Continued)

(52) U.S. Cl.
CPC .......... *A61K 31/167* (2013.01); *A61K 9/0014* (2013.01); *A61K 9/0019* (2013.01); *A61K 9/06* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/485* (2013.01); *A61K 9/4858* (2013.01); *A61K 9/4866* (2013.01); *A61K 31/095* (2013.01); *A61K 31/122* (2013.01); *A61K 31/136* (2013.01); *A61K 31/223* (2013.01); *A61K 47/02* (2013.01); *A61K 47/10* (2013.01); *A61K 47/14* (2013.01); *A61K 47/26* (2013.01); *A61K 47/44* (2013.01); *A61P 33/02* (2018.01); *C07C 50/24* (2013.01); *C07C 225/30* (2013.01); *C07C 225/34* (2013.01);
(Continued)

(58) Field of Classification Search
CPC .. A61K 31/167; A61K 31/095; A61K 31/122; A61K 31/136; A61K 31/223; A61K 47/02; A61K 47/10; A61K 47/14; A61K 47/26; A61K 47/44; A61K 9/0014; A61K 9/0019; A61K 9/06; A61K 9/2013; A61K 9/2018; A61K 9/2027; A61K 9/2054; A61K 9/2059; A61K 9/485; A61K 9/4858; A61K 9/4866; A61P 33/02; C07C 50/24; C07C 237/04; C07C 225/30; C07C 225/34; C07C 325/04; C07C 323/52; C07C 327/42; C07C 2602/10; C07C 2603/24; C07C 50/34

See application file for complete search history.

(56) References Cited

U.S. PATENT DOCUMENTS 2,494,031 A * 1/1950 Brooker ................ C09B 23/164
548/150
6,306,550 B1 * 10/2001 Itoh ........................ C09B 69/10
430/7
(Continued)

FOREIGN PATENT DOCUMENTS

DE      1219040    *  6/1966
DE      1263737    *  3/1968
(Continued)

OTHER PUBLICATIONS

Sossah et al., Genome Sequencing of Cladobotryum protrusum Provides Insights into the Evolution and Pathogenic Mechanisms of the Cobweb Disease Pathogen on Cultivated Mushroom, Genes, vol. 10, No. 2, 124, 18 pages (Year: 2019).*
(Continued)

*Primary Examiner* — Brenda L Coleman
(74) *Attorney, Agent, or Firm* — Haukaas Fortius PLLC; Michael Haukaas

(57) ABSTRACT

*Cryptosporidium parvum* is a highly prevalent zoonotic and anthroponotic protozoan parasite that causes a diarrheal syndrome in children and neonatal livestock, culminating in growth retardation and mortalities. Disclosed herein are inhibitors against the enzymatic activity of recombinant CpLDH protein that were identified. The inhibitors were tested for anti-*Cryptosporidium* effect using in vitro infection assays of HCT-8 cells monolayers. Compounds NSC158011 and NSC10447 were identified to inhibit the proliferation of intracellular *C. parvum* in vitro, with IC50 values of 14.88 and 72.65 μM, respectively. At doses tolerable in mice, both NSC158011 and NSC10447 significantly reduced the shedding of *C. parvum* oocysts in infected immunocompromised mice's feces and prevented intestinal villous atrophy as well as mucosal erosion due to *C. parvum*. These findings have unveiled anti-*Cryptosporidium* drug candidates that can be explored further for the development of therapeutic agents against *C. parvum* infections.

19 Claims, 14 Drawing Sheets

(51) Int. Cl.

| | |
|---|---|
| *A61K 9/06* | (2006.01) |
| *A61K 9/20* | (2006.01) |
| *A61K 9/48* | (2006.01) |
| *A61K 31/095* | (2006.01) |
| *A61K 31/122* | (2006.01) |
| *A61K 31/136* | (2006.01) |
| *A61K 31/167* | (2006.01) |
| *A61K 31/223* | (2006.01) |
| *A61K 47/02* | (2006.01) |
| *A61K 47/10* | (2017.01) |
| *A61K 47/14* | (2017.01) |
| *A61K 47/26* | (2006.01) |
| *A61K 47/44* | (2017.01) |
| *A61P 33/02* | (2006.01) |
| *C07C 50/34* | (2006.01) |
| *C07C 225/30* | (2006.01) |
| *C07C 225/34* | (2006.01) |
| *C07C 237/04* | (2006.01) |
| *C07C 323/52* | (2006.01) |
| *C07C 325/04* | (2006.01) |
| *C07C 327/42* | (2006.01) |

(52) U.S. Cl.
CPC .......... *C07C 237/04* (2013.01); *C07C 325/04* (2013.01); *C07C 327/42* (2013.01); *C07C 2602/10* (2017.05); *C07C 2603/24* (2017.05)

(56) References Cited

U.S. PATENT DOCUMENTS

| | | | |
|---|---|---|---|
| 6,395,517 | B1 | 5/2002 | Abbaszadegan et al. |
| 8,394,379 | B2 | 3/2013 | Imboden et al. |
| 9,346,788 | B2 * | 5/2016 | Wu ........................ A61P 25/00 |
| 2007/0148185 | A1 * | 6/2007 | Rathore ............... C07K 14/445 |
| | | | 514/217.09 |
| 2011/0077250 | A1 * | 3/2011 | Ryder ..................... A61P 33/00 |
| | | | 514/255.06 |

FOREIGN PATENT DOCUMENTS

| | | | |
|---|---|---|---|
| JP | 04-217657 | * | 8/1992 |
| WO | WO 2004089877 | * | 10/2004 |
| WO | WO 2019/043701 | * | 3/2019 |

OTHER PUBLICATIONS

STN printout for Gorelik et al., Stable derivative of 1,10-anthraquinone, Zhurnal Organicheskoi Khimii, vol. 13, No. 2, pp. 463-464 (Year: 1977).*

Pokhilo et al., Regiospecificity in the reaction of 2,3-dichloronaphthazarins with azide anions. Synthesis of echinamine A—a metabolite produced by the sea urchin *Scaphechinus mirabilis*, Tetrahedron Letters, vol. 47, No. 9, pp. 1385-1387 (Year: 2006).*

Abubakar et al., "Prevention and Treatment of Cryptosporidiosis in Immunocompromised Patients (Review)," Cochrane Database Syst. Rev., 1(CD004932), Feb. 2007, 33pgs.

Abubakar et al., "Treatment of Cryptosporidiosis in Immunocompromised Individuals: Systematic Review and Meta-Analysis," Br J Clin Pharmacol. 63(4):387-393, Apr. 2007.

Andrews et al., "Drug Repurposing and Human Parasitic Protozoan Diseases," Int J Parasitol Drugs Drug Resist., 4 (2):95-111, Aug. 2014.

Bobenchik et al., "Plasmodium Falciparum Phosphoethanolamine Methyltransferase Is Essential for Malaria Transmission," Proc Natl Acad Sci USA, 110(45):18262-18267, Nov. 2013.

Downey et al., "Efficacy of Pyrvinium Pamoate against Cryptosporidium parvum Infection In Vitro and in a Neonatal Mouse Model," Antimicrob Agents Chemother., 52(9):3106-3112, Sep. 2008.

Garg et al., "Structure, Function and Inhibition of the Phosphoethanolamine Methyltransferases of the Human Malaria Parasites Plasmodium vivax and Plasmodium knowlesi," Sci Rep., 5:9064, Mar. 2015.

Gargala et al., "Efficacy of Nitazoxanide, Tizoxanide and Tizoxanide Glucuronide Against Cryptosporidium Parvum Development in Sporozoite-Infected HCT-8 Enterocytic Cells," J Antimicrob Chemother., 46(1):57-60, Jul. 2000.

Li et al., "Novel Lactate Dehydrogenase Inhibitors With In Vivo Efficacy Against Cryptosporidium parvum," PLoS Pathog., 15(7):e1007953, Jul. 2019.

Pubchem, "N-(1-Naphthyl)-2-(phenylthio)ethanethioamide," National Library of Medicine, accessed on the internet at https://pubchem.ncbi.nlm.nih.gov/compound/3246501, retrieved Aug. 14, 2020, 15pgs.

Sen et al., "Mathematical Modeling and Omic Data Integration to Understand Dynamic Adaptation of Apicomplexan Parasites and Identify Pharmaceutical Targets," Comprehensive Analysis of Parasite Biology: From Metabolism to Drug Discovery, Jul. 2016, pp. 455-486.

Witola et al., In vitro Anthelmintic Efficacy of Inhibitors of Phosphoethanolamine Methyltransferases in Haemonchus contortus, Int J Parasitol Drugs Drug Resist., 6(1):44-53, Jan. 2016.

Witola et al., "Targeted Gene Knockdown Validates the Essential Role of Lactate Dehydrogenase in Cryptosporidium parvum," Int J Parasitol., 47(13):867-874, Nov. 2017.

Zhang et al., "Cryptosporidium Lactate Dehydrogenase Is Associated With the Parasitophorous Vacuole Membrane and Is a Potential Target for Developing Therapeutics," PLoS Pathog., 12;11(11):e1005250, Nov. 2015.

Zhang et al., "Morpholino-Mediated In Vivo Silencing of Cryptosporidium parvum Lactate Dehydrogenase Decreases Oocyst Shedding and Infectivity," Int J Parasitol., 48(8):649-656, Jul. 2018.

* cited by examiner

COMPOUNDS AND METHODS FOR THE TREATMENT OF PARASITIC INFECTIONS

RELATED APPLICATIONS

This application is a National Stage filing under 35 U.S.C. § 371 of International Application No. PCT/US2020/036336 filed Jun. 5, 2020, which claims priority under 35 U.S.C. § 119 (e) to U.S. Provisional Patent Application No. 62/858,551, filed Jun. 7, 2019, which applications are incorporated herein by reference.

BACKGROUND OF THE INVENTION

The zoonotic and anthroponotic protozoan parasite, *Cryptosporidium parvum*, is a major cause of diarrheal diseases in children under the age of two, resulting in significant morbidity and mortality in poor-resource areas of developing countries. In livestock, particularly in calves, lambs and goat kids, it causes a serious diarrheal syndrome, culminating in growth retardation and high neonatal mortalities. *C. parvum* is highly prevalent because of its enormous capacity to reproduce in infected livestock, resulting in large amounts of infective parasite oocysts being shed in animal feces, and contaminating water sources as well as the general environment. The parasite oocysts in the environment are difficult to eliminate because of their resistance to virtually all kinds of chemical disinfectants, as well as to commonly used water treatments such as chlorination. The efficacy of the only FDA-approved anti-*Cryptosporidium* drug in humans, nitazoxanide, is modest. Of particular concern, nitazoxanide is ineffective in those individuals most at risk for morbidity and mortality due to *Cryptosporidium* infections, including malnourished children and immunocompromised individuals. There is currently no vaccine against *Cryptosporidium* infections.

Efforts to develop fully effective drugs against *Cryptosporidium* have largely been hampered by the lack of genetic tools for functional interrogation and validation of potential molecular drug targets in the parasite. Recently, however, a CRISPR/Cas9 gene manipulation approach, and a morpholino-based targeted gene knockdown approach in *C. parvum* have been developed. The completed and annotated genome sequence of *Cryptosporidium* indicates that, while the parasite lacks genes for conventional molecular drug targets found in other important protozoan parasites, it has several genes encoding plant-like and bacterial-like enzymes that catalyze potentially essential biosynthetic and metabolic pathways in *Cryptosporidium*. Using a morpholino-based approach for targeted gene knockdown in *C. parvum*, we have previously validated that the *C. parvum* lactate dehydrogenase gene (CpLDH) that encodes a bacterial-like enzyme, is essential for survival, virulence and reproduction of *C. parvum* both in vitro and in vivo.

Accordingly, there is a need for a safe and effective treatment for parasitic infections particularly in malnourished and immunocompromised individuals in whom current drug treatments are ineffective.

SUMMARY

This disclosure provides compounds discovered to have an inhibitory effect against the enzymatic activity of recombinant CpLDH protein in vitro. Among the identified CpLDH inhibitors, we have demonstrated that two of the inhibitors can effectively block the growth, proliferation, and pathogenicity of *C. parvum* in vivo at tolerable doses, suggesting that they are potential candidates for development of drugs against *C. parvum* infections.

Accordingly, this disclosure provides a compound of Formula I or Formula II:

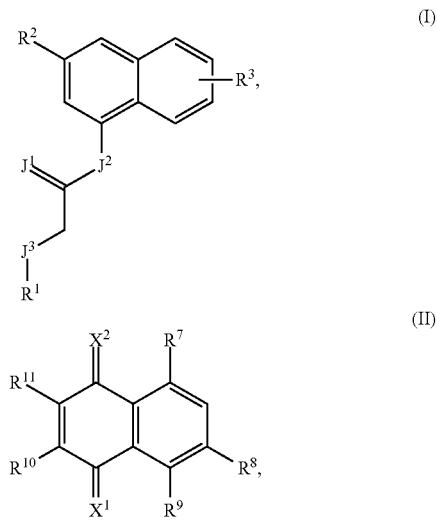

or a salt thereof;
wherein
$J^1$, $J^2$, and $J^3$ are each independently O, S, or $NR^Z$ wherein $R^Z$ is H, $-(C_1-C_6)$alkyl, or $-(C_3-C_6)$cycloalkyl;
$X^1$ and $X^2$ are independently O or S;
$R^1$ is

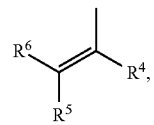

heterocycloalkyl, aryl, or heteroaryl;
$R^2$ is H, halo, OH, SH, $NR^AR^B$, $-C(=O)OR^C$, $-S(=O)_2 NR^CR^D$, $-(C_1-C_6)$alkyl, $-O(C_1-C_6)$alkyl, $-S(C_1-C_6)$alkyl, $-(C_3-C_6)$cycloalkyl, $-O(C_3-C_6)$cycloalkyl, $-S(C_3-C_6)$cycloalkyl, heterocycloalkyl, aryl, or heteroaryl, wherein aryl or heteroaryl is unsubstituted or substituted;
$R^3$ is H, halo, or OH;
$R^4$ and $R^5$ are independently halo, OH, SH, $NR^AR^B$, $-C(=O)_{OR}{}^C$, or $-S(=O)_2NR^CR^D$;
$R^6$ is H, $-(C_1-C_6)$alkyl, or $-(C_3-C_6)$cycloalkyl;
$R^7$, $R^8$ and $R^9$ are independently halo, OH, SH, $NR^AR^B$, $-C(=O)OR^C$, or $-S(=O)_2NR^CR^D$;
$R^{10}$ and $R^{11}$ are independently halo, OH, SH, $NR^AR^B$, $-C(=O)OR^C$, $-S(=O)_2NR^CR^D$; or
$R^{10}$ and $R^{11}$ taken together form a 6-membered fused aryl ring wherein the fused aryl ring is unsubstituted or substituted; and
$R^A$, $R^B$, $R^c$, and $R^D$ are each independently H, $-(C_1-C_6)$alkyl, or $-(C_3-C_6)$cycloalkyl;
provided that when $J^1$ and $J^3$ are S, $J^2$ is NH, and $R^2$ and $R^3$ are H, $R^1$ is not unsubstituted phenyl: and
when $X^1$ and $X^2$ are O, $R^7$, $R^8$ and $R^9$ are OH, and $R^{10}$ and $R^{11}$ form a fused benzo moiety, the fused benzo moiety is not unsubstituted.

This disclosure also provides a method for treating a parasitic infection comprising administering to a subject in need thereof a therapeutically effective amount of a compound of Formula I or Formula II, as shown above, thereby killing or inhibiting the growth of at least a portion of a plurality of parasites in the subject.

In some embodiments the compound is NSC158011 or NSC10447:

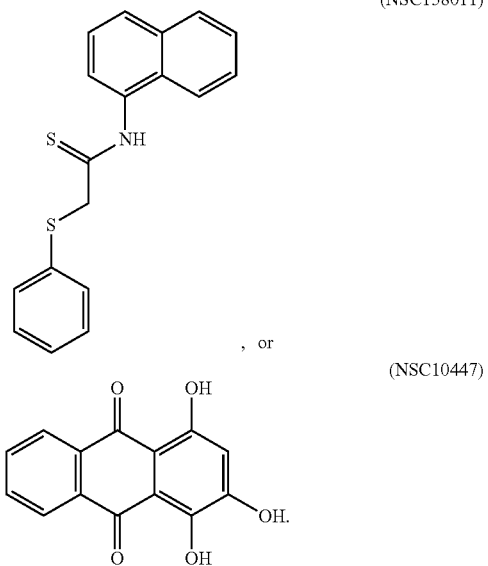

The invention provides novel compounds of Formula I, Formulas IA-IH, Formula II, Formula III, Formulas IVA-IVF, and Formulas VA-VE, intermediates for the synthesis of compounds of said Formulas, as well as methods of preparing compounds of said Formulas. The invention also provides compounds of Formula I, Formulas IA-IH, Formula II, Formula III, Formulas IVA-IVF, and Formulas VA-VE that are useful as intermediates for the synthesis of other useful compounds. The invention provides for the use of compounds of said Formulas for the manufacture of medicaments useful for the treatment of bacterial infections in a mammal, such as a human.

The invention provides for the use of the compositions described herein for use in medical therapy. The medical therapy can be treating infections, for example, parasitic infections. The invention also provides for the use of a composition as described herein for the manufacture of a medicament to treat infections in a mammal, for example, *C. parvum* infections in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
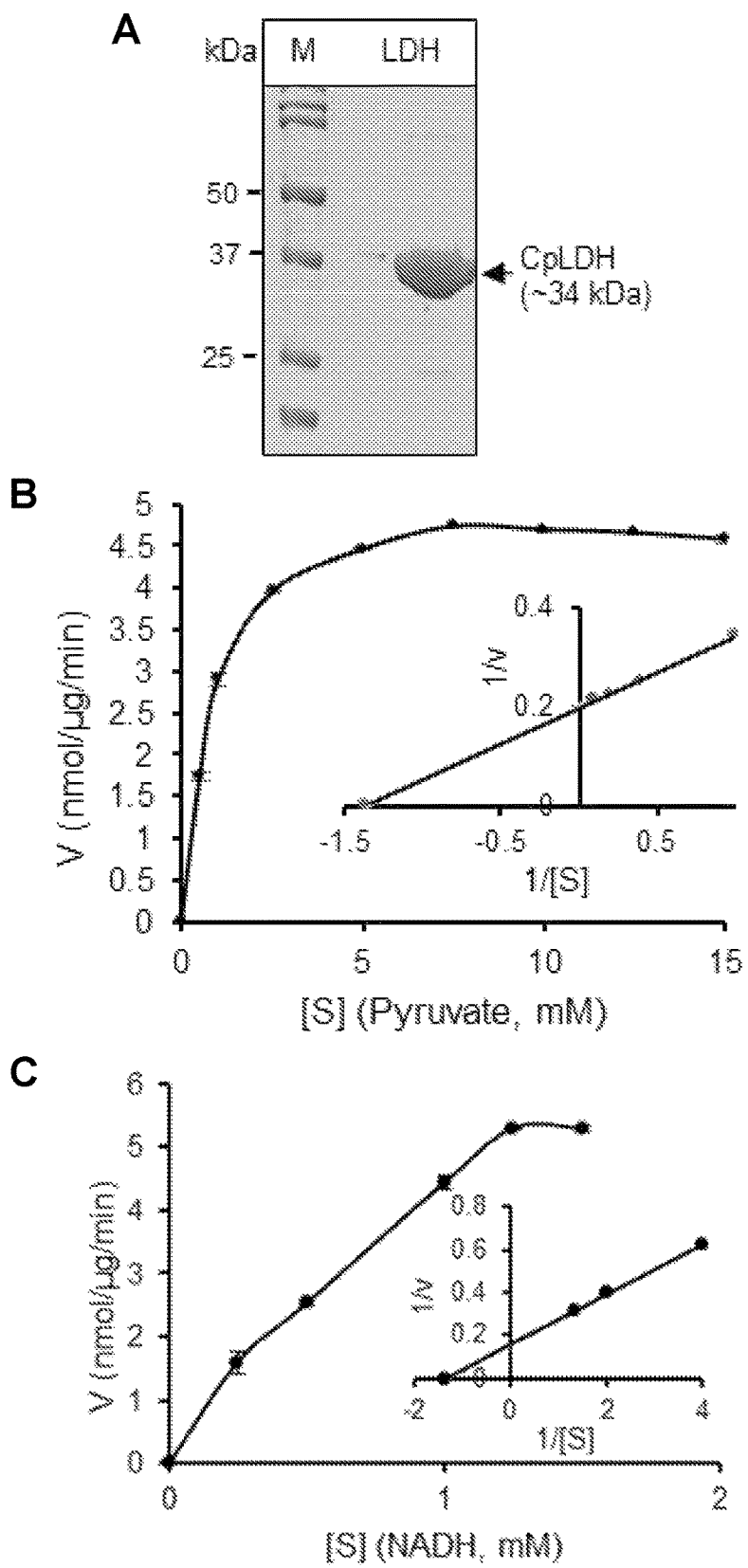
FIG. 1. Analysis of the enzymatic activity of recombinant CpLDH protein. (A) SDS-PAGE analysis of the nickel affinity column chromatography-purified His-tagged recombinant CpLDH protein stained with coomassie blue (Lane M: protein ladder; Lane LDH: CpLDH protein). (B and C) Enzyme kinetics of recombinant CpLDH protein for the reduction of pyruvate to lactate on pyruvate as substrate (B), and NADH as co-factor (C). (D and E) Enzyme kinetics of recombinant CpLDH protein for the oxidation of lactate to pyruvate on lactate as substrate (D), and NAD+ as co-factor (E). Insets are Lineweaver-Burk representations of the saturation curves. S, substrate; V, velocity of the reaction. The data shown represent means of three independent experiments.
Figure 1:
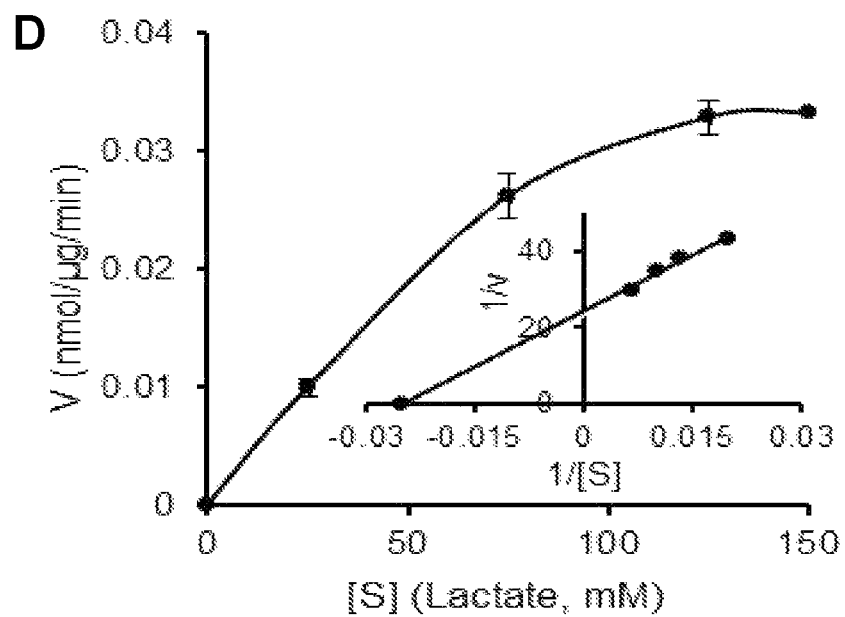
Figure 1:
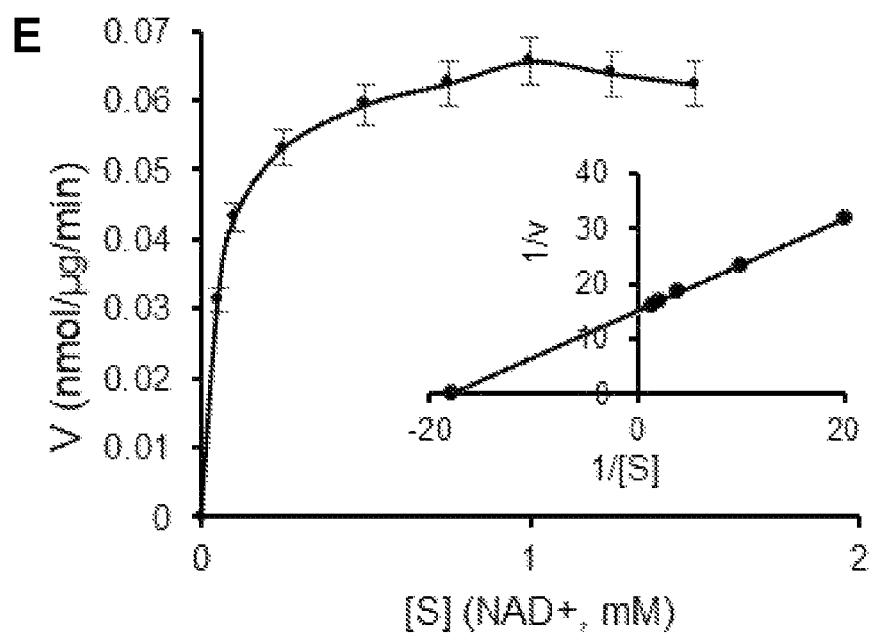

*Cryptosporidium parvum* is a protozoan parasite that can cause a life-threatening gastrointestinal disease in children and in immunocompromised adults. The only approved drug for treatment of *Cryptosporidium* infections in humans is nitazoxanide, but it is not effective in immunocompromised individuals or in children with malnutrition. *C. parvum* possesses a unique lactate dehydrogenase (CpLDH) enzyme that it uses for generating metabolic energy (ATP) via the glycolytic pathway to fuel its growth and proliferation in the host. We have identified novel inhibitors for the enzymatic activity of CpLDH. Further, we have demonstrated that two of the CpLDH inhibitors effectively block the growth, proliferation and pathogenicity of *C. parvum* at tolerable doses in immunocompromised mice. Together, our findings have unveiled novel CpLDH inhibitors that can be explored for the development of efficacious therapeutic drugs against *C. parvum* infections.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, infection, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, such as a vertebrate, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of a compound of the disclosure into a subject by a method or route that results in at least partial localization of the compound to a desired site. The compound can be administered by any appropriate route that results in delivery to a desired location in the subject.

The compound and compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms; or for example, a range between 1-20 carbon atoms, such as 2-6, 3-6, 2-8, or 3-8 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below or otherwise described herein. The alkyl can also be optionally partially or fully unsaturated. As such, the recitation of an alkyl group can include an alkenyl group or an alkynyl group. The alkyl can be a monovalent hydrocarbon radical, as described and exemplified above, or it can be a divalent hydrocarbon radical (i.e., an alkylene).

An alkylene is an alkyl group having two free valences at a carbon atom or two different carbon atoms of a carbon chain. Similarly, alkenylene and alkynylene are respectively an alkene and an alkyne having two free valences at two different carbon atoms.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, etc.

The term "heterocycloalkyl" or "heterocyclyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted with a substituent described below.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms, wherein the ring skeleton comprises a 5-membered ring, a 6-membered ring, two 5-membered rings, two 6-membered rings, or a 5-membered ring fused to a 6-membered ring. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

As used herein, the term "substituted" or "substituent" is intended to indicate that one or more (for example, in various embodiments, 1-10; in other embodiments, 1-6; in some embodiments 1, 2, 3, 4, or 5; in certain embodiments, 1, 2, or 3; and in other embodiments, 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, haloalkyl, hydroxyalkyl, aryl, heteroaryl, heterocyclyl, cycloalkyl, alkanoyl, alkoxycarbonyl, amino, alkylamino, dialkylamino, carboxyalkyl, alkylthio, alkylsulfinyl, and alkylsulfonyl. Substituents of the indicated groups can be those recited in a specific list of substituents described herein, or as one of skill in the art would recognize, can be one or more substituents selected from alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Suitable substituents of indicated groups can be bonded to a substituted carbon atom include F, Cl, Br, I, OR', OC(O)N(R')2, CN, CF3, OCF3, R', O, S, C(O), S(O), methylenedioxy, ethylenedioxy, N(R')2, SR', SOR', SO2R', SO2N(R')2, SO3R', C(O)R', C(O)C(O)R', C(O)CH2C(O)R', C(S)R', C(O)OR', OC(O)R', C(O)N(R')2, OC(O)N(R')2, C(S)N(R')2, (CH2)0-2NHC(O)R', N(R')N (R')C(O)R', N(R')N(R')C(O)OR', N(R')N(R')CON(R')2, N(R')SO2R', N(R')SO2N(R')2, N(R')C(O)OR', N(R')C(O) R', N(R')C(S)R', N(R')C(O)N(R')2, N(R')C(S)N(R')2, N(COR')COR', N(OR')R', C(=NH)N(R')2, C(O)N(OR')R', or C(=NOR')R' wherein R' can be hydrogen or a carbon-based moiety (e.g., (C1-C6)alkyl), and wherein the carbon-based moiety can itself be further substituted. When a substituent is monovalent, such as, for example, F or Cl, it is bonded to the atom it is substituting by a single bond. When a substituent is divalent, such as O, it is bonded to the atom it is substituting by a double bond; for example, a carbon atom substituted with O forms a carbonyl group, C=O.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof, such as racemic mixtures, which form part of the present invention. Many organic compounds exist in optically active forms, i.e., they have the ability to rotate the plane of plane-polarized light. In describing an optically active compound, the prefixes D and L, or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate (defined below), which may occur where there has been no stereoselection or stereospecificity in a chemical reaction or process.

The term "$IC_{50}$" is generally defined as the concentration required to kill 50% of the cells or parasites in 24 hours.

The term "endogenous" in the context of this disclosure refers to biological elements of a living organism or life form that are expressed by the genes of the organism. For example, the enzyme lactate dehydrogenase (LDH) expressed by the genes of *Cryptosporidium parvum* i.e., CpLDH, is an enzyme endogenous to *C. parvum*. LDH expressed by the genes of a human is an enzyme endogenous human. Such biological elements that are expressed in different species are also different in their protein structure even though they have similar functions. These differences in protein structure can be advantageous in the design and/or discovery of inhibitors, such as the compounds disclosed herein which can bind with higher affinity CpLDH and lower affinity to human LDH.

EMBODIMENTS OF THE INVENTION

This disclosure provides a compound of Formula I or Formula II:

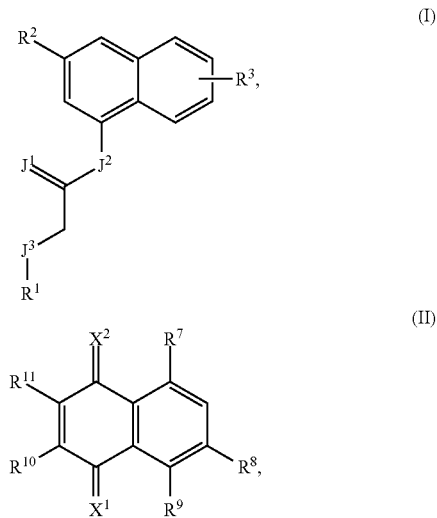

or a salt thereof;
wherein
  $J^1$, $J^2$, and $J^3$ are each independently O, S, or $NR^Z$ wherein $R^Z$ is H, —$(C_1$-$C_6)$alkyl, or —$(C_3$-$C_6)$cycloalkyl;
  $X^1$ and $X^2$ are independently O or S;
  $R^1$ is

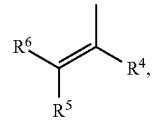

heterocycloalkyl, aryl, or heteroaryl;
  $R^2$ is H, halo, OH, SH, $NR^AR^B$, —C(=O)$OR^C$, —S(=O)$_2$ $NR^CR^D$, —$(C_1$-$C_6)$alkyl, —O$(C_1$-$C_6)$alkyl, —S$(C_1$-$C_6)$alkyl, —$(C_3$-$C_6)$cycloalkyl, —O$(C_3$-$C_6)$cycloalkyl, —S$(C_3$-$C_6)$cycloalkyl, heterocycloalkyl, aryl, or heteroaryl, wherein aryl or heteroaryl is unsubstituted or substituted;
  $R^3$ is H, halo, or OH;
  $R^4$ and $R^5$ are independently halo, OH, SH, $NR^AR^B$, —C(=O)$OR^C$, or —S(=O)$_2NR^CR^D$;
  $R^6$ is H, —$(C_1$-$C_6)$alkyl, or —$(C_3$-$C_6)$cycloalkyl;
  $R^7$, $R^8$ and $R^9$ are independently halo, OH, SH, $NR^AR^B$, —C(=O)$OR^C$, or —S(=O)$_2NR^CR^D$;
  $R^{10}$ and $R^{11}$ are independently halo, OH, SH, $NR^AR^B$, —C(=O)$OR^C$, —S(=O)$_2NR^CR^D$; or
  $R^{10}$ and $R^{11}$ taken together form a 6-membered fused aryl ring wherein the fused aryl ring is unsubstituted or substituted; and
  $R^A$, $R^B$, $R^C$, and $R^D$ are each independently H, —$(C_1$-$C_6)$ alkyl, or —$(C_3$-$C_6)$cycloalkyl;

provided that, in certain embodiments, the compound of Formula I is not

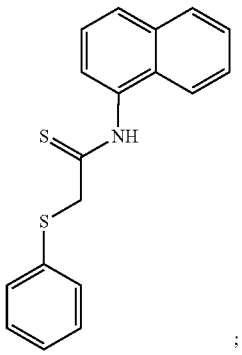
(NSC158011)

;

and provided that, in certain embodiments, the compound of Formula II is not

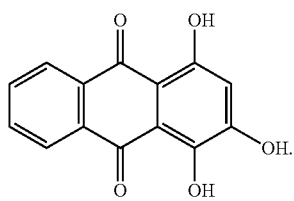
(NSC10447)

In some embodiments, the compound of Formula I is a compound of Formula IA or IB:

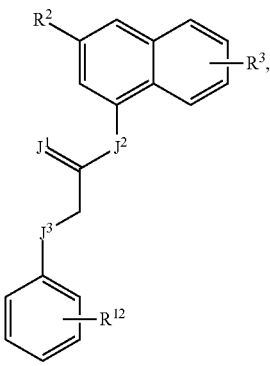
(IA)

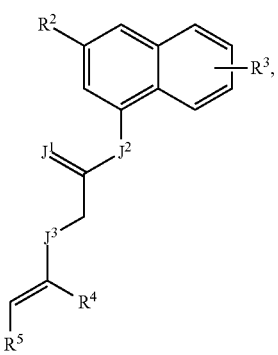
(IB)

or a salt thereof;

wherein $J^1$ is O or S;

$J^2$ is O or NH;

$J^3$ is S or NH;

$R^4$ and $R^5$ are independently fluoro, chloro, bromo, OH, or $NH_2$; and $R^{12}$ is H, halo, OH, or —$(C_1\text{-}C_6)$alkyl.

In some embodiments, the compound of Formula I is a compound of Formula IC, ID, IE, IF, IG, or IH:

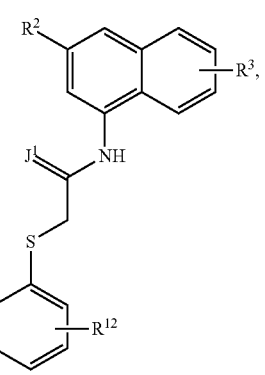
(IC)

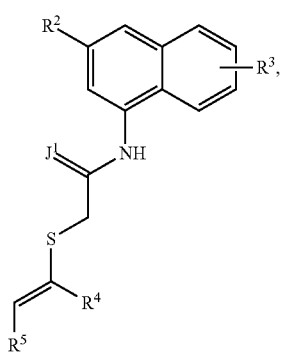
(ID)

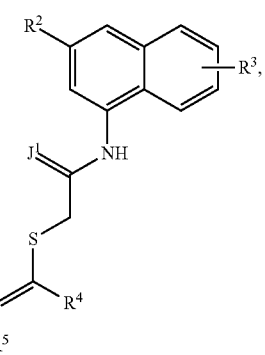
(IE)

-continued (IF)
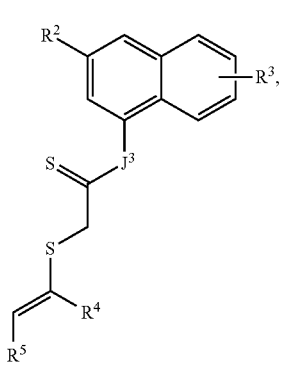

(IG)
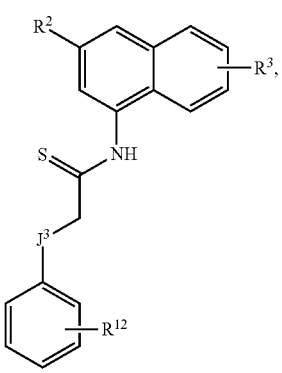

(IH)
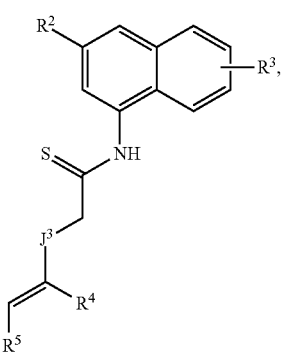

or a salt thereof.

In other embodiments, $R^1$ of Formula I is phenyl, 1,2-dichloroethen-1-yl, 1,2-dibromoethen-1-yl, 1,2-difluoroethen-1-yl, 1,2-dihydroxyethen-1-yl, 1,2-diaminoethen-1-yl, 1-chloro-2-hydroxyethen-1-yl, 1-hydroxy-2-chloroethen-1-yl, 1-hydroxy-2-aminoethen-1-yl, 1-amino-2-hydroxyethen-1-yl, 1-amino-2-chloroethen-1-yl, 1-chloro-2-aminoethen-1-yl, 1-bromo-2-aminoethen-1-yl, 1-bromo-2-hydroxyethen-1-yl, 1-bromo-2-aminoethen-1-yl, 1-bromo-2-chloroethen-1-yl, 1-hydroxy-2-bromoethen-1-yl, 1-amino-2-bromoethen-1-yl, 1-chloro-2-bromoethen-1-yl, 1-chloro-2-fluoroethen-1-yl, 1-amino-2-fluoroethen-1-yl, 1-hydroxy-2-fluoroethen-1-yl, or 1-bromo-2-fluoroethen-1-yl.

In additional embodiments, the compound is a compound of Formula II, wherein $R^7$, $R^8$, $R^9$, $R^{10}$, and $R^{11}$ are independently halo, OH, or $NH_2$.

In some other embodiments, the compound of Formula II is a compound of Formula III:

(III)
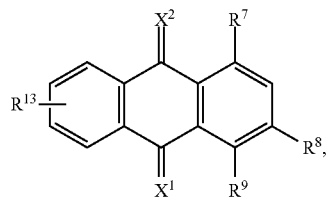

or a salt thereof;
wherein
$R^7$, $R^8$ and $R^9$ are independently halo, OH, or $NH_2$; and
$R^{13}$ is H, halo, OH, or —$(C_1$-$C_6)$alkyl.

In additional embodiments, $X^1$ and $X^2$ are O. In other embodiments, $X^1$ is O and $X^2$ is S, or $X^1$ is S and $X^2$ is O.

In some other embodiments, the compound of Formula II is a compound of Formula IVA, IVB, IVC, IVD, or IVE:

(IVA)
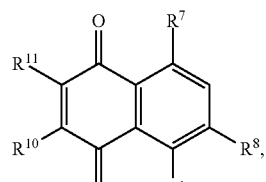

(IVB)
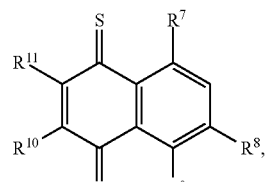

(IVC)
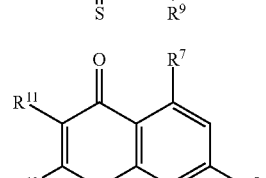

(IVD)
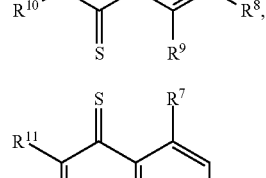

(IVE)
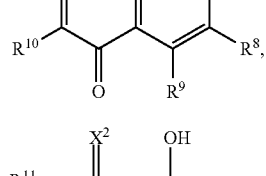

-continued
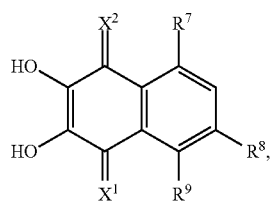
or a salt thereof;
In some other embodiments, the compound of Formula II is a compound of Formula VA, VB, VC, VD, or VE:
(VA)
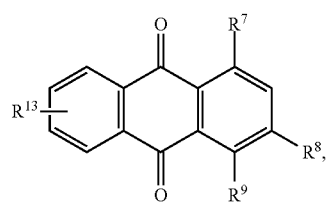
(VB)
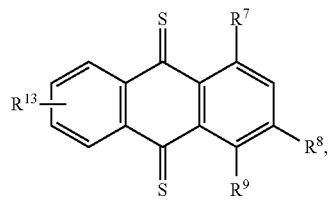
(VC)
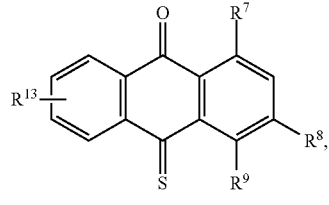
(VD)
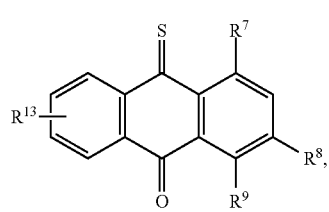
(VE)
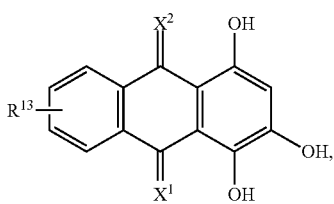
or a salt thereof;
In some embodiments, the compound is:
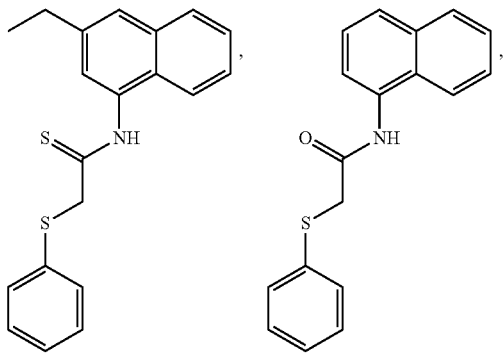
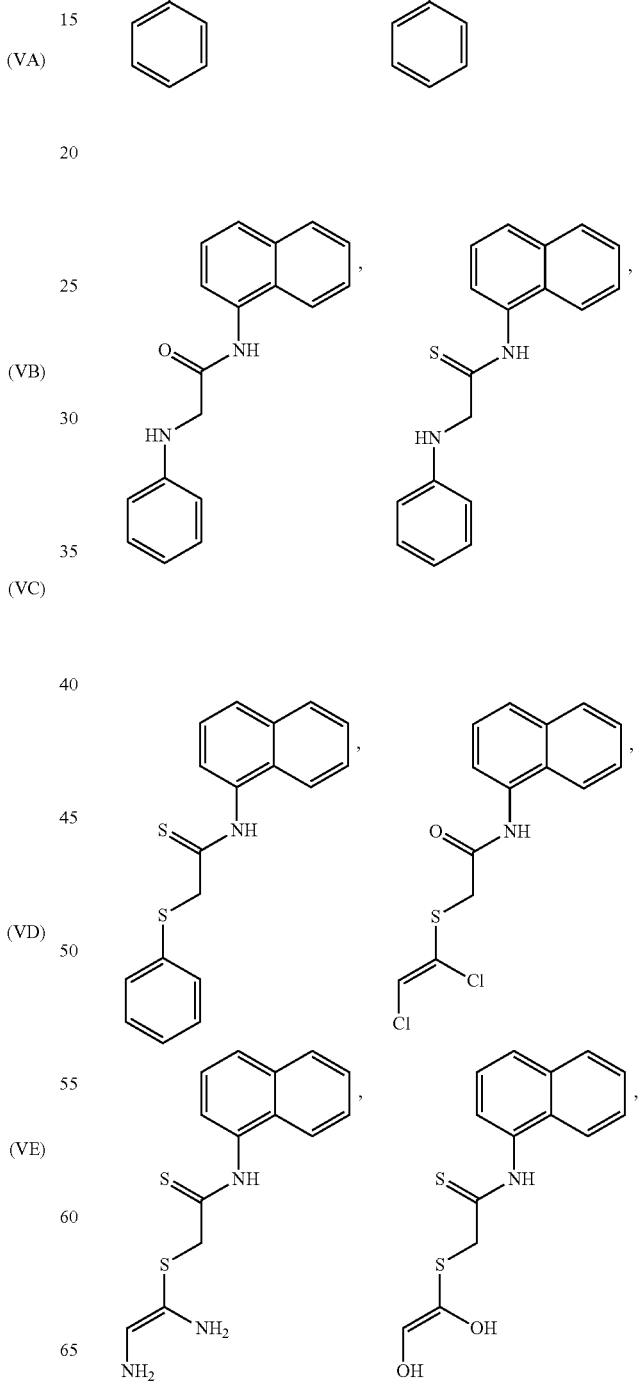

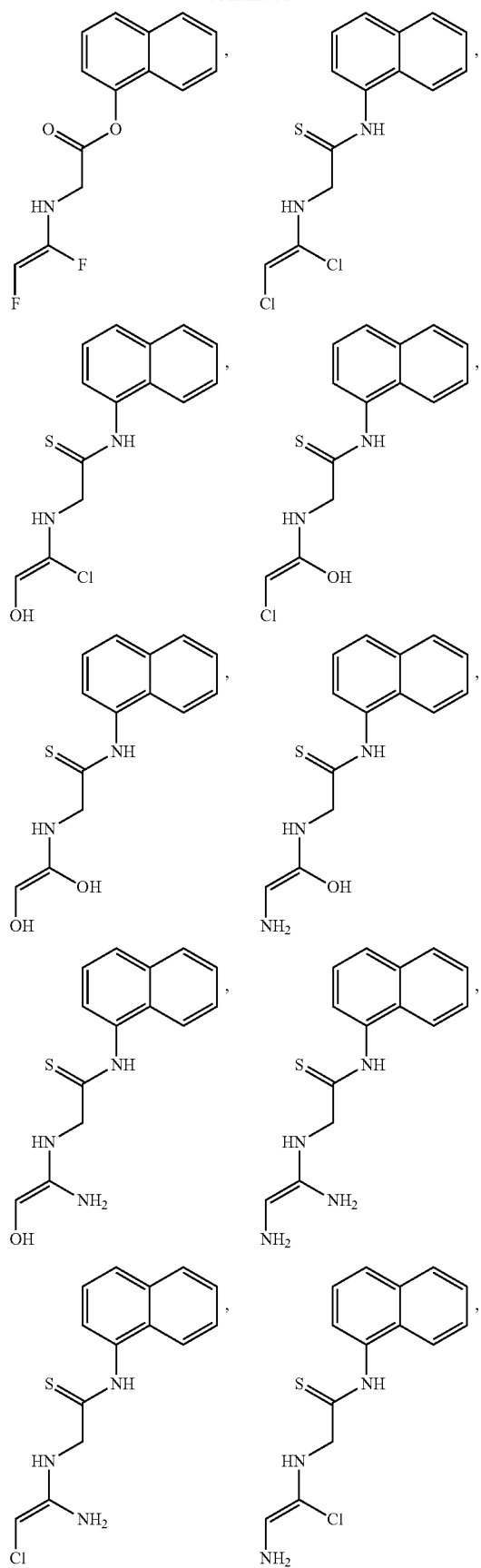
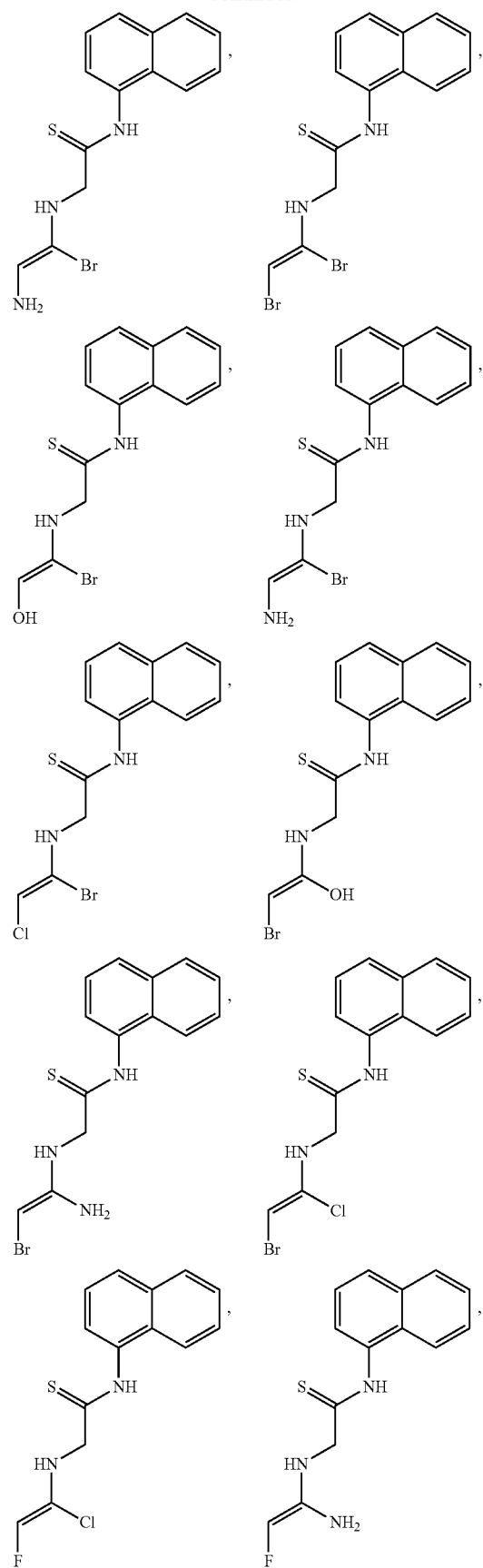

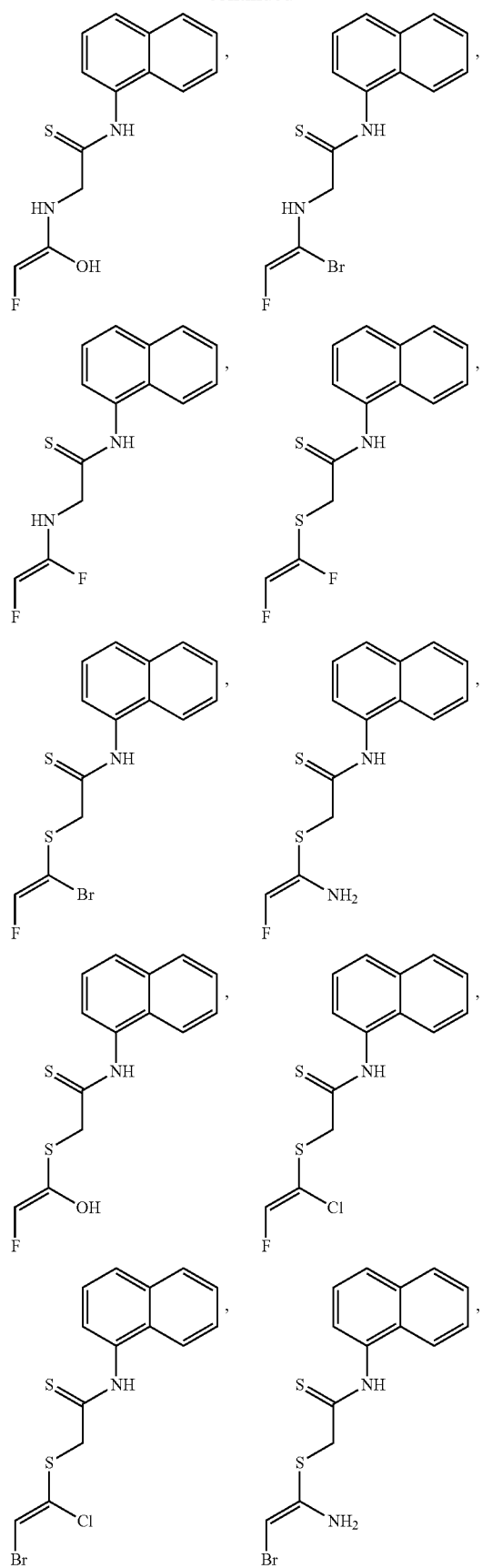
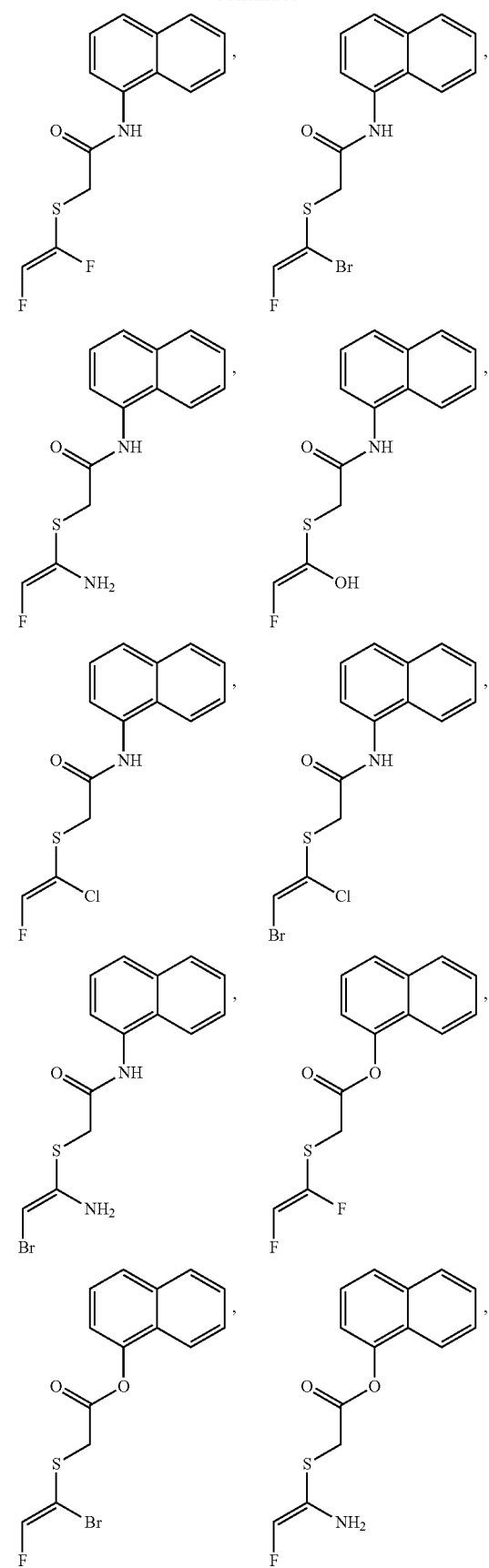

-continued
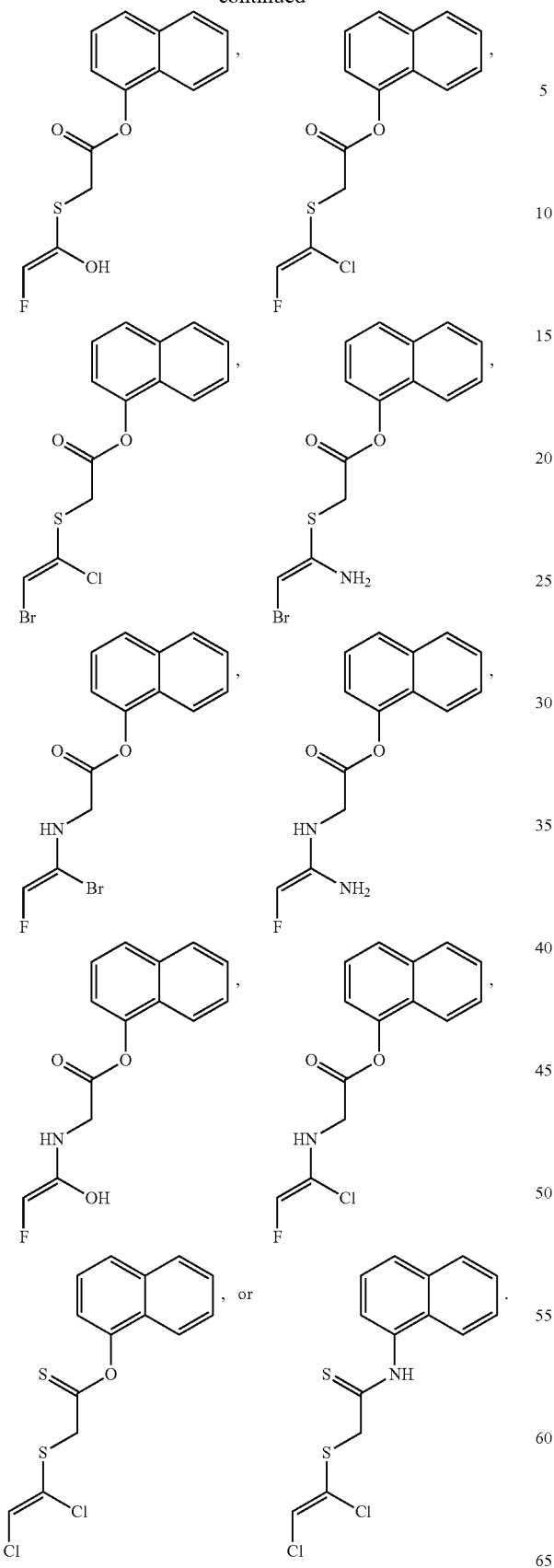
In other embodiments, the compound is:
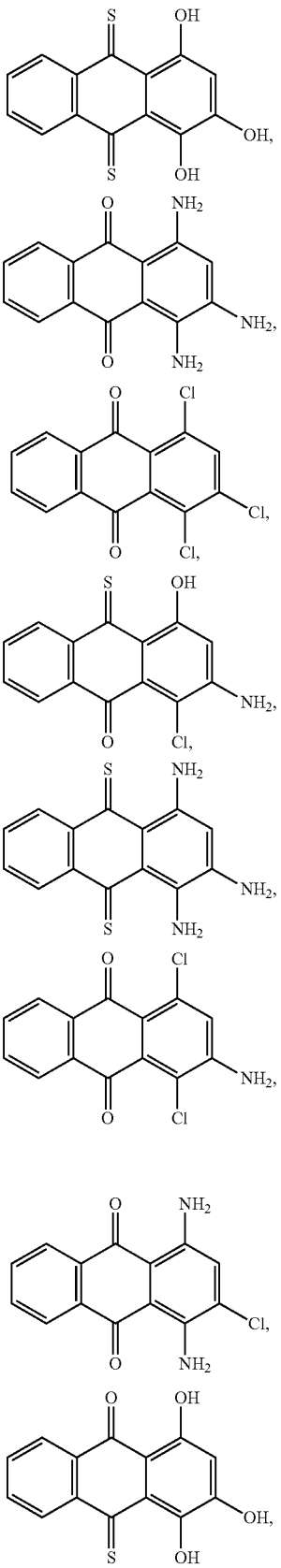

-continued
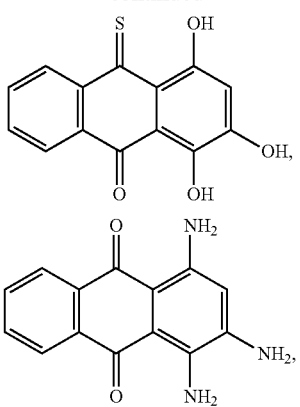
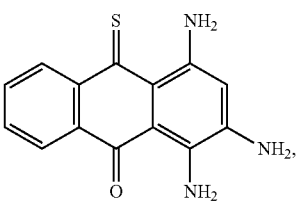
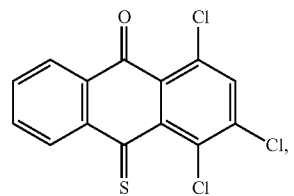
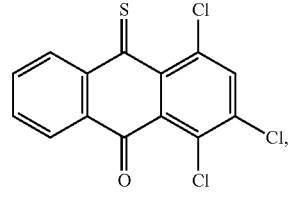
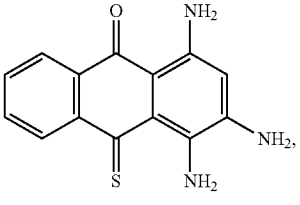
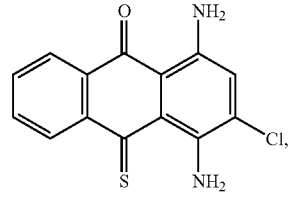
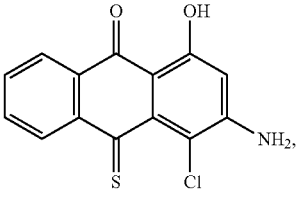
-continued
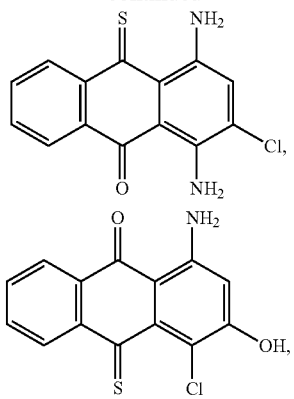
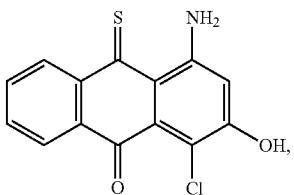
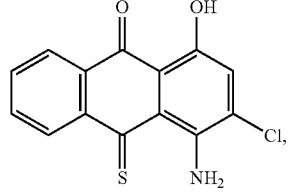
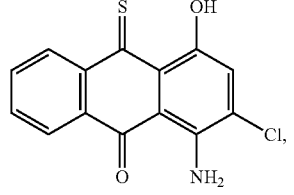
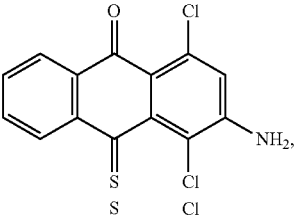
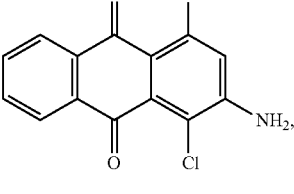
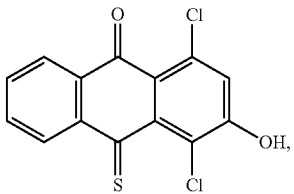

-continued
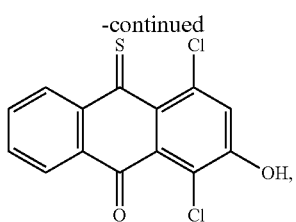
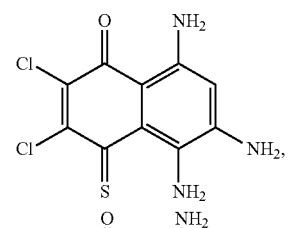
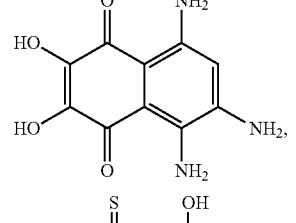
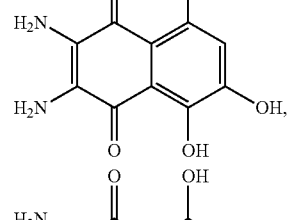
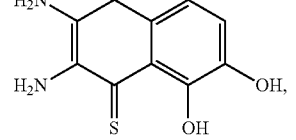
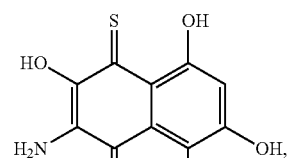
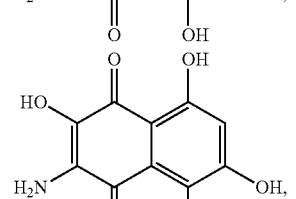
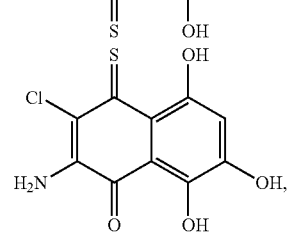
-continued
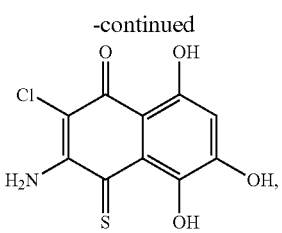
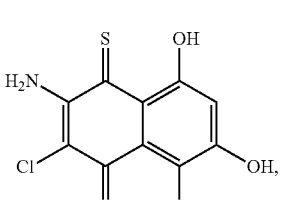
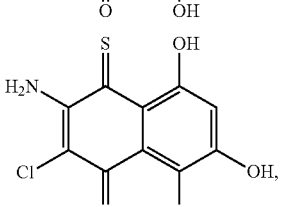
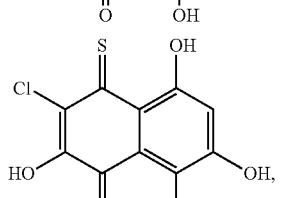
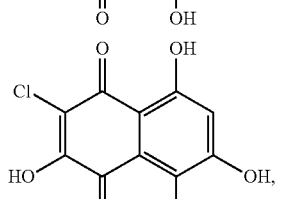
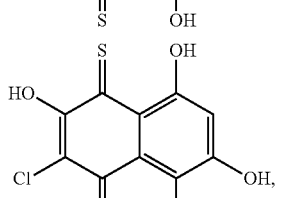
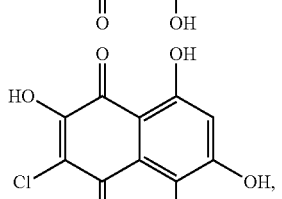
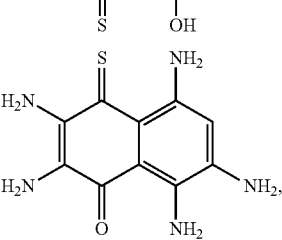

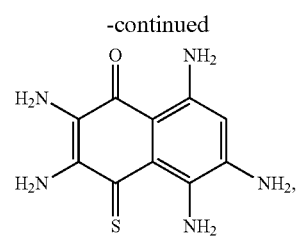

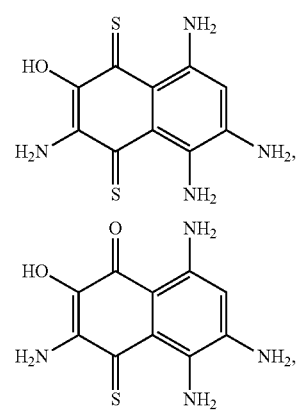

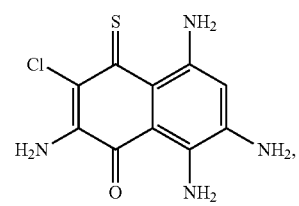

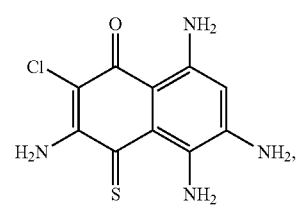

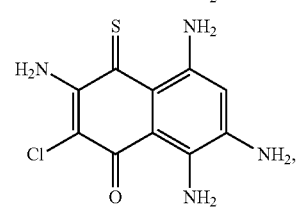

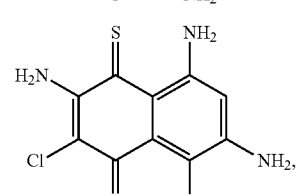

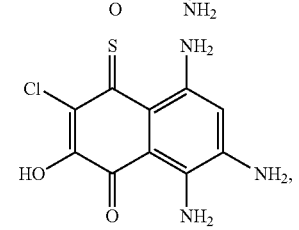

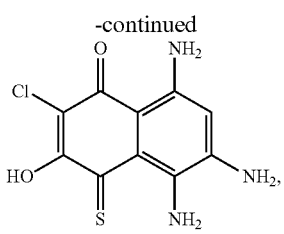

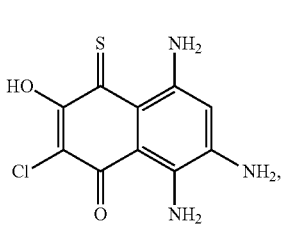

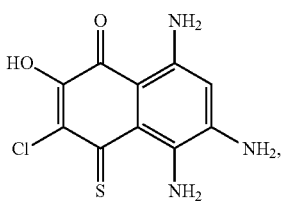

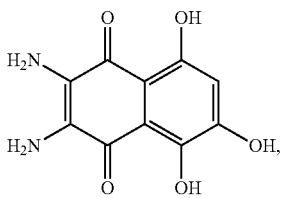

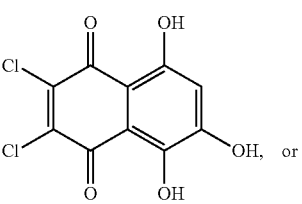

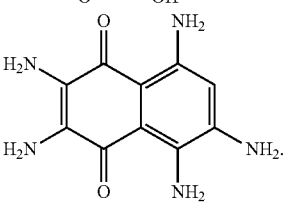

Also, this disclosure provides a pharmaceutical composition comprising a compound of disclosed herein in combination with a pharmaceutically acceptable diluent, carrier, excipient, or buffer, wherein the compound is a compound of Formula I, Formula II, or a combination thereof.

Additionally, this disclosure provides a method for treating a parasitic infection comprising administering to a subject in need thereof a therapeutically effective amount of a compound of Formula I or Formula II:

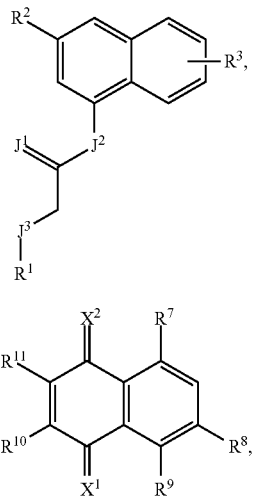

(I)

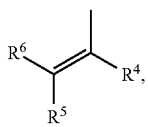

(II)

or a salt thereof;
wherein
  J¹, J², and J³ are each independently O, S, or NR$^Z$ wherein R$^Z$ is H, —(C$_1$-C$_6$)alkyl, or —(C$_3$-C$_6$)cycloalkyl;
  X¹ and X² are independently O or S;
  R¹ is heterocycloalkyl, aryl, or heteroaryl;
  R² is H, halo, OH, SH, NR$^A$R$^B$, —C(=O)OR$^C$, —S(=O)$_2$NR$^C$R$^D$, —(C$_1$-C$_6$)alkyl, —O(C$_1$-C$_6$)alkyl, —S(C$_1$-C$_6$)alkyl, —(C$_3$-C$_6$)cycloalkyl, —O(C$_3$-C$_6$)cycloalkyl, —S(C$_3$-C$_6$)cycloalkyl, heterocycloalkyl, aryl, or heteroaryl, wherein aryl or heteroaryl is unsubstituted or substituted;
  R³ is H, halo, or OH;
  R⁴ and R⁵ are independently halo, OH, SH, NR$^A$R$^B$, —C(=O)OR$^C$, or —S(=O)$_2$NR$^C$R$^D$;
  R⁶ is H, —(C$_1$-C$_6$)alkyl, or —(C$_3$-C$_6$)cycloalkyl;
  R⁷, R⁸ and R⁹ are independently halo, OH, SH, NR$^A$R$^B$, —C(=O)OR$^C$, or —S(=O)$_2$NR$^C$R$^D$;
  R¹⁰ and R¹¹ are independently halo, OH, SH, NR$^A$R$^B$, —C(=O)OR$^C$, —S(=O)2NR$^C$R$^D$; or
  R¹⁰ and R¹¹ taken together form a 6-membered fused aryl ring wherein the fused aryl ring is unsubstituted or substituted; and
  R$^A$, R$^B$, R$^C$, and R$^D$ are each independently H, —(C$_1$-C$_6$)alkyl, or —(C$_3$-C$_6$)cycloalkyl; thereby killing or inhibiting the growth of at least a portion of a plurality of parasites in the subject.

In additional embodiments, the compound is NSC158011 or NSC10447:

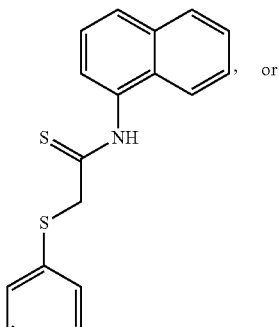

(NSC158011), or

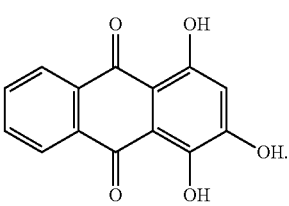

(NSC10447)

In various embodiments, the parasite of the parasitic infection is *Cryptosporidium parvum*. In various other embodiments, the subject is infected with *C. parvum* and is shedding *C. parvum* oocysts wherein treatment reduces the shedding of oocysts to undetectable levels as quantified by real-time polymerase chain reaction. In additional embodiments, the subject is malnourished, immunocompromised, or a combination thereof.

In other various embodiments, the compound selectively inhibits a lactate dehydrogenase (LDH) enzyme endogenous to the parasite and in the presence of an LDH enzyme endogenous to the subject infected with the parasite. In other additional embodiments, the compound selectively binds to the co-factor binding site of the LDH enzyme endogenous to the parasite.

In some embodiments, the therapeutically effective amount of the compound is an oral dose of about 100 mg/kg to about 2000 mg/kg per day for one or more days. In some other embodiments, the effective daily oral dose is about 200 mg/kg, about 300 mg/kg, about 400 mg/kg, about 500 mg/kg, about 600 mg/kg, about 700 mg/kg, about 800 mg/kg, about 900 mg/kg, about 1000 mg/kg, about 1100 mg/kg, about 1200 mg/kg, about 1300 mg/kg, about 1400 mg/kg, about 1500 mg/kg, about 1600 mg/kg, about 1700 mg/kg, about 1800 mg/kg, about 1900 mg/kg, about 2500 mg/kg, about 3000 mg/kg, or a dose in-between two recited doses.

In yet other embodiments, the effective dose is a dose that maintains a steady state plasma concentration of about 1 nanomolar to about 10 micromolar, about 10 nanomolar to about 9 micromolar, about 100 nanomolar to about 8 micromolar, about 250 nanomolar to about 7 micromolar, about 500 nanomolar to about 6 micromolar, about 1 micromolar to about 5 micromolar, about 15 micromolar, about 20 micromolar, about 25 micromolar, about 30 micromolar, about 35 micromolar, about 40 micromolar, about 45 micromolar, about 50 micromolar, about 75 micromolar, or about 100 micromolar.

In other embodiments, the treated subject has intact intestinal epithelium with prominent villi comparable to an uninfected control subject. In yet other embodiments, the compound in combination with a second active agent is administered simultaneously or sequentially to treat the parasitic infection.

Results

Enzymatic activity of recombinant CpLDH protein. By sequencing, the cloned open reading frame of CpLDH gene was verified to be 966 bp long, and 99.79% identical to that reported in the genome database (GenBank accession number AF274310.1). It coded for a 321 amino acids long protein with amino acid residue substitutions of F-198-L, R-251-K and K-295-E when compared to that in GenBank. The expressed and purified His-tagged CpLDH protein was of the expected molecular size of about 34 kDa (FIG. 1A). By analyzing the in vitro catalytic activities of recombinant CpLDH, we found that it depicted more activity in catalyzing the reduction of pyruvate to lactate than the oxidation of lactate to pyruvate. We found that recombinant CpLDH enzymatic catalytic activity was consistent with the Michaelis-Menten kinetics on pyruvate, NADH, lactate and NAD$^+$ (FIG. 1B-E). The Lineweaver-Burk representation of the saturation curves (insets in FIG. 1B-E) showed that the Km of recombinant CpLDH for pyruvate was at least 54-fold lower than that for lactate, while its Vmax for pyruvate was 123-fold higher than that for lactate (Table 1). Our obtained enzymatic kinetic parameters for recombinant CpLDH in comparison to those reported previously for *C. parvum* CpLDH (Zhang et al., PLoS Pathog. 2015; 11(11), e1005250) are summarized in Table 1.

pher the differences in the interactions of NSC150811 and NSC10447 (Scheme 1) with CpLDH and human LDH proteins, an in silico molecular docking using Autodock Vina (J. Comput. Chem. 2010; 31(2), 455-461) was performed to determine the most energetically favorable poses of the compounds complexed with the rigid structures of both CpLDH and human LDH. Both compounds were found to bind most favorably into the co-factor-binding pocket of the CpLDH and human LDH, where NADH binds to reduce pyruvate to lactate.

Scheme 1. Chemical structures of NSC158011 (A) and NSC10447 (B).

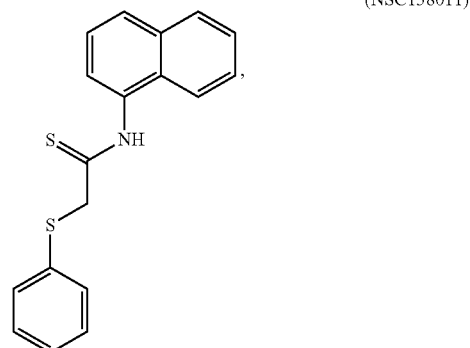

(NSC158011)

TABLE 1

| CpLDH enzyme kinetics on substrates and co-factors. | | | | |
|---|---|---|---|---|
| Parameter | Pyruvate | NADH | Lactate | NAD$^+$ |
| $K_m$ (µM) | 731 (427)* | 734 (92)* | 39,625 (10,830)* | 56 (62)* |
| $V_{max}$ (nmol$^{-1}$ · µg$^{-1}$ · min$^{-1}$) | 5.04 (12.89)* | 6.29 (9.33)* | 0.04 (0.53)* | 0.07 (0.56)* |
| $K_{cat}$ (s$^{-1}$) | 8.42 (16.10)* | 10.50 (11.70)* | 0.07 (0.66)* | 0.11 (0.70)* |
| $K_{cat}$/Km (s$^{-1}$ · M$^{-1}$) | 1.15 × 10$^4$ (3.77 × 10$^4$)* | 1.43 × 10$^4$ (1.27 × 10$^5$)* | 1.73 (61.2)* | 1.97 × 10$^3$ (1.13 × 10$^4$)* |

*Reported by Zhang et al., PLoS Pathog. 2015; 11(11), e1005250.

Figure 2:
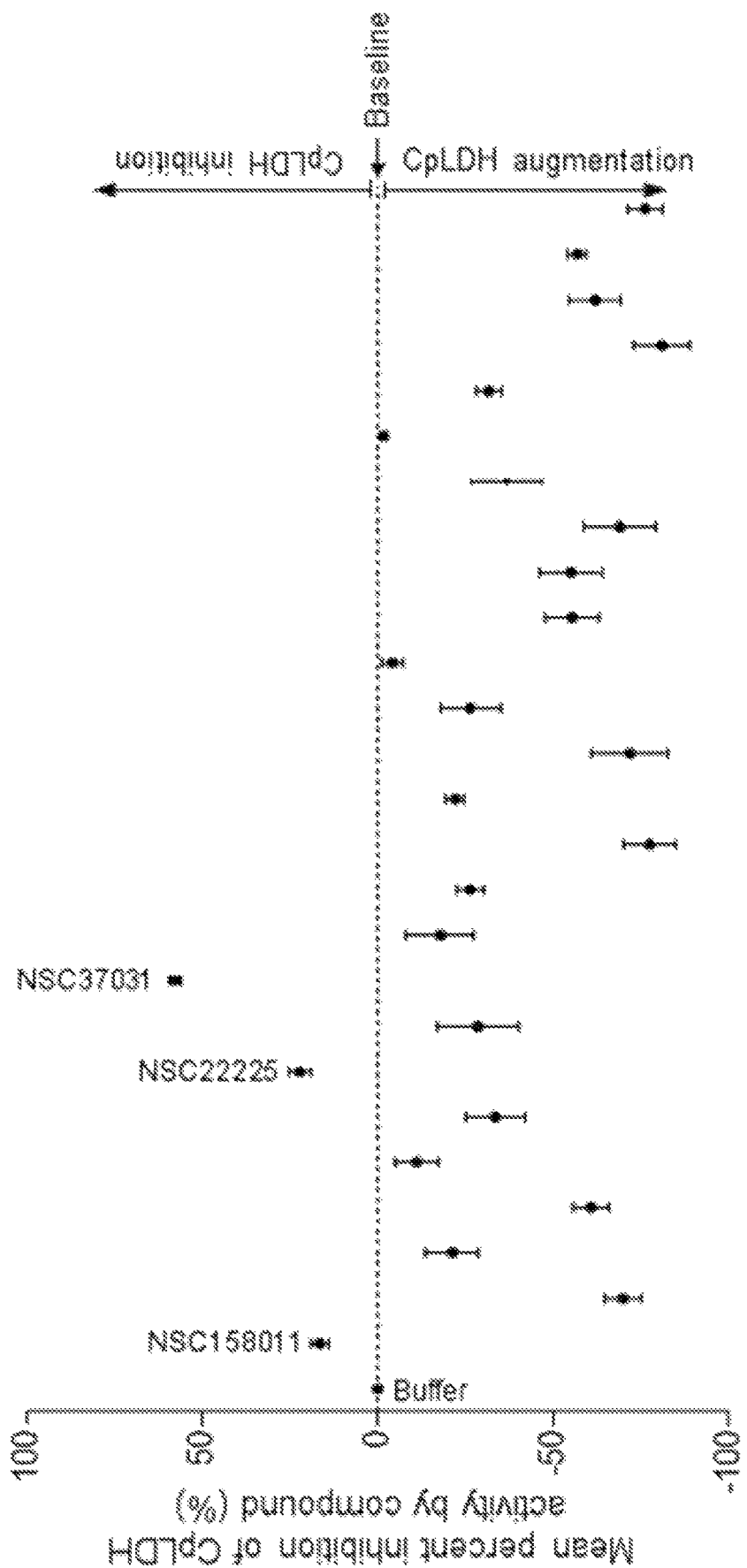
FIG. 2. Effect of the diverse set compounds on the catalytic activity of recombinant CpLDH protein. Individually reconstituted compounds were used at a final concentration of 20 μM in the reaction for the reduction of pyruvate to lactate with recombinant CpLDH protein as enzyme. The mean percent inhibition of CpLDH activity by each compound was derived by dividing the mean change in optical density ($\Delta OD_{340}$) of the reaction after 2 min in the presence of the compound by the mean $\Delta OD_{340}$ of the reaction without compound, and multiplying the product by 100. The baseline mean percent inhibition of 0 (buffer) was for the reaction without compound, but with an equivalent volume of solvent used to reconstitute compound. Compounds with mean percent inhibition values greater than 0 were designated as inhibitors of the activity of CpLDH, while those with mean percent inhibition values less than 0 were classified as augmenters. Each reaction was performed in triplicate, and the data shown represents means of three independent experiments.
Figure 3:
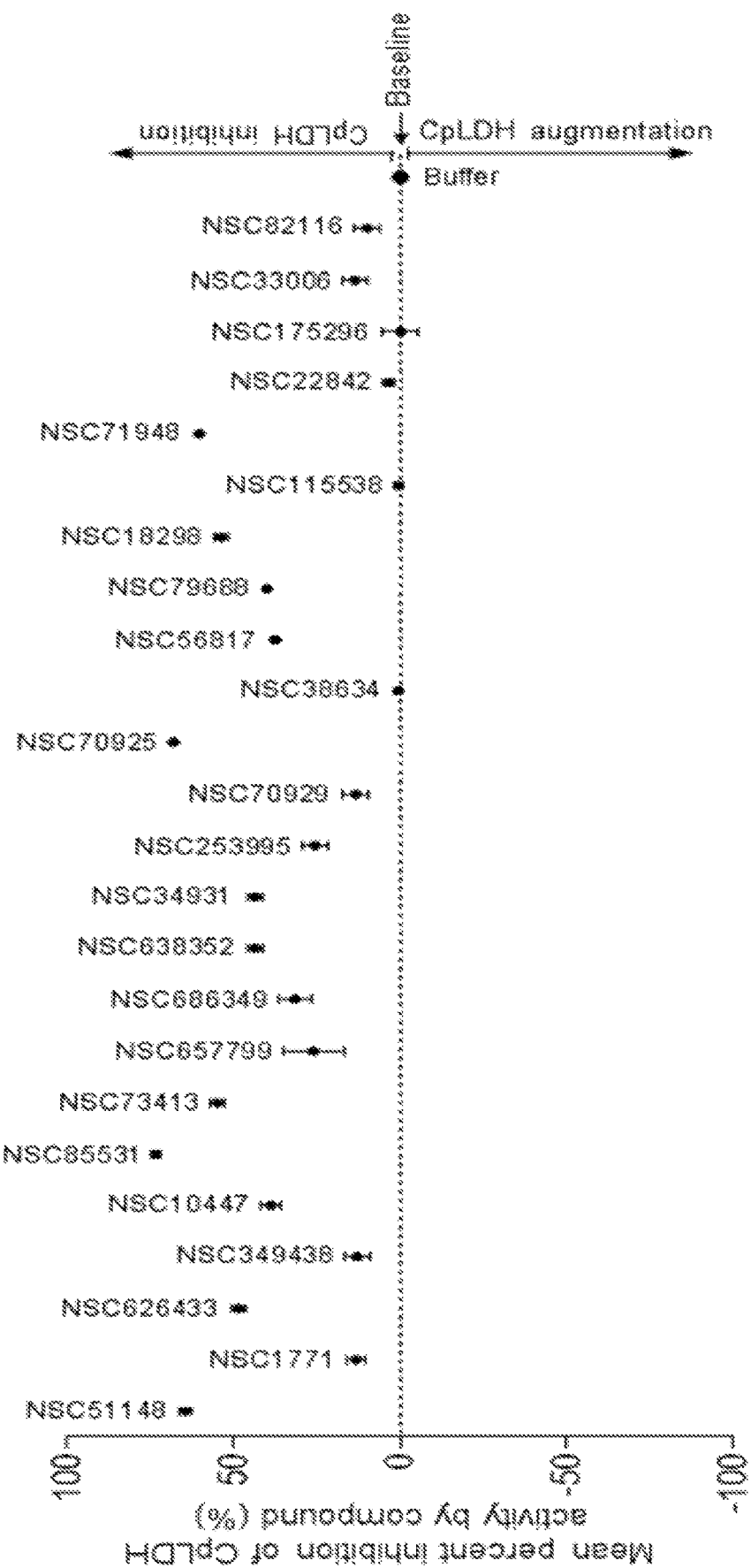
FIG. 3. Effect of the Mechanistic Set IV compounds on the catalytic activity of recombinant CpLDH protein. Individually reconstituted compounds were used at a final concentration of 20 μM in the reaction for the reduction of pyruvate to lactate with recombinant CpLDH protein as enzyme. The mean percent inhibition of CpLDH activity by each compound was derived by dividing the mean change in optical density ($\Delta OD_{340}$) of the reaction after 2 min in the presence of the compound by the mean $\Delta OD_{340}$ of the reaction without compound, and multiplying the product by 100. The baseline mean percent inhibition of 0 (buffer) was for the reaction without compound, but with an equivalent volume of solvent used to reconstitute compound. Compounds with mean percent inhibition values greater than 0 were designated as inhibitors of the activity of CpLDH, while those with mean percent inhibition values less than 0 were classified as augmenters (data points below 0 that are not shown were 765 in total). Each reaction was performed in triplicate, and the data shown represents means of three independent experiments.

In vitro identification of inhibitors for recombinant CpLDH enzyme. We found that recombinant CpLDH had more catalytic activity for the reduction of pyruvate to lactate than for the oxidation of lactate to pyruvate. Therefore, we used the assay for reduction of pyruvate to lactate to screen chemical compounds for inhibitors of the enzymatic activity of recombinant CpLDH in vitro. Within the group of the 27 diverse chemical compounds, we identified three compounds (NSC-22225, NSC-37031 and NSC-158011) that significantly (P<0.05) inhibited the catalytic activity of recombinant CpLDH for the reduction of pyruvate to lactate (FIG. 2). On the other hand, among the 800 compounds in the Mechanistic Set IV, we found 20 that had significant (P<0.05) inhibitory effect on the catalytic activity of recombinant CpLDH (FIG. 3). Those 20 compounds included: NSC51148, NSC1771, NSC626433, NSC349438, NSC10447, NSC85561, NSC73413, NSC657799, NSC686349, NSC638352, NSC34931, NSC253995, NSC70929, NSC70925, NSC56817, NSC79688, NSC18298, NSC71948, NSC22842, NSC33006, and NSC82116. The rest of the compounds either had no effect or augmented the catalytic activity of recombinant CpLDH and were thus not pursued further.

Molecular docking simulations of NSC158011 and NSC10447 binding to CpLDH and human LDH. To deci-

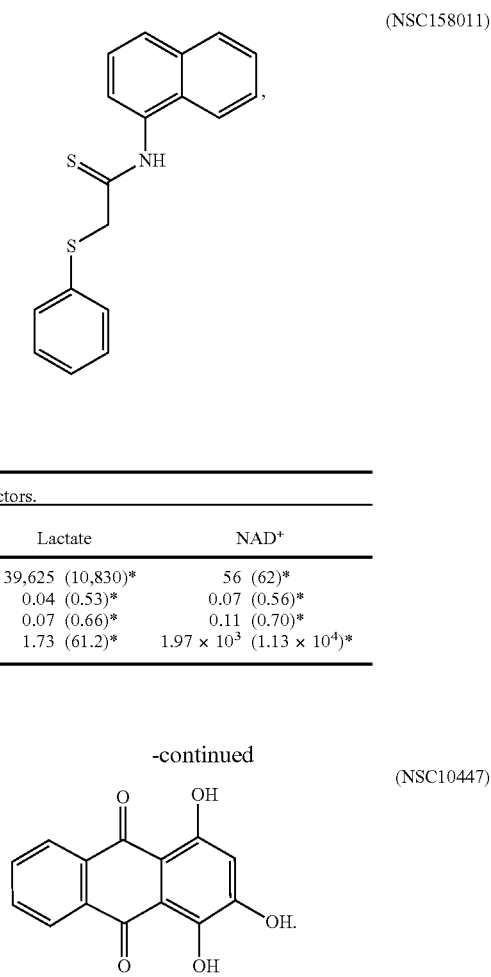

-continued (NSC10447)

Figure 9:
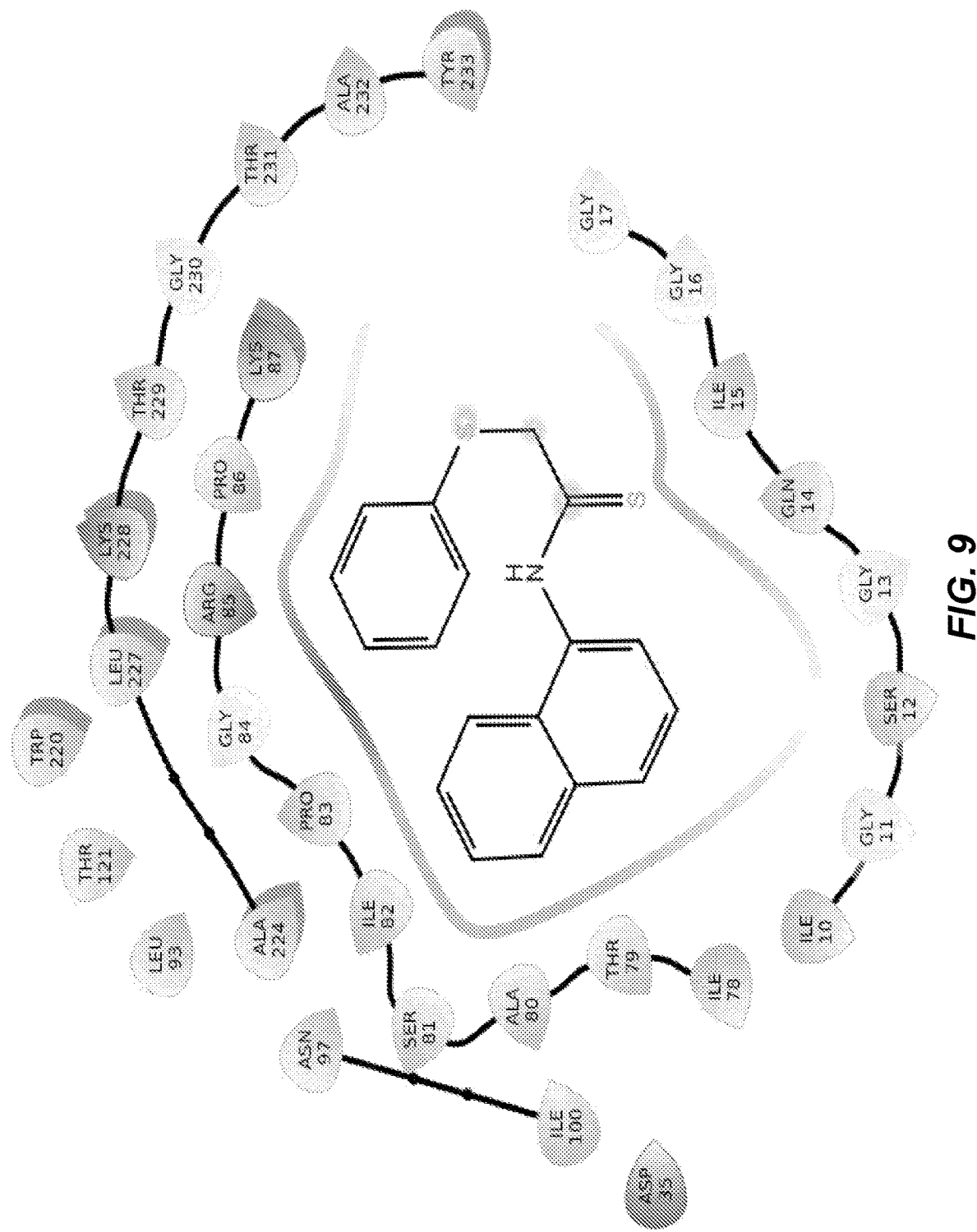
FIG. 9. In silico modeling of the docking of compound NSC158011 to *Cryptosporidium parvum* lactate dehydrogenase protein (CpLDH) showed that the configuration of NSC158011 is in the NADH (co-factor) binding site of CpLDH (4ND2). Hydrogen bonding and hydrophobic residue contacts between docked NSC158011 and CpLDH's NADH-binding site is shown.
Figure 10:
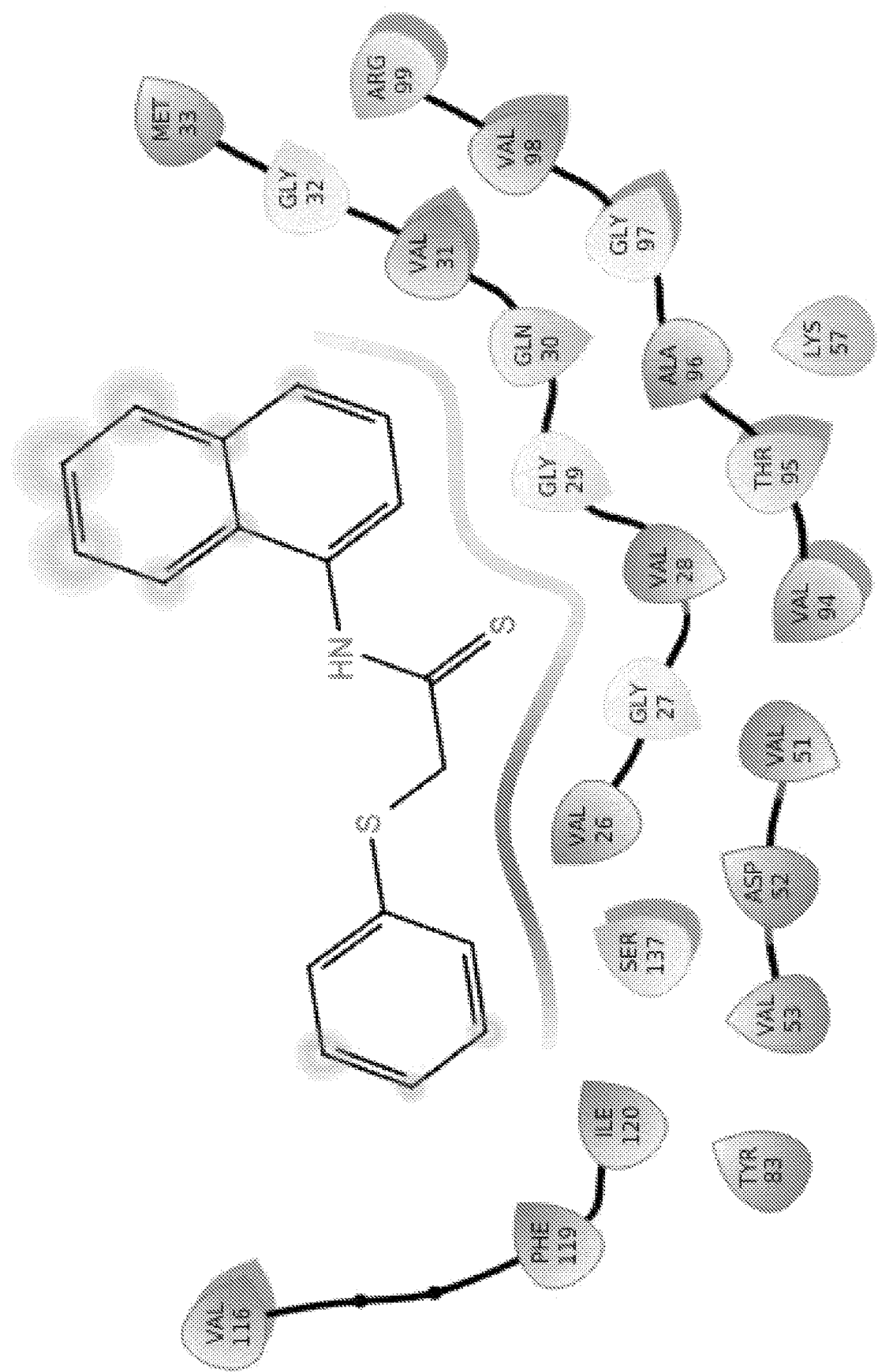
FIG. 10. In silico modeling of the docking of compound NSC158011 to human LDH protein showed that the configuration of NSC158011 is in the NADH (co-factor) binding site of human LDH (1I0Z). Hydrogen bonding and hydrophobic residue contacts between docked NSC158011 and human LDH's NADH-binding site is shown.

NSC158011 complexed with CpLDH with an affinity of −6.4 kcal/mol. (Table 2). The ligand was surrounded in hydrophobic and hydrophilic interactions. Hydrophobic interactions occurred with the Ile-100, Ala-80, and Ile-15 residues and the nonpolar aromatic rings of the molecule, while polar interactions occurred with the Asn-97 and Gln-14 residues and the highly polar thio-amide group (FIG. 9). Although secondary amines do not possess a strong dipole moment, it is possible that the positively-charged Arg-85 residue interacts with the resonance-stabilized deprotonated thio-amide moiety of NSC158011. The docked NSC158011 possessed little solvent exposure, likely due to its folded nature and position, tight within the protein pocket. (FIG. 9). NSC158011 complexed with human LDH with an affinity of −7.2 kcal/mol. (Table 2) The hydrophobic Phe-119, Ile-120, Val-116, Val-98, Ala-96, Val-26, and Val-28 residues interacted with the non-polar aromatic rings of the NSC158011 (FIG. 10). Remarkably, these same non-polar aromatic rings are also heavily solvent-exposed. (FIG. 10).

TABLE 2

Affinity of the most favorable compound poses within lactate dehydrogenase active site.

| Lactate Dehydrogenase | Ligand | Affinity (kcal/mol) | Grid Box size (Å) | Exhaustiveness |
|---|---|---|---|---|
| 4ND2 (CpLDH) | NSC10447 | −7.6 | 40*40*40 | 10 |
| 1I0Z (human LDH) | NSC10447 | −7.1 | 24*14*20 | 10 |
| 4ND2 (CpLDH) | NSC158011 | −6.4 | 40*40*40 | 10 |
| 1I0Z (human LDH) | NSC158011 | −7.2 | 24*14*20 | 10 |

Figure 11:
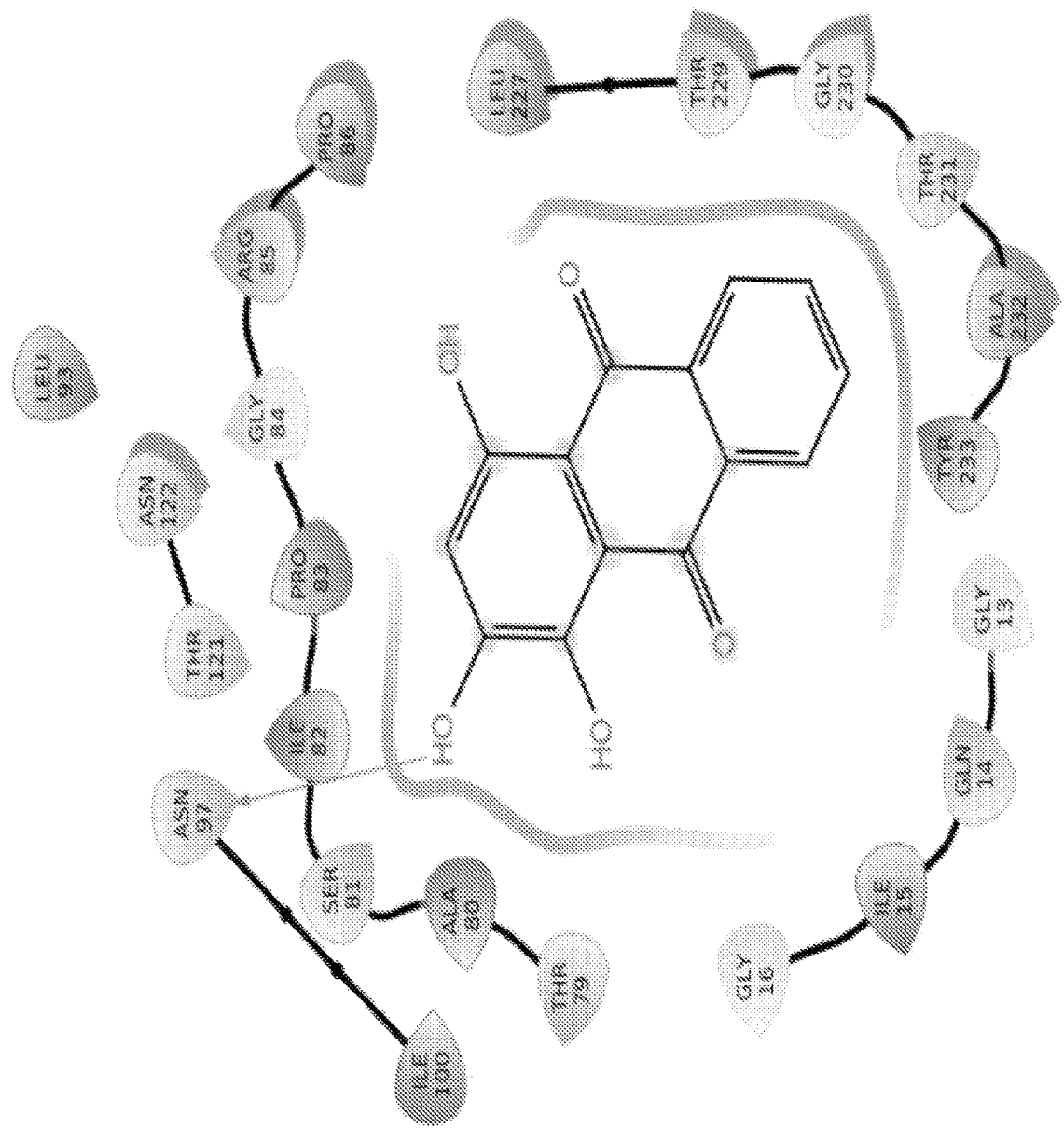
FIG. 11. In silico modeling of the docking of compound NSC10447 to *Cryptosporidium parvum* lactate dehydrogenase protein (CpLDH) showed that the configuration of NSC10447 is in the NADH (co-factor) binding site of CpLDH (4ND2). NSC10447. Hydrogen bonding and hydrophobic residue contacts between docked NSC10447 and CpLDH's NADH-binding site is shown.
Figure 12:
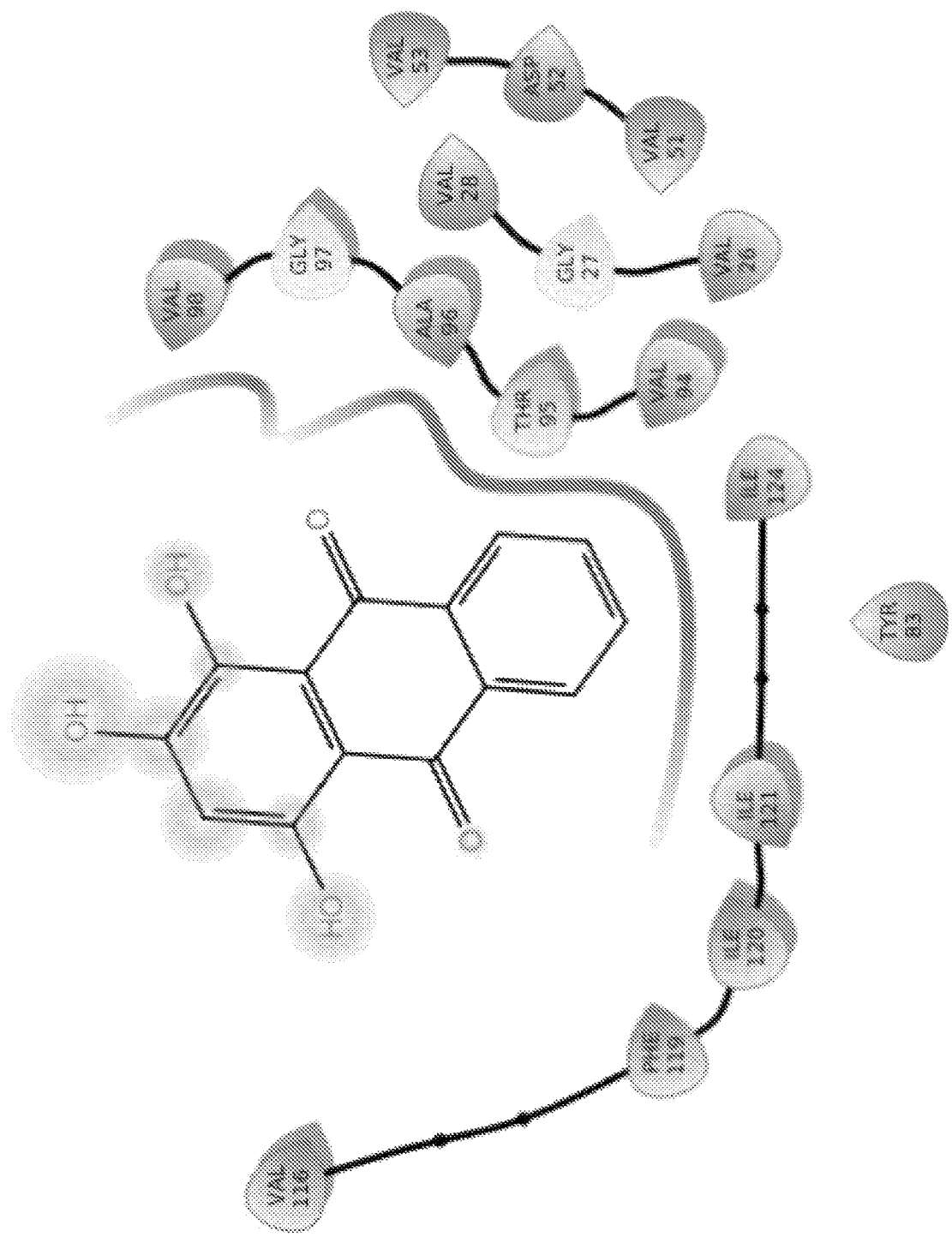
FIG. 12. In silico modeling of the docking of compound NSC10447 to human LDH showed that the configuration of NSC10447 is in the NADH (co-factor) binding site of human LDH (1I0Z). Hydrogen bonding and hydrophobic residue contacts (between docked NSC10447 and human LDH's NADH-binding site is shown.

NSC10447 complexed with CpLDH with an affinity of −7.6 kcal/mol. (Table 2). The ligand was involved primarily in polar interactions with the surrounding Ser81, Thr-79, Thr-229, Thr-231, and positive-charged Arg-85 residues, mediated through interactions with semi-polar carbonyl carbons abundant on one side of the molecule (FIG. 11). The non-polar side of the molecule interacted favorably with the hydrophobic Tyr-233 residue internal to the protein (FIG. 11). There was a weak hydrogen-bonding interaction between the backbone of Asn-97 and an alcohol group on the ligand. Additionally, the hydrophilic carbons had weak but notable solvent exposure. (FIG. 11). NSC10447 complexed with human LDH with an affinity of −7.1 kcal/mol. (Table 2) The ligand was involved primarily in hydrophobic interactions with the surrounding Val-98, Ala-96, Val-94, Phe119, Val-26, Tyr-83, and Val-116 residues that stabilized the non-polar moiety of the molecule (FIG. 12). Interestingly, there was a weak, polar, anti-bonding interaction with the Thr-95 residue. The polar alcohol groups and the attached carbons were heavily solvent exposed in the final docking conformation. (FIG. 12).

The results of the molecular docking simulation showed that due to the high level of interaction between the two lead compounds and the residues within the LDH cofactor-binding pocket, NSC158011 and NSC10447 each bound favorably to both CpLDH and human LDH proteins. It can be proposed that the compounds act as competitive inhibitors for the LDH enzyme, binding favorably to the hydrophobic residues internal to the co-factor-binding pocket and blocking the enzyme from binding NADH, thus preventing the hydride transfer that powers the conversion of pyruvate to lactate.

Figure 4:
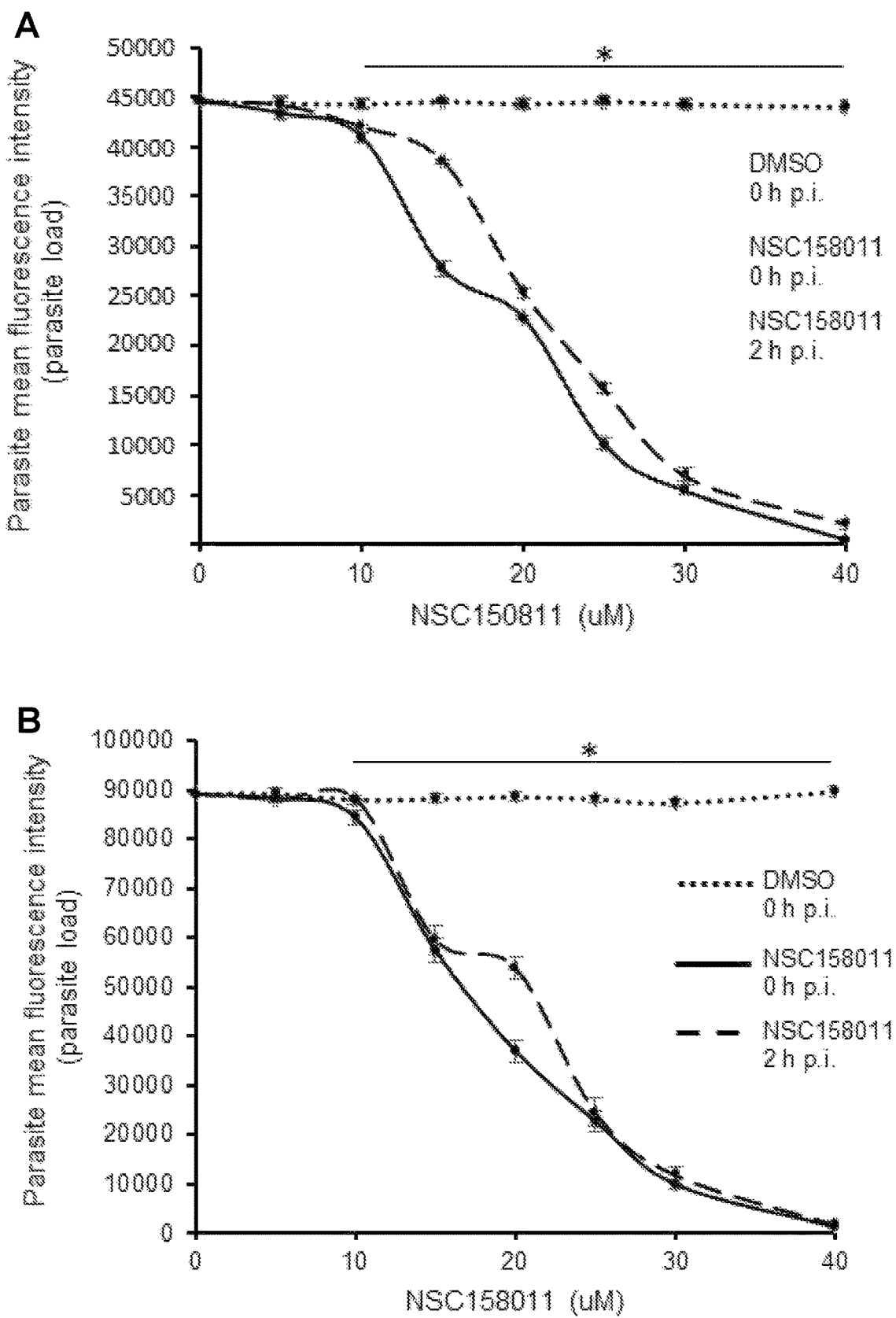
FIG. 4. Analysis of the effect of varying concentrations of compound NSC158011 on the growth of *Cryptosporidium parvum* in HCT-8 cells. Equal amounts of freshly excysted sporozoites of *C. parvum* were inoculated into HCT-8 cells in culture and varying concentrations of NSC158011 added at the time of infection (solid line) or added 2 h post-infection (p.i.) (dashed line). Control infected cells (dotted line) were treated immediately p.i. with volumes of DMSO equivalent to those used in the compound-treated cultures. The cells were analyzed for parasite infectivity and proliferation by an immunofluorescence assay after (A) 48 h, and (B) 72 h of culture. The fluorescence generated by intracellular *C. parvum* merozoites was quantified and is shown on the Y-axis representing the parasite load. The data shown represent means of three independent experiments with standard error bars and levels of statistical significance between groups indicated by asterisk (*, P<0.05).

NSC158011 and NSC10447 inhibit *C. parvum* growth in vitro. All the compounds that we found to have inhibitory effect against recombinant CpLDH activity were first analyzed for in vitro cytotoxicity in a mammalian cell line, HCT-8 (American Type Culture Collection Item number: CCL244) before testing their anti-*Cryptosporidium* efficacy. For cytotoxicity screening, varying concentrations of each compound (from 0 to 700 μM) were tested in triplicate using the WST-1 cell proliferation assay and the half maximal inhibitory concentration (cytotoxicity $IC_{50}$ values) of the compounds in HCT-8 cells (Table 7) were derived from dose-response curves using GraphPad PRISM software. To test the compounds' efficacy against *C. parvum* in vitro, an initial screen was performed using concentrations that were at least 50% lower than the compounds' respective cytotoxicity $IC_{50}$ values (Table 7). NSC10447 and NSC158011 from the diverse group and Mechanistic Set IV group, respectively, were found to significantly ($P<0.05$) inhibit *C. parvum* proliferation in vitro at 48 h post-infection. Therefore, these two compounds were selected for secondary analysis of anti-*Cryptosporidium* efficacy using varying concentrations and durations of culture to derive the $IC_{50}$ values for the inhibition of parasite proliferation. For each compound, the assays were done in two formats: (1) by adding the compound to the HCT-8 cells culture shortly before infecting them with *C. parvum* sporozoites, with the goal to assess whether the compounds would block host cell invasion by sporozoites, and (2) by adding the compounds to the cells 2 h post-infection to determine the effect of the compounds on intracellular parasites. When the cultures were analyzed at 48 h post-infection, compound NSC158011 was found to have a significant ($P<0.05$) concentration-dependent effect of inhibiting proliferation of intracellular *C. parvum* merozoites in HCT-8 cells starting at 10 μM (with 40 μM blocking parasite growth almost completely) relative to the control infected cultures without compound treatment (FIG. 4A). Treating the cultures with NSC158011 compound 2 h post-infection also resulted in a concentration-dependent reduction in parasite proliferation, but with a slight decrease in compound efficacy relative to treating at the time of infection (FIG. 4A). By using GraphPad PRISM software, the half maximal inhibitory concentration ($IC_{50}$) values of NSC158011 for *C. parvum* in vitro were derived from the dose-response curves. The NSC158011 $IC_{50}$ values at 48 h post-infection for inhibition of *C. parvum* growth when compound was added immediately, or 2 h after infecting the HCT-8 cells were 14.88 and 15.81 respectively. Analysis of the inhibitory effect of NSC158011 on parasite proliferation at 72 h post-infection, depicted similar concentration-dependent effects (FIG. 4B), with $IC_{50}$ values of 15.63 and 16.50 μM when compound was added immediately or 2 h post-infection, respectively. After infecting HCT-8 cells, *C. parvum* is able to proliferate for 3-4 days before becoming growth-arrested. Therefore, during both observation time-points of 48 h and 72 h post-infection, *C. parvum* if untreated was expected to be in proliferative phase. Consistently, in the untreated infected cells, the relative parasite load at 72 h post-infection was about 2-fold that observed at 48 h post-infection (FIG. 4A and FIG. 4B).

Figure 5:
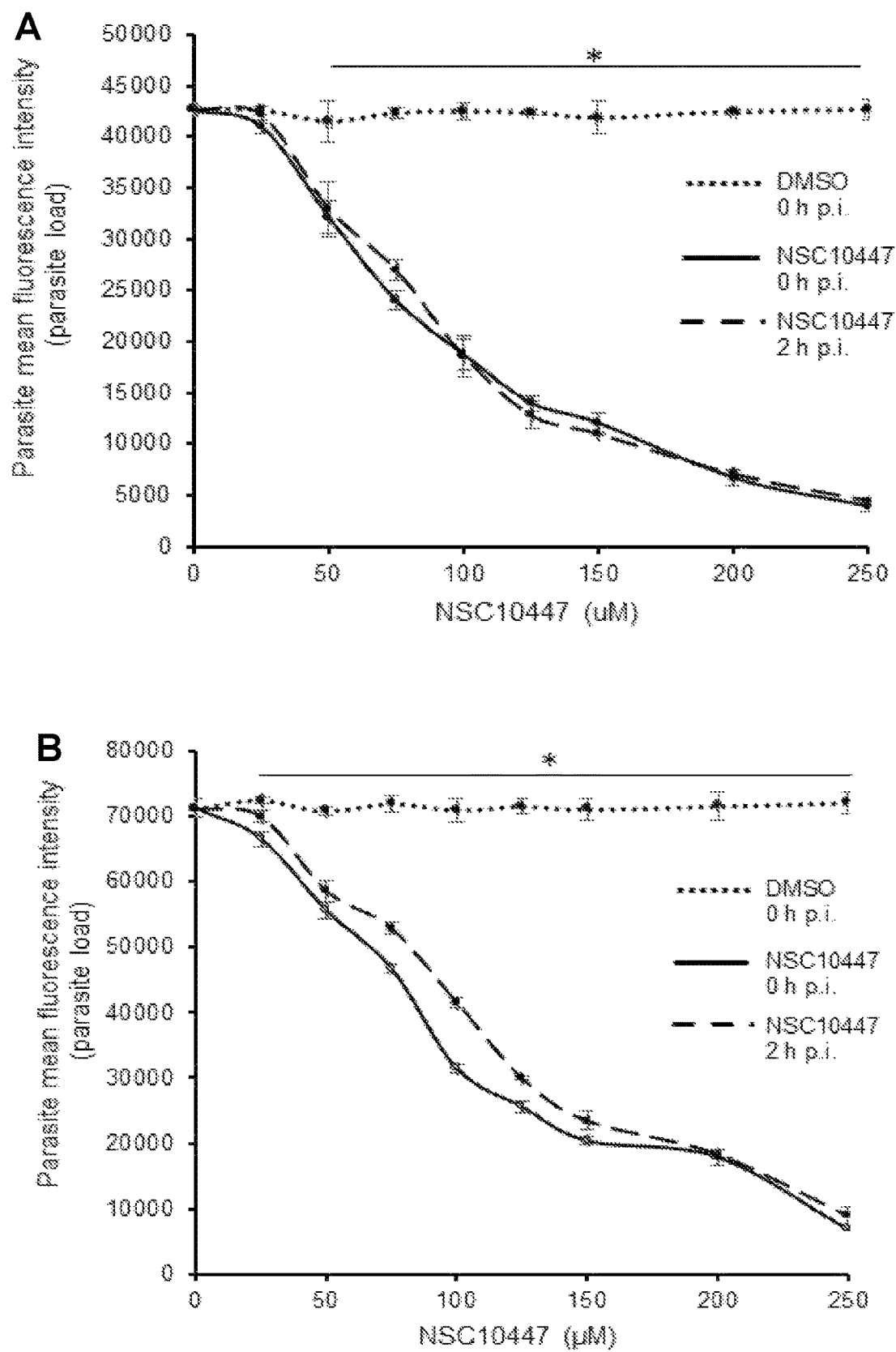
FIG. 5. Analysis of the effect of varying concentrations of compound NSC10447 on the growth of *Cryptosporidium parvum* in HCT-8 cells. Equal amounts of freshly excysted sporozoites of *C. parvum* were inoculated into HCT-8 cells in culture and varying concentrations of NSC10447 added at the time of infection (solid line) or added 2 h post-infection (p.i.) (dashed line). Control infected cells (dotted line) were treated immediately p.i. with volumes of DMSO equivalent to those used in the compound-treated cultures. The cultures were analyzed for parasite infectivity and proliferation by an immunofluorescence assay after (A) 48 h, and (B) 72 h of culture. The fluorescence generated by intracellular *C. parvum* merozoites was quantified and is shown on the Y-axis representing the parasite load. The data shown represent means of three independent experiments with standard error bars and levels of statistical significance between groups indicated by asterisk (*, P<0.05).

Compound NSC10447 also depicted a concentration-dependent inhibitory effect on parasite growth, both at 48 h (FIG. 5A) and 72 h (FIG. 5B) time points of observation. The efficacy of NSC10447 when added immediately or 2 h after infecting the cells was similar (FIG. 5A). The NSC10447 $IC_{50}$ values at 48 h post-infection for inhibition of *C. parvum* growth when compound was added immediately, and 2 h after infecting the HCT-8 cells were 72.65 and 79.52 respectively. Consistently, NSC10447 had a concentration-dependent inhibitory effect on parasite growth at 72 h time point of observation (FIG. 5B), with $IC_{50}$ values of 83.63 and 95.17 when the compound was added immediately, and 2 h after infecting the HCT-8 cells, respectively. Noteworthy, in all instances, NSC158011 depicted significantly higher in vitro efficacy against *C. parvum* than NSC10447 (Table 3). The $IC_{50}$ values of NSC158011 and NSC10447 for the inhibition of the catalytic activity of recombinant CpLDH in vitro were 76.59 μM and 46.33 respectively (Table 3).

TABLE 3

NSC158011 and NSC10447 IC$_{50}$ values on CpLDH enzyme and *C. parvum*.

| Parameter | NSC158011 (µM) | NSC10447 (µM) |
|---|---|---|
| Inhibition of recombinant CpLDH activity | 76.59 | 46.33 |
| Inhibition of *C. parvum* growth at 48 h p.i. | 14.88 | 72.65 |
| Inhibition of *C. parvum* growth at 48 h p.i. (2 h)* | 15.81 | 79.52 |
| Inhibition of *C. parvum* growth at 72 h p.i. | 15.63 | 83.63 |
| Inhibition of *C. parvum* growth at 72 h p.i. (2 h)* | 16.50 | 95.17 |

*Compounds were added to culture 2 h post-infection (p.i.)

Figure 6:
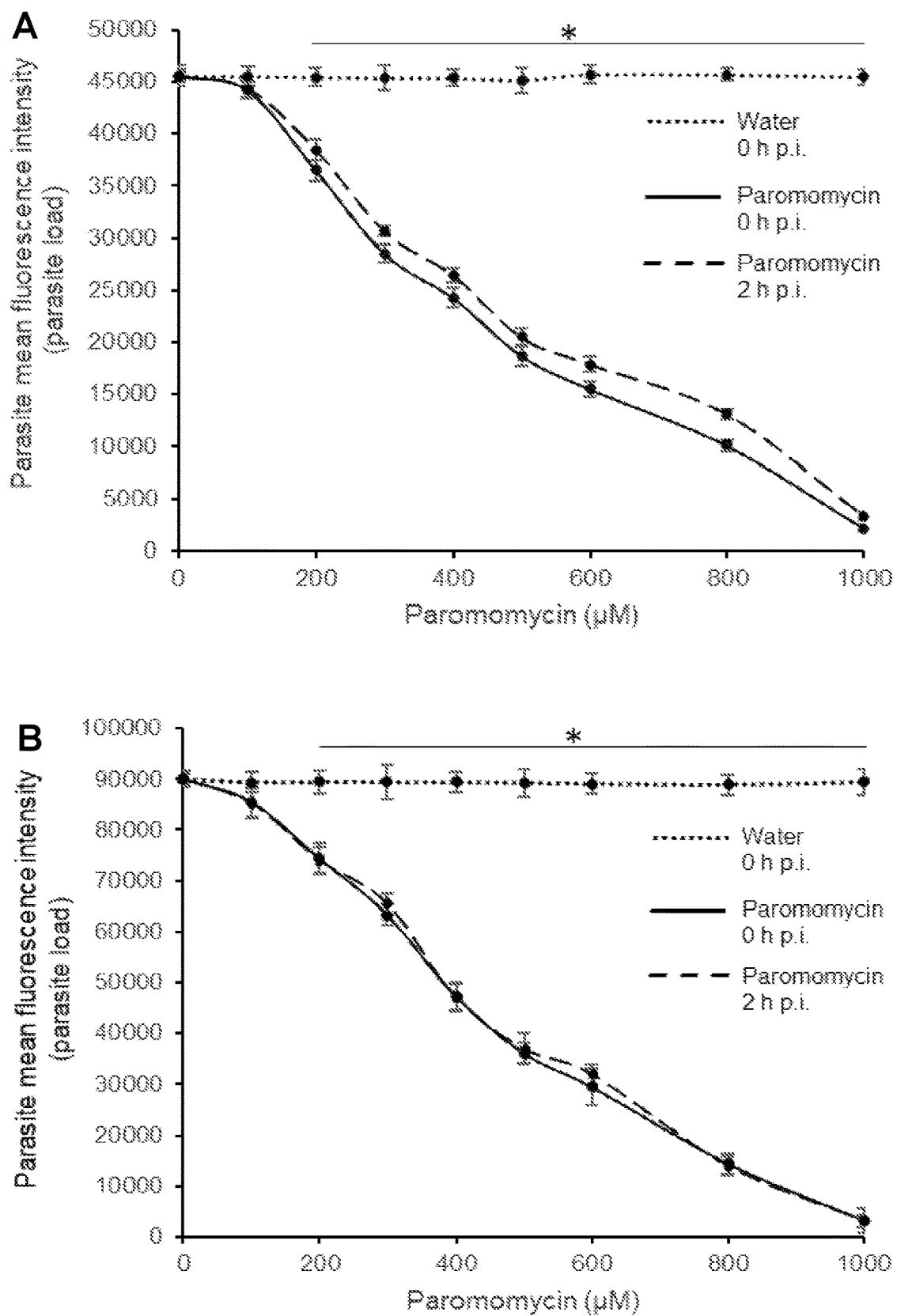
FIG. 6. Analysis of the effect of varying concentrations of paromomycin on the growth of *Cryptosporidium parvum* in HCT-8 cells. Equal amounts of freshly excysted sporozoites of *C. parvum* were inoculated into HCT-8 cells in culture and varying concentrations of paromomycin dissolved in sterile distilled water was added at infection (solid line) or 2 h post-infection (p.i.) (dashed line). Control infected cells (dotted line) were treated immediately p.i. with volumes of sterile distilled water equivalent to those used in the paromomycin-treated cultures. The cultures were analyzed for parasite infectivity and proliferation by an immunofluorescence assay after (A) 48 h, and (B) 72 h of culture. The fluorescence generated by intracellular *C. parvum* merozoites was quantified and is shown on the Y-axis representing the parasite load. The data shown represent means of three independent experiments with standard error bars and levels of statistical significance between groups indicated by asterisk (*, P<0.05).

We used paromomycin as the positive control treatment. Using in vitro assays the cytotoxicity of paromomycin in HCT-8 cells has been reported to be negligible even when used at concentrations above 1000 µM. Therefore, we tested the in vitro efficacy of paromomycin against *C. parvum* at varying concentrations up to a maximum of 1000 and found it to have a concentration-dependent effect of inhibiting *C. parvum* growth in vitro, both at 48 h (FIG. 6A) and 72 h (FIG. 6B) post-infection, with IC$_{50}$ values of 450 and 400 respectively. Others have previously reported paromomycin to have an IC$_{50}$ of 711 µM for inhibition of *C. parvum* growth in HCT-8 cells. There was no notable significant difference in paromomycin inhibitory effect against *C. parvum* between starting the treatment immediately or 2 h after infection of the HCT-8 cells.

NSC158011 and NSC10447 possess in vivo efficacy against *C. parvum*. Compound NSC158011 and NSC10447 that were found to inhibit *C. parvum* growth in vitro were selected for in vivo testing using a mouse infection model. Prior to use in mice, the highest tolerable doses in mice for the two compounds were found to be 400 mg/kg and 1000 mg/kg for NSC158011 and NSC10447, respectively. These doses consistently did not induce any toxicity signs (changes from normal physical activity, respiration, body temperature, feeding pattern, body posture, fur condition or occurrence of death) over 7 days of daily oral gavage in mice. In the case of NSC158011, the dose of 400 mg/kg intraperitoneal administration in mice has also been previously shown not to be toxic to mice. Thus, the doses of 400 mg/kg and 1000 mg/kg were selected as the highest doses for testing the efficacy of NSC158011 and NSC10447, respectively, against *C. parvum* growth and proliferation in mice. Paromomycin at 100 mg/kg daily by oral gavage was used as a positive control. The daily load of *C. parvum* oocysts shed in mice feces was determined using real time PCR quantification of the *C. parvum* 18s rRNA gene. As expected, in the feces of untreated infected mice, *C. parvum* genomic DNA was almost undetectable during the first 2 days post-infection, but was detectable from 3 days post-infection, and increased progressively with increase in the number of days post-infection (Table 4-6). The notable lower *C. parvum* DNA in the feces of the untreated infected mice in Table 6 when compared to those for Table 4 and Table 5 is because the infection assays for Table 3 and Table 4 were done using freshly purified oocysts, while those for Table 6 were done using oocysts that were purified 3 months earlier, and thus their infectivity could have been lower. We found that NSC158011 at 400 mg/kg significantly (P<0.05) reduced shedding of *C. parvum* oocysts in mice feces, comparable to the efficacy of paromomycin (Table 4).

TABLE 4

Real-time PCR quantification of *C. parvum* DNA in fecal samples of treated or untreated infected mice.

| DPI* | Infected untreated mice fecal *C. parvum* DNA load (ng/µL) | Infected NSC158011 (400 mg/kg) treated mice fecal *C. parvum* DNA load (ng/µL) | Infected paromomycin (100 mg/kg) treated mice fecal *C. parvum* DNA load (ng/µL) | Uninfected mice fecal *C. parvum* DNA load (ng/µL) |
|---|---|---|---|---|
| 1 | $1.3 \pm 0.8$ (×10$^{-11}$) | $2.9 \pm 1.7$ (×10$^{-10}$) | $9.6 \pm 4.4$ (×10$^{-11}$) | 0.0 |
| 2 | $4.2 \pm 0.2$ (×10$^{-10}$) | $4.8 \pm 0.3$ (×10$^{-10}$) | $4.5 \pm 3.1$ (×10$^{-9}$) | 0.0 |
| 3 | $6.1 \pm 0.1$ (×10$^{-8}$) | $8.8 \pm 0.8$ (×10$^{-9}$) | $1.8 \pm 0.9$ (×10$^{-9}$) | 0.0 |
| 4 | $8.5 \pm 0.5$ (×10$^{-7}$) | $5.3 \pm 0.4$ (×10$^{-8}$) | $4.3 \pm 0.1$ (×10$^{-8}$) | 0.0 |
| 5 | $6.5 \pm 1.2$ (×10$^{-5}$) | $2.2 \pm 0.08$ (×10$^{-7}$) | $2.3 \pm 0.8$ (×10$^{-7}$) | 0.0 |
| 6 | $1.4 \pm 0.3$ (×10$^{-4}$) | $2.4 \pm 0.1$ (×10$^{-6}$) | $4.3 \pm 0.1$ (×10$^{-6}$) | 0.0 |
| 7 | $7.5 \pm 1.3$ (×10$^{-3}$) | $2.3 \pm 0.1$ (×10$^{-6}$) | $3.5 \pm 0.5$ (×10$^{-6}$) | 0.0 |
| 8 | $5.3 \pm 0.9$ (×10$^{-3}$) | $1.6 \pm 0.1$ (×10$^{-6}$) | $2.4 \pm 0.1$ (×10$^{-6}$) | 0.0 |

*Days post-infection with *C. parvum*

As expected, *C. parvum* DNA was consistently undetectable at all time points sampled in the uninfected mice (Table 4). By day 7 post-infection, both NSC158011 and paromomycin treatment had reduced the shedding of *C. parvum* in mice feces by about 3000-fold when compared to the untreated infected mice samples (Table 4). This suggested that NSC158011, at 400 mg/kg, had sustained anti-*Cryptosporidium* efficacy in vivo comparable to that of 100 mg/kg of paromomycin. We titrated the dose of NSC158011 to determine the effect of lower dosages. We observed a dose-dependent reduction in efficacy of NSC158011, with 200 mg/kg having about 10-fold lower efficacy than paromomycin during the last three days of treatment. Consistently, 100 mg/kg of NSC158011 showed lower efficacy than 200 mg/kg NSC158011 (Table 5).

TABLE 5

Real-time PCR quantification of *C. parvum* DNA in fecal samples of treated or untreated infected mice.

| DPI* | Infected untreated mice fecal *C. parvum* DNA load (ng/μL) | Infected NSC158011 (100 mg/kg) treated mice fecal *C. parvum* DNA load (ng/μL) | Infected NSC158011 (200 mg/kg) treated mice fecal *C. parvum* DNA load (ng/μL) | Infected paromomycin (100 mg/kg) treated mice fecal *C. parvum* DNA load (ng/μL) | Uninfected mice fecal *C. parvum* DNA load (ng/μL) |
|---|---|---|---|---|---|
| 1 | $1.5 \pm 0.2 \ (\times 10^{-9})$ | $1.5 \pm 0.2 \ (\times 10^{-9})$ | $1.2 \pm 0.2 \ (\times 10^{-9})$ | $1.2 \pm 0.3 \ (\times 10^{-9})$ | 0.0 |
| 2 | $4.6 \pm 0.1 \ (\times 10^{-8})$ | $1.8 \pm 0.4 \ (\times 10^{-8})$ | $1.3 \pm 0.4 \ (\times 10^{-8})$ | $1.1 \pm 0.3 \ (\times 10^{-8})$ | 0.0 |
| 3 | $5.8 \pm 0.2 \ (\times 10^{-7})$ | $2.3 \pm 0.4 \ (\times 10^{-7})$ | $1.7 \pm 0.2 \ (\times 10^{-7})$ | $2.3 \pm 0.2 \ (\times 10^{-7})$ | 0.0 |
| 4 | $6.2 \pm 0.2 \ (\times 10^{-5})$ | $3.4 \pm 0.1 \ (\times 10^{-6})$ | $2.9 \pm 0.1 \ (\times 10^{-6})$ | $3.3 \pm 0.1 \ (\times 10^{-6})$ | 0.0 |
| 5 | $1.7 \pm 0.1 \ (\times 10^{-4})$ | $9.8 \pm 0.3 \ (\times 10^{-5})$ | $8.0 \pm 0.3 \ (\times 10^{-5})$ | $9.2 \pm 0.3 \ (\times 10^{-6})$ | 0.0 |
| 6 | $4.2 \pm 0.1 \ (\times 10^{-3})$ | $3.1 \pm 0.2 \ (\times 10^{-5})$ | $2.0 \pm 0.1 \ (\times 10^{-5})$ | $2.1 \pm 0.1 \ (\times 10^{-6})$ | 0.0 |
| 7 | $2.0 \pm 0.3 \ (\times 10^{-3})$ | $8.0 \pm 0.1 \ (\times 10^{-5})$ | $4.0 \pm 0.1 \ (\times 10^{-5})$ | $6.4 \pm 0.1 \ (\times 10^{-6})$ | 0.0 |
| 8 | $6.3 \pm 0.4 \ (\times 10^{-3})$ | $4.1 \pm 0.1 \ (\times 10^{-5})$ | $1.5 \pm 0.1 \ (\times 10^{-5})$ | $2.7 \pm 0.1 \ (\times 10^{-6})$ | 0.0 |

*Days post-infection with *C. parvum*

For testing the in vivo anti-*Cryptosporidium* efficacy of NSC10447, in addition to testing the highest tolerable dose of 1000 mg/kg, we also tested lower doses of 250 mg/kg and 500 mg/kg. While the *C. parvum* DNA was undetectable in the uninfected mice's feces, the untreated infected mice had readily detectable *C. parvum* DNA by day 3 post-infection, that then increased progressively with increase in number of days post-infection (Table 6).

TABLE 6

Real-time PCR quantification of *C. parvum* DNA in fecal samples of treated or untreated infected mice.

| DPI* | Infected untreated mice fecal *C. parvum* DNA load (ng/μL) | Infected NSC10447 (250 mg/kg) treated mice fecal *C. parvum* DNA load (ng/μL) | Infected NSC10447 (500 mg/kg) treated mice fecal *C. parvum* DNA load (ng/μL) | Infected NSC10447 (1000 mg/kg) treated mice fecal *C. parvum* DNA load (ng/μL) | Infected paromomycin (100 mg/kg) treated mice fecal *C. parvum* DNA load (ng/μL) | Uninfected mice fecal *C. parvum* DNA load (ng/μL) |
|---|---|---|---|---|---|---|
| 1 | $4.0 \pm 0.1 \ (\times 10^{-10})$ | $4.4 \pm 0.5 \ (\times 10^{-10})$ | $1.0 \pm 0.5 \ (\times 10^{-10})$ | $1.2 \pm 0.2 \ (\times 10^{-9})$ | $3.1 \pm 0.2 \ (\times 10^{-10})$ | 0.0 |
| 2 | $6.1 \pm 0.2 \ (\times 10^{-9})$ | $7.3 \pm 0.2 \ (\times 10^{-10})$ | $9.4 \pm 0.2 \ (\times 10^{-10})$ | $3.0 \pm 0.7 \ (\times 10^{-9})$ | $6.6 \pm 0.5 \ (\times 10^{-9})$ | 0.0 |
| 3 | $2.5 \pm 0.1 \ (\times 10^{-8})$ | $1.0 \pm 0.1 \ (\times 10^{-8})$ | $6.7 \pm 0.6 \ (\times 10^{-9})$ | $6.4 \pm 0.2 \ (\times 10^{-9})$ | $5.2 \pm 0.3 \ (\times 10^{-9})$ | 0.0 |
| 4 | $2.5 \pm 0.2 \ (\times 10^{-7})$ | $1.2 \pm 0.1 \ (\times 10^{-7})$ | $1.4 \pm 0.1 \ (\times 10^{-7})$ | $1.1 \pm 0.1 \ (\times 10^{-7})$ | $4.7 \pm 0.2 \ (\times 10^{-8})$ | 0.0 |
| 5 | $3.1 \pm 0.7 \ (\times 10^{-6})$ | $1.2 \pm 0.1 \ (\times 10^{-6})$ | $1.6 \pm 0.1 \ (\times 10^{-6})$ | $1.3 \pm 0.1 \ (\times 10^{-6})$ | $5.0 \pm 0.6 \ (\times 10^{-7})$ | 0.0 |
| 6 | $1.2 \pm 0.2 \ (\times 10^{-5})$ | $4.8 \pm 0.2 \ (\times 10^{-6})$ | $5.9 \pm 0.4 \ (\times 10^{-6})$ | $5.6 \pm 0.4 \ (\times 10^{-6})$ | $4.8 \pm 0.1 \ (\times 10^{-6})$ | 0.0 |
| 7 | $2.7 \pm 0.8 \ (\times 10^{-4})$ | $1.9 \pm 0.2 \ (\times 10^{-5})$ | $9.3 \pm 0.2 \ (\times 10^{-6})$ | $6.3 \pm 0.4 \ (\times 10^{-6})$ | $5.1 \pm 0.8 \ (\times 10^{-6})$ | 0.0 |
| 8 | $1.7 \pm 0.9 \ (\times 10^{-3})$ | $4.7 \pm 0.1 \ (\times 10^{-5})$ | $3.0 \pm 0.4 \ (\times 10^{-5})$ | $1.2 \pm 0.8 \ (\times 10^{-6})$ | $5.4 \pm 0.1 \ (\times 10^{-6})$ | 0.0 |

*Days post-infection with *C. parvum*

From day 3 until day 8 of treatment, compared to the infected untreated, mice treated with NSC10447 at 250, 500 and 1000 mg/kg showed sustained significantly lower (by at least 50%) *C. parvum* DNA load in their feces (Table 6). There was a notable dose-dependent effect, with 1000 mg/kg having the highest efficacy (Table 6). Notably, on day 7 and 8 post-infection, the 1000 mg/kg dose of NSC10447 maintained anti-*Cryptosporidium* efficacy that was comparable to that of paromomycin, while both 250 and 500 mg/kg doses depicted lower efficacies than paromomycin (Table 6).

Figure 7:
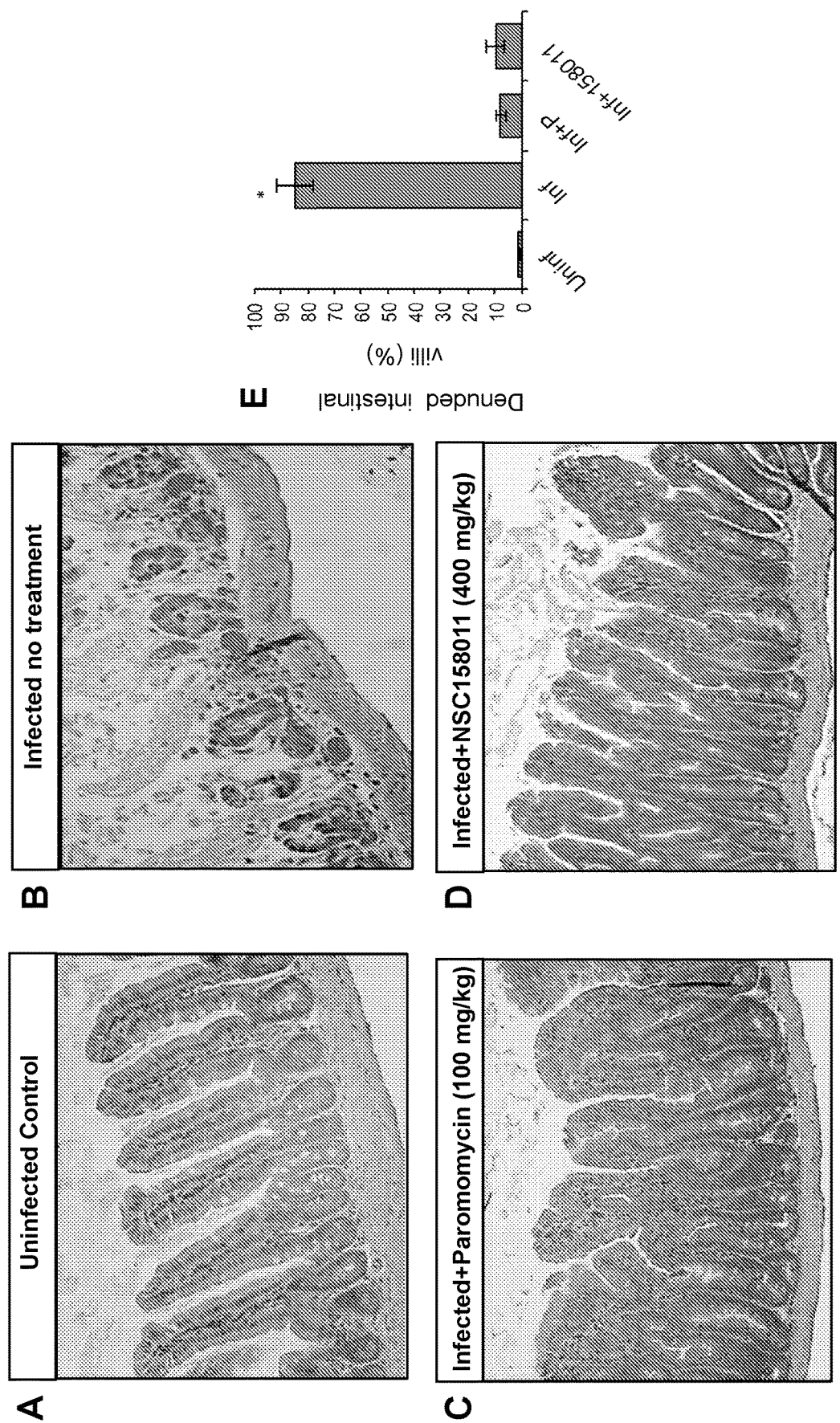
FIG. 7. Histopathological analysis of the effect of *Cryptosporidium parvum* infection in the lower small intestines of mice with or without NSC158011 treatment. Mice infected with *C. parvum* were maintained untreated (Infected no treatment), treated with paromocycin (Infected+Paromomycin (100 mg/kg)) or treated with compound NSC158011 at 400 mg/kg (Infected+NSC158011 (400 mg/kg)) for 8 days. Uninfected mice were maintained as control (Uninfected Control). After 8 days, mice were sacrificed, and the lower intestinal tissue processed for histology and stained with hematoxylin and eosin. (A) Uninfected control mice samples depicted intact intestinal epithelium with prominent villi. (B) In contrast, infected mice without treatment depicted denuded villi. Both (C) paromomycin and (D) NSC158011 treated infected mice depicted intact intestinal epithelium with prominent villi that were comparable to the uninfected control. The images are representative of samples analyzed from 3 mice per treatment group. (E) The mean percentage of denuded intestinal villi in 4 randomly chosen microscopic fields per sample from the uninfected (Uninf), infected untreated (Inf), Infected treated with paromomycin (Inf+P), and infected treated with 400 mg/kg NSC150811 (Inf+150811) mice. The data shown represent means for samples from three mice per group with standard error bars and levels of statistical significance depicted (*P<0.05).
Figure 8:
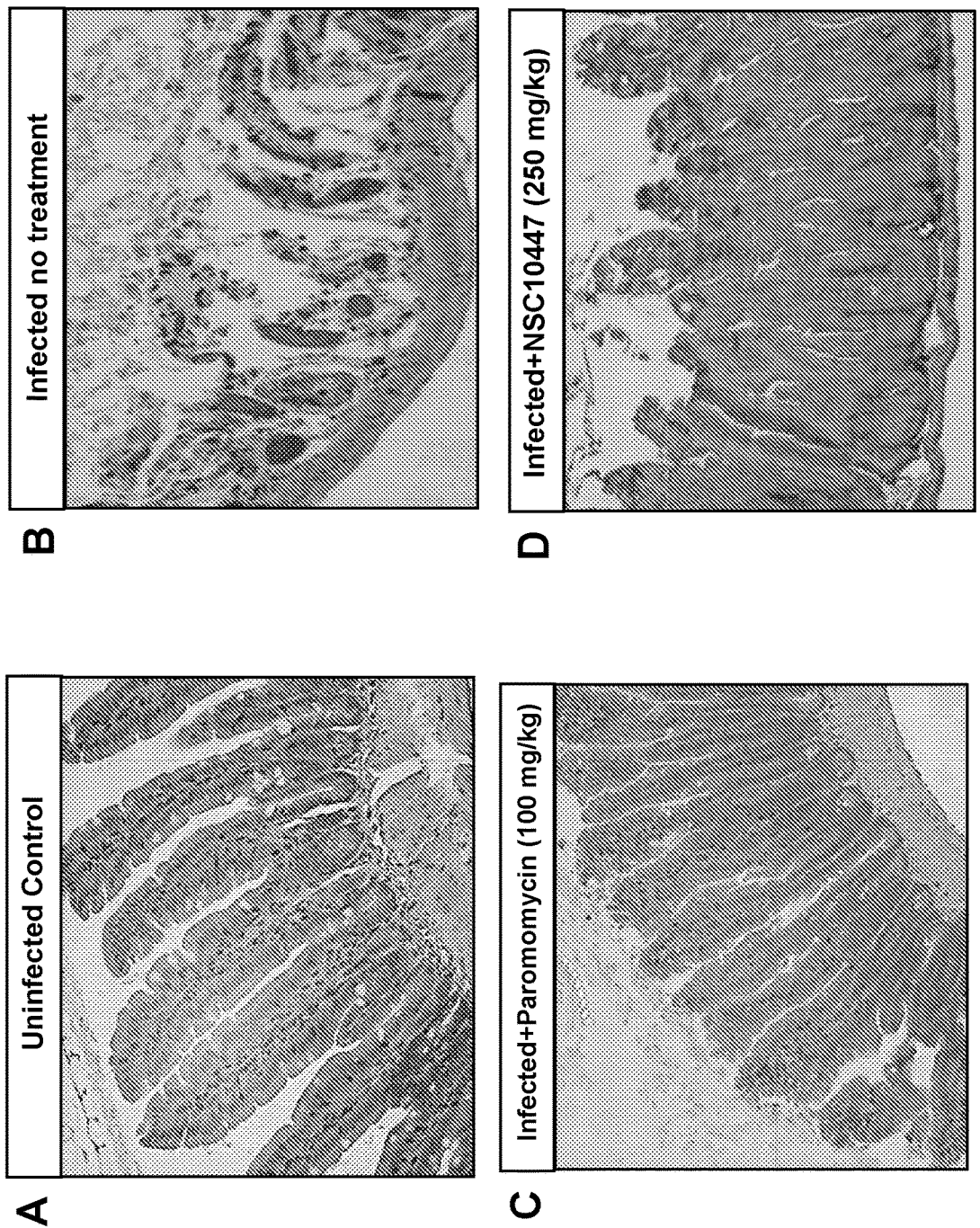
FIG. 8. Histopathological analysis of the effect of *Cryptosporidium parvum* infection in the lower small intestines of mice with or without NSC10447 treatment. Mice infected with *C. parvum* were maintained untreated (Infected no treatment), treated with paromocycin at 100 mg/kg (Infected+Paromomycin (100 mg/kg)) or treated with compound NSC10447 (Infected+NSC10447) at varying doses (250, 500 or 1000 mg/kg) for 8 days. Uninfected mice were maintained as control (Uninfected Control). After 8 days, mice were sacrificed and the lower intestinal tissue processed for histology and stained with hematoxylin and eosin. (A) Uninfected control mice samples depicted intact intestinal epithelium with prominent villi. (B) In contrast, infected mice without treatment depicted denuded villi. Infected mice treated with (C) 100 mg/kg Paromomycin, (D) 250 mg/kg NSC10447, (E) 500 mg/kg NSC10447, and (F) 1000 mg/kg NSC10447 depicted intact intestinal epithelium with prominent villi that were comparable to the uninfected control. The images are representative of samples analyzed from 3 mice per treatment group. (G) The mean percentage of denuded villi in 4 randomly chosen microscopic fields per sample from the uninfected (Uninf), infected untreated (Inf), infected treated with 100 mg/kg paromomycin (Inf+P), infected treated with 250 mg/kg NSC10447 (Inf+250), infected treated with 500 mg/kg NSC10447 (Inf+500), and infected treated with 1000 mg/kg NSC10447 (Inf+1000) mice. The data shown represent means for samples from 3 mice per group with standard error bars and levels of statistical significance depicted (*P<0.05).
Figure 8:
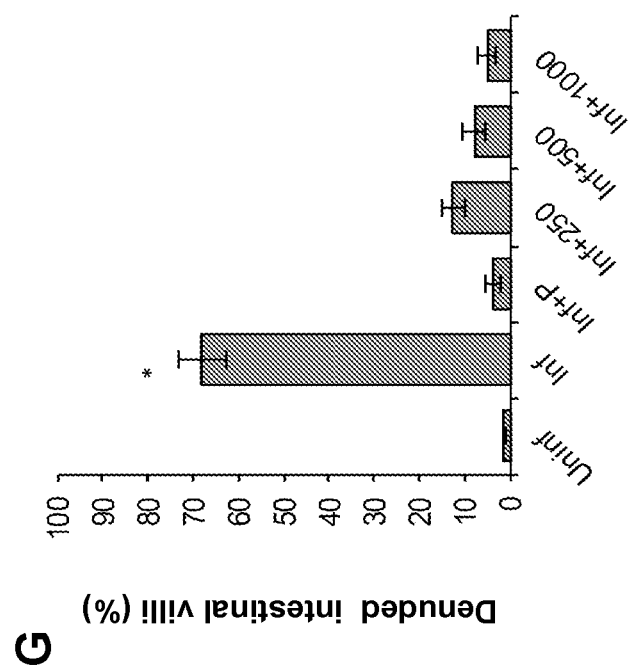
Figure 8:
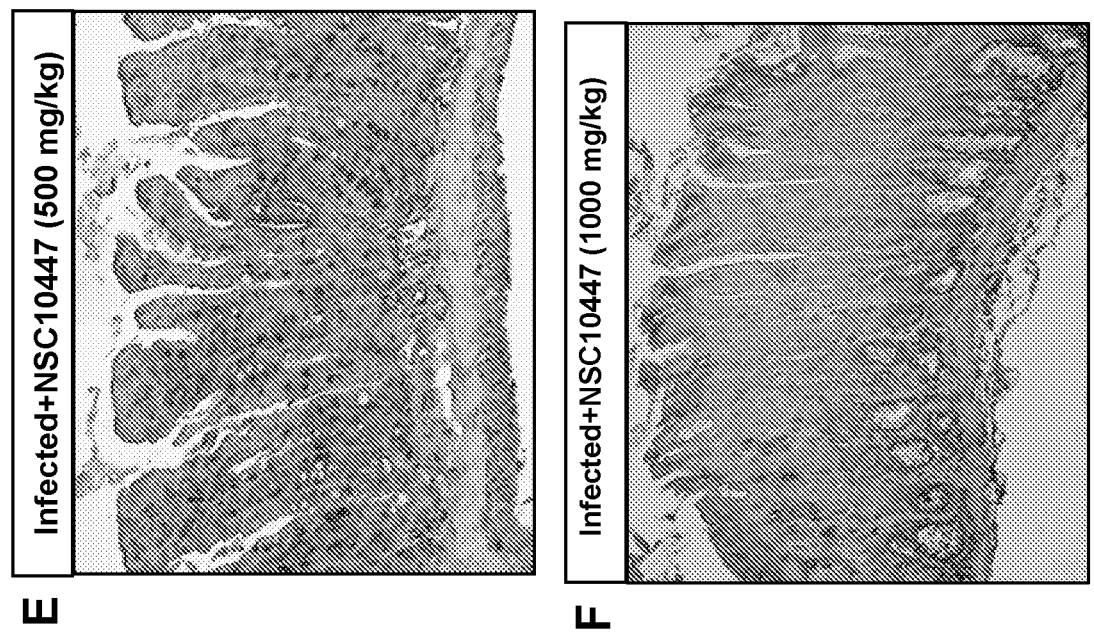

During *C. parvum* infection, usually the distal small intestines are severely affected, characterized by villous atrophy, erosion, and ulceration of the intestinal mucosa. Thus, we performed histopathological examination of the distal small intestines of the experimental mice at 9 days post-infection. As expected, while uninfected mice maintained the integrity of the intestinal mucosa (FIG. 7A and FIG. 8A), infected untreated mice had microscopic lesions characterized by villous atrophy and mucosal erosion (FIG. 7B and FIG. 8B). Infected mice treated with NSC158011 maintained intact intestinal mucosa and villi (FIG. 7D) whose integrity was similar to that of mice treated with paromomycin (FIG. 7C). Likewise, mice treated with NSC10447 also prevented villous atrophy and maintained the integrity of the intestinal mucosa (FIG. 8D-F) similar to treatment with paromomycin (FIG. 8C). We enumerated the mean percentage of denuded intestinal villi in 4 randomly chosen microscopic fields per sample from representative histopathology images. We observed that in infected mice, just like treatment with paromomycin, treatment with NSC158011 and NSC10447 reduced the percentage of denuded intestinal villi by 7-fold or more compared to infected untreated mice (FIG. 7E and FIG. 8G). These findings corroborated the observations that treatment with NSC158011 and NSC10447, just like paromomycin, inhibited *C. parvum* oocysts shedding in mice's feces to almost undetectable levels.

Discussion

Because of the lack of genetic tools for identifying essential molecular components in *Cryptosporidium*, screening for potential drug lead-compounds against *Cryptosporidium* has been based on molecular targets identified in other protozoan parasites such as *Toxoplasma* and *Plasmodium*. However, the completed and annotated *Cryptosporidium* genome sequence shows the absence of conventional drug targets being pursued in other protozoan parasites. Nevertheless, the completed genome sequence of *Cryptosporidium* has unveiled a number of bacterial-like and plant-like classic and novel drug molecular targets that now require functional characterization and validation using genetic tools. Among the identified potential drug molecular targets, is the *C. parvum* lactate dehydrogenase (CpLDH), which is a bacterial-type lactate dehydrogenase enzyme that the parasite uses to generate metabolic energy (ATP) in the glycolytic pathway. Importantly, *C. parvum* lacks both the Krebs cycle and the cytochrome-based respiration chain, suggesting that the glycolysis pathway is the sole energy source in *C. parvum*. Consistently, using morpholino-based targeted knockdown of CpLDH, we recently showed that CpLDH is essential for growth, propagation and viability of *C. parvum* in vitro and in vivo. Corroboratively, previous studies have shown that known inhibitors of lactate dehydrogenase enzymes, gossypol and FX11, are able to inhibit the enzymatic activity of CpLDH. However, both gossypol and FX11 are not specific to CpLDH, but also inhibit mammalian lactate dehydrogenases, implying that they would be toxic to mammalian cells. Regardless, it is noteworthy that CpLDH is unique to *C. parvum*, and is very significantly different from the lactate dehydrogenase enzymes found in mammals.

In the present study, we first established the in vitro enzymatic kinetic parameters of the natively purified recombinant CpLDH protein. Consistent with previous reports by others, we found that recombinant CpLDH preferentially catalyzed the reduction of pyruvate to lactate, and displayed Michaelis-Menten enzymatic kinetics. Using the in vitro enzymatic assay, we identified 29 chemical compounds that inhibited the catalytic activity of recombinant CpLDH for the reduction of pyruvate to lactate. Lactate dehydrogenase is a key enzyme for the anaerobic respiration in which pyruvate is reduced to lactate, with the concomitant oxidation of NADH to NAD$^+$. Thus, we tested the candidate compounds for toxicity in a mammalian cell line (HCT-8) and selected only those that were tolerable at high micromolar concentrations (IC$_{50}$>140 µM) as candidate compounds for further testing. The cytotoxicity IC$_{50}$ values of the candidate compounds were at least 2-fold higher than the cytotoxicity IC$_{50}$ values of known mammalian lactate dehydrogenase inhibitors (gossypol and FX11) in HCT-8 cells. We subsequently tested the candidate compounds for anti-*Cryptosporidium* effect using in vitro infection assays of HCT-8 cells monolayers and identified compounds NSC158011 and NSC10447 that sustainably inhibited the proliferation of intracellular *C. parvum*. The HCT-8 cells were infected with excysted *C. parvum* sporozoites that infect host cells and transform into proliferative merozoites. In *C. parvum* sporozoites and merozoites, CpLDH is expressed and localized in the cytosol, suggesting that it is utilized for energy generation during these parasite stages that are important for host cell invasion and intracellular parasite growth. Interestingly, NSC158011 has been previously shown to inhibit the catalytic activity of the *Plasmodium faclaparum* phosphoethanolamine methyltransferase enzyme, and to inhibit in vitro intracellular growth of the parasite. However, based on the completed genome sequence of *C. parvum*, there are no homologs of genes encoding a phosphoethanolamine methyltransferase in *C. parvum*. Therefore, our findings suggest that the anti-*Cryptopsoridium* activity of NSC158011 is associated with its ability to inhibit the catalytic activity of CpLDH which is an essential enzyme for survival and growth of *C. parvum*, both in vitro and in vivo.

At amino acid sequence level, CpLDH is only 25% identical to human LDH, with the active site conformation of CpLDH being significantly different from that of the human LDH. Further, in the 3-dimensional structure model of the two enzymes, the helix-loop portion of CpLDH is more proximal to the active site loop than it is in the human LDH. Additionally, the co-factor binding site of human LDH possesses a network of hydrogen-bonding formed by a serine residue with NAD$^+$, while the co-factor binding site of CpLDH only forms two hydrogen bonds with NAD$^+$. This is thought to lower the CpLDH affinity for NAD$^+$/NADH than human LDH. When we modeled NSC158011 and NSC10447 onto the 3-D crystal structure of CpLDH and human LDH, we found that both NSC158011 and NSC10447 bind to the NAD+ co-factor binding site. Interestingly, in the docking simulation, NSC10447 displayed better affinity for CpLDH than human LDH, while NSC158011 displayed better affinity for the human LDH. We had selected NSC10447 and NSC158011 based on their low toxicity in a human cell line, but high inhibitory activity against *C. parvum*, though these molecules still bind to the human LDH crystal structure. A docking simulation calculates the free energy of the interaction between a protein and a ligand but does not consider the interaction between the ligand and its surrounding solvent (solvation energy). Due to the unfavorable interaction of high solvent exposure to the non-polar, aromatic rings in NSC158011 docked to human LDH, it can be inferred that the binding stability is greatly reduced. The docking pose of NSC158011 to CpLDH exposes the non-polar regions of the molecule to less solvent, leading to a much more stable interaction. These ligand binding properties suggest that NSC158011 and NSC10447 would more effectively compete out the binding of NAD+ to CpLDH than to human LDH. This is consistent with our observations that both NSC158011 and NSC10447 effectively inhibit *C. parvum* growth and replication (both in vitro and in vivo) at concentrations that are not toxic to mammalian (including human) cells.

Typically, solvent-exposed protein pockets like the one in LDH are often not targeted in lead-cpompound optimization due to their poor binding characteristics, but the results of our in silico docking reveal solvent-exposed protein pockets may be useful for enhancing lead-compound selectivity. Importantly, these differences in ligand-binding stability between CpLDH and human LDH offer prospects for identifying inhibitors that would specifically target CpLDH, without being toxic to mammalian host cells, and would thus be potential lead-compounds for development of effective anti-*Cryptosporidium* drugs.

We observed that NSC158011's $IC_{50}$ for the inhibition of recombinant CpLDH in an in vitro enzymatic assay was higher than its $IC_{50}$ for inhibition of *C. parvum* growth. Based on our observation that NSC158011 binds to the co-factor binding site in CpLDH, the likely reason for this discordance is that in the recombinant CpLDH enzymatic assay in vitro, excessive amounts of NADH co-factor (1 mM) were used that in turn required high concentration of NSC158011 to effectively compete out the co-factor and reduce the generation of the product. In comparison, intracellular (intra-parasite) levels of co-factor are likely much lower (µM range). For instance, in human cells the absolute concentration of NADH has been reported to be in the range of 97 to 168 µM. The lower intracellular concentrations of NADH when compared to the higher in vitro concentrations, would translate into lower concentrations of NSC158011 to effectively compete out the co-factor and register a decrease in CpLDH activity, and subsequent reduction in parasite growth. Importantly, the chemical structure of NSC158011 suggests that it possesses promising drug-like properties that render it amenable to drug development.

Using doses that were tolerable in mice, we tested the in vivo efficacies of NSC158011 and NSC10447 in Gamma interferon knockout mice (B6.129S7-Ifng) that when infected with *C. parvum*, develop debilitating clinical disease, with completion of the parasite life cycle and shedding of oocysts in feces. We found that both NSC158011 and NSC10447 consistently significantly reduced the shedding of *C. parvum* oocysts during the experimental period of 9 days and prevented the occurrence of villous atrophy and intestinal mucosal erosion that is associated with *C. parvum* infection. NSC158011 displayed better efficacy than NSC10447, both in vitro and in vivo, with lower anti-*Cryptosporidium* $IC_{50}$ values. Importantly, compared to the only FDA-approved nitazoxanide that lacks efficacy in immunocompromised individuals, both NCS158011 and NSC10447 were efficacious against *C. parvum* in the immunocompromised mice we used in the study.

In conclusion, we have demonstrated NSC158011 and NSC10477 as specific inhibitors for CpLDH that have efficacy against *C. parvum* both in vitro and in vivo. Thus, our findings provide promising anti-*Cryptosporidium* drug candidates that can be explored further for the development of much needed novel cryptosporidiosis therapeutic interventions.

General Synthetic Methods

The invention also relates to methods of making the compounds and compositions of the invention. The compounds and compositions can be prepared by any of the applicable techniques of organic synthesis, for example, the techniques described herein. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, $5^{th}$ Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compounds of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically, the temperatures will be −100° C. to 200° C., solvents will be aprotic or protic depending on the conditions required, and reaction times will be 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group" refers to any group which, when bound to a hydroxy or other heteroatom prevents undesired reactions from occurring at this group and which can be removed by conventional chemical or enzymatic steps to reestablish the hydroxyl group. The particular removable protecting group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

Suitable hydroxyl protecting groups are known to those skilled in the art and disclosed in more detail in T. W. Greene, *Protecting Groups In Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds described herein can be effective antiparasitic agents and have higher potency and/or reduced toxicity as compared to nitazoxanide. Preferably, compounds of the invention are more potent and less toxic than nitazoxanide, and/or avoid a potential site of catabolic metabolism encountered with nitazoxanide, i.e., have a different metabolic profile than nitazoxanide.

The invention provides therapeutic methods of treating a parasitic infection in a mammal, which involve administering to a mammal having *Cryptosporidium* infection an effective amount of a compound or composition described herein. A mammal includes a primate, human, rodent, canine, feline, bovine, ovine, equine, swine, caprine, bovine and the like. The ability of a compound of the invention to treat an infection may be determined by using assays well known to the art. For example, the design of treatment protocols, toxicity evaluation, data analysis, quantification of tumor cell kill, and the biological significance of the use of transplantable tumor screens are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Materials and Methods

Parasites. For all experiments, the AUCP-1 isolate of *C. parvum* was used. The parasites were maintained and propagated in male Holstein calves in accordance with the guidelines of protocol number 18108 approved by the University of Illinois at Urbana-Champaign, USA. Freshly shed *C. parvum* oocysts in calf feces were extracted and purified by sequential sieve filtration, Sheather's sugar flotation, and discontinuous sucrose density gradient centrifugation, essentially as previously described (J. Parasitol. 1987; 73(2), 314-319. PMID: 3585626). The purified oocysts were rinsed and stored at 4° C. in 50 mM Tris-10 mM EDTA, pH 7.2, and used within 3 months. Sporozoites were excysted from

*C. parvum* oocysts following the method described previously (Antimicrob. Agents Chemother. 2016; 60(1), 570-579). Briefly, to about $1\times10^8$ purified *C. parvum* oocysts suspended in 500 µl of PBS, an equal volume of 40% commercial laundry bleach was added and incubated for 10 minutes at 4° C. The oocysts were washed four times in PBS containing 1% (w/v) bovine serum albumin and resuspended in Hanks balanced salt solution, incubated for 60 minutes at 37° C., and mixed with an equal volume of warm 1.5% sodium taurocholate in Hanks balanced salt solution. The excysted sporozoites were collected by centrifugation and resuspended in supplemented PBS. The sporozoites were purified by passing the suspension through a sterile 5 µM syringe filter (Millex) and enumerated with a hemocytometer.

Biochemical assays. The coding sequence of CpLDH was cloned from cDNA prepared from the AUCP-1 isolate of *C. parvum*, and the His-tagged CpLDH recombinant protein expressed in *Escherichia coli*, and purified in native form essentially as previously described (Int. J. Parasitol. 2017; 47(13), 867-874). Briefly, cDNA was prepared from total RNA extracted from the AUCP-1 isolate of *C. parvum*, and the coding sequencing of CpLDH (Genebank accession number AF274310.1) was PCR-amplified from the cDNA using the primer pair 5'-CTCGAGATGATTGAAA-GACGCAAGA-3' (Forward, with the XhoI restriction site italicized and start codon in bold) and 5'-GGATCCTT ATGCTCCAGCTGGT-3' (Reverse, with the BamHI site italicized and stop codon in bold). The PCR amplicon was cloned at the XhoI/BamHI site of the pET15b expression vector in-frame with the hexahistidine (His-tag) at the N-terminal and sequenced to confirm identity. The recombinant expression vector was transformed into protein expression *E. coli* BL21-CodonPlus-DE3-RIL (Stratagene). Transformed *E. coli* was cultured at 37° C. in Luria broth medium (supplemented with 100 µg/ml ampicillin and 34 µg/ml chloramphenicol) to an $A_{600}$ of 0.8 followed by addition of 1 mM isopropyl-β-d-thiogalactopyranoside to induce protein expression. The expression *E. coli* was harvested and lysed under native conditions by sonicating in lysis buffer (50 mM $NaH_2PO_4$, 300 mM NaCl, 10 mM Imidazole, pH 8.0) containing a 1×EDTA-free protease inhibitor cocktail, 600 units benzonase and 30 kU lysozyme (EMD Millipore). The lysate was clarified by centrifugation and the His-tagged recombinant protein purified under native conditions by nickel-affinity chromatography according to the manufacturer's instructions (Novagen). The wash buffer used contained 50 mM $NaH_2PO_4$, 300 mM NaCl and 20 mM Imidazole, pH 8.0, while the elution buffer was composed of 50 mM $NaH_2PO_4$, 300 mM NaCl, 250 mM Imidazole, pH 8.0. The eluate was dialyzed using a buffer containing 5 mM Hepes-KOH (pH 7.8) and 0.5 mM DTT. The purity of the recombinant protein was determined by SDS/PAGE, and the concentration measured using a Qubit 3.0 fluorometer (Life technologies). The in vitro enzymatic activity of the recombinant CpLDH protein for catalyzing the reduction of pyruvate to lactate was determined by measuring the change in optical density of a 100 µl reaction mixture containing 10 mM pyruvate, 1 mM NADH, 100 mM Tris, pH 7.5 and varying concentrations of CpLDH recombinant protein at 25° C. On the other hand, the catalytic activity of CpLDH recombinant protein for the oxidation of lactate to pyruvate was determined by measuring the change in optical density of a 100 µl reaction mixture containing 100 mM lactate, 1 mM $NAD^+$, 100 mM Tris, pH 9.2, with varying concentrations of CpLDH recombinant protein at 25° C. For determining the kinetic parameters, a fixed concentration of CpLDH recombinant protein was used in reactions with varying substrate and co-factor concentrations (pyruvate from 0.5-15 mM; NADH from 0.25-1.5 mM for the reduction reaction, while for the oxidation reaction lactate varied from 25-125 mM; $NAD^+$ from 0.05-1.5 mM). In all assays, reaction mixtures without recombinant CpLDH protein were included as negative controls. All assays were performed in triplicate and repeated at least thrice. The change in optical density was measured every 15 seconds for a total of 2 minutes using a Spectra Max 384 Plus plate reader (Molecular Devices) at a wavelength of 340 nm.

Screening compounds for inhibitory activity against CpLDH. The chemical compounds were obtained from the National Cancer Institute/Developmental Therapeutics Program Open Chemical Repository. They consisted of a diverse set of compounds (n=27) reported previously (Int J Parasitol Drugs Drug Resist. 2016; 6(1), 44-53), and a Mechanistic Set IV compounds (n=800). The compounds were reconstituted in dimethyl sulfoxide (DMSO) as stock solutions. Just before use, aliquots of the stock solutions were diluted in sterile distilled water to generate working solutions, such that the final amount of DMSO added to the reaction mixtures was less than 1% (V/V). The compounds were tested for their inhibitory effect against the enzymatic activity of recombinant His-tagged CpLDH for catalyzing the reduction of pyruvate to lactate. The reactions were performed in 100 µl reaction volume containing 10 mM pyruvate, 1 mM NADH, 100 mM Tris, pH 7.5, 15 ng/µl of recombinant CpLDH protein with or without 20 µM of compound. Control reactions without recombinant CpLDH protein were included. Reactions were performed in triplicate and repeated at least thrice. The change in optical density was measured every 15 seconds for a total of 2 minutes using a Spectra Max 384 Plus plate reader (Molecular Devices) at a wavelength of 340 nm. The mean percent inhibition effect of each compound on recombinant CpLDH activity was derived using the following formula:

$$\text{Mean Percent Inhibition } (MPI) = (\Delta OD_{340} \text{ of reaction with compound}/\Delta OD_{340} \text{ of reaction without compound}) \times 100$$

where:

$\Delta OD_{340}$ is the mean change in optical density for triplicate reactions after 2 minutes.

MPI values greater and less than 0 indicate inhibition and augmentation of CpLDH activity, respectively.

MPI value of 0 is for the reaction without compound, but with an equivalent volume of solvent used to reconstitute compound.

Compound cytotoxicity assay. Compounds with inhibitory effect against the enzymatic activity of recombinant CpLDH were tested for cytotoxicity in a human cell line, HCT-8 (American Type Culture Collection Item number: CCL244), that was used for in vitro culture of *C. parvum*. A colorimetric assay using the cell proliferation reagent WST-1 (Roche, USA) for the quantification of cell viability was performed. HCT-8 cells were cultured in 96-well plates in 200 µl of RPMI 1640 medium without phenol red (Life Technologies), but supplemented with 2 g/L of sodium bicarbonate, 2.5 g/L of glucose, 10% FBS (Gibco, USA), 1× antibiotic-antimycotic (Gibco), and 1× sodium pyruvate (Gibco). When the cells were confluent, the old medium was replaced with fresh medium with or without varying concentrations of chemical compound. After 24 h of culture, 10 µl of the cell proliferation reagent WST-1, (for quantification of cell viability) was added to each well, mixed and the plates incubated for 1 h at 37 C with 5% $CO_2$ in the dark. Following incubation, 150 µL of the medium from each well was transferred to a new 96-well plate and quantification of the formazan dye produced by metabolically active cells was read as absorbance at a wavelength of 420 nm using a scanning multi-well spectrophotometer (Spectra Max 384 Plus; Molecular Devices, USA). Three independent assays were performed and the dose-response curves of the means of triplicate assays were generated using GraphPad PRISM software to derive the half maximal inhibitory concentration ($IC_{50}$) of compounds in HCT-8 cells (Table 7).

TABLE 7

Cytotoxicity $IC_{50}$ values in HCT-8 cells for inhibitors of CpLDH.

| COMPOUND | CYTOTOXICITY $IC_{50}$ (µM) | COMPOUND | CYTOTOXICITY $IC_{50}$ (µM) |
|---|---|---|---|
| NSC51148 | 39.65 | NSC638634 | 156.56 |
| NSC1771 | 110.11 | NSC56817 | 64.18 |
| NSC626433 | 265.03 | NSC79688 | 144.60 |
| NSC349438 | 93.90 | NSC18298 | 81.87 |
| NSC10447 | 290.28 | NSC115538 | 158.01 |
| NSC85561 | 103.29 | NSC71948 | 105.72 |
| NSC73413 | 219.80 | NSC22842 | 83.55 |
| NSC657799 | 113.90 | NSC175296 | 156.15 |
| NSC686349 | 282.94 | NSC33006 | 87.34 |
| NSC638352 | 116.49 | NSC80396 | 91.92 |
| NSC34931 | 71.08 | NSC82116 | 117.98 |
| NSC253995 | 83.05 | NSC158011 | 148.53 |
| NSC70925 | 141.90 | NSC22225 | 96.82 |
| NSC70929 | 180.85 | NSC37031 | 332.98 |
| NSC36354 | 81.80 | | |

In vitro testing of the anti-*Cryptosporidium* effect of CpLDH inhibitors. HCT-8 cells were cultured in supplemented RPMI-1640 medium in 96-well plates. When the cells were confluent, old medium was replaced with fresh medium. To one set of wells, varying concentrations of recombinant CpLDH inhibitors (reconstituted in DMSO and diluted in RPMI medium) were added, while another set was left without inhibitors. Paromomycin was used as a positive control drug reconstituted in distilled sterile water. Then, $4 \times 10^4$ freshly excysted sporozoites were added to each well and incubated at 37° C. with 5% $CO_2$. After 2 h incubation, varying concentrations of CpLDH inhibitors were added to the set of infected cells that were not treated initially. Control infected cells without inhibitors, but with added DMSO volumes equivalent to those used in the wells with inhibitors, were included. The cells were maintained in culture for a total of either 48 h or 72 h and processed for immunofluorescence assay as previously described (Int. J. Parasitol. 2017; 47(13), 867-874). Briefly, medium was decanted, and the cells fixed with methanol-acetic acid (9:1) for 2 minutes at room temperature. The cells were rehydrated and permeabilized by two successive washes with buffer (0.1% Triton X-100, 0.35 M NaCl, 0.13 M Tris-base, pH 7.6) and blocked with 5% normal goat serum, followed by staining with antibody to *C. parvum* (SporoGlo; Waterborn, Inc.) overnight at 4° C. The stained cells were washed twice with PBS, followed by water, and then imaged with an inverted fluorescence microscope. Fluorescence quantification was done using ImageJ version 1.37v software (NIH). Assays were performed in triplicate and repeated at least thrice.

In silico modeling of NSC158011 and NSC10447 binding to CpLDH and Human LDH. To propose a model for the specific binding of NSC15801 and NSC10447 to lactate dehydrogenase, the crystal structure of CpLDH complexed with substrate pyruvate and cofactor analogue 3-acetylpyridine adenine dinucleotide (APAD) was obtained from the RCSB protein database (4ND2). The chemical structures of NSC158011 and NSC10447 were obtained from the PubChem library. The protein crystal structure was loaded into the AutoDockTools software suite and a search location box was drawn encompassing the co-factor analogue APAD in one subunit of the homotetrameric protein. APAD was removed from the active site of the crystal structure using the Swiss-Model DeepView software. Using Autodock Vina (Scipps Institute, USA), polar hydrogen atoms were added to the APAD-deficient LDH structure and its non-polar hydrogen atoms were merged. NSC15801 and NSC10447 were each docked into the empty co-factor binding site of one subunit of the protein with exhaustiveness=10. Both compounds were docked using a 40×40×40 Å grid box, and all single bonds within the ligands were set to allow free rotation. The procedure was subsequently repeated with the crystal structure of human LDH (1I0Z) and a 24×14×20 Å grid box around the co-factor binding pocket of the new structure. Docking results were visualized using VIVID (University of Illinois at Urbana-Champaign, USA). The most energetically favorable result of each docking was then loaded as a protein-ligand complex into the Schrödinger Maestro software (Schrodinger LLC, USA) to investigate the nature of the protein-ligand interactions and propose a mechanism for the lead compounds' inhibition of LDH. Because the presence or absence of natural LDH substrate, pyruvate, complexed within the active site did not significantly affect binding of the compounds in CpLDH or human LDH, those models were excluded in the final molecular docking simulations.

In vivo testing of the anti-*Cryptosporidium* effect of CpLDH inhibitors. Gamma interferon knockout mice (B6.12957-Ifng), 8 weeks of age, were purchased from Charles River, USA. The care and use of the mice was done following the guidelines of protocol number 17024 approved by the University of Illinois at Urbana-Champaign, USA. The animals were allowed to acclimatize for 1 week before experiments commenced. Stock solutions of recombinant CpLDH inhibitors reconstituted in DMSO were diluted in sterile distilled water to reduce the final amount of DMSO in the solution to less than 1% (v/v) before administering them to mice. Prior to testing the anti-*Cryptosporidium* effect of the inhibitors in mice, the tolerability of each inhibitor was tested by oral gavage using varying dosages (100-2000 mg/kg body weight) of each inhibitor in groups of mice (three mice for each dose) daily for 7 days.

Mice were observed daily for signs of toxicity including changes from normal physical activity, respiration, body temperature, feeding, posture, fur condition or occurrence of death. The highest dose (1000 mg/kg for NSC10447, and 400 mg/kg for NSC158011) of each inhibitor that did not induce any toxicity signs over the 7 days of administration was used as the maximum dose limit for subsequent in vivo experiments. The subsequent dosages of NSC10447 used in the mice infection assays were 250, 500 and 1000 mg/kg mouse body weight, while the NSC158011 dosages used were 100, 200 and 400 mg/kg mouse body weight. Mice were allocated to groups as follows: "Infected plus inhibitor treatment"; "Infected minus inhibitor treatment"; "Uninfected minus inhibitor treatment" and "Infected plus paromomycin treatment". Each group contained at least three mice. Each mouse in the infection groups received 5,000 *C. parvum* oocysts (resuspended in 50 μl of PBS) by oral gavage. Mice were housed individually in cages lined with sterile gauze as bedding. One day post-infection (PI), daily oral gavage administration of recombinant CpLDH inhibitor or paromomycin commenced and continued for a total of 7 days. Untreated mice received an equivalent volume of sterile distilled water (containing DMSO equivalent to the amount administered in the inhibitor-treated group) by oral gavage. Fecal pellets were collected daily from each cage and placed in individual sterile 15 ml conical tubes. An equivalent volume of PBS containing a cocktail of penicillin (100 units/ml), streptomycin (100 μg/ml), chloramphenicol (34 μg/ml) and amphotericin (0.25 μg/ml) was added to the fecal samples and stored at 4° C. until use for quantification of *C. parvum* genomic DNA load. Three independent replicate infection assays were performed. At 9 days PI, mice were euthanized and 5 cm of the distal small intestine resected 2 cm anterior to the cecum and immediately submerged in 4% buffered formalin. The intestinal tissues were submitted for histopathology to the Veterinary Diagnostic Laboratory at the University of Illinois at Urbana-Champaign. Briefly, intestinal tissues preserved in 4% buffered formalin were washed in 70% ethanol and embedded in 1% agar and then processed for paraffin embedding. For hematoxylin and eosin staining, five μm transverse and cross sections were cut and processed and stained following standard procedures of the Veterinary Diagnostic Laboratory. Sections were imaged using a Zeiss microscope and images captured with a color camera.

Quantification of *C. parvum* shed in mice feces. Genomic DNA was extracted from individual fecal samples collected from mice at different days as described above. For each sample, 220 mg of homogenized feces were used to extract genomic DNA using the QIAamp PowerFecal DNA Kit (Qiagen, USA) following the manufacturer's instructions. Quantification of the amount of *C. parvum* 18s rRNA gene (GenBank accession number AF164102) was performed essentially as described previously (Int. J. Parasitol. 2018; 48(8), 649-656). Briefly, the primer pair 5'-CTGCGAATGGCTCATTATAACA-3' (Forward), and 5'-AGGCCAATACCCTACCGTCT-3' (Reverse) was used to generate a 240 bp amplicon from *C. parvum* genomic DNA by conventional PCR. The PCR product was fractionated on agarose gel, extracted using the QIAquick® Gel extraction kit (Qiagen, USA), and the concentration measured by Nanodrop Spectrophotometer (Fisher, USA). Ten-fold serial dilutions of the extracted DNA fragment were made and used as quantification standards for real-time PCR. Each real time PCR mixture contained 2 μl of DNA template, 1 μl of primer mix (500 nM each), and 10 μl of SsoAdvanced Universal SYBR Green Supermix (Bio-Rad, USA), with the final volume made up to 20 μl with nuclease-free water. The cycling conditions included an initial denaturation for 10 min at 98° C., 40 cycles at 98° C. for 15 s and 60° C. for 1 min, and a final melting curve step. Cycling was performed using a 7500 Real Time PCR System (Applied Biosystems, USA). DNA quantities were derived by the system software using the generated quantification standard curves.

Statistical analyses. Statistical analyses were performed using two-tailed Student's t test. P values of 0.05 or less were considered significant.

Example 2. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

|  | mg/tablet |
|---|---|
| (i) Tablet 1 |  |
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
|  | 300.0 |
| (ii) Tablet 2 |  |
| 'Compound X' | 20.0 |
| Microcrystalline cellulose | 410.0 |
| Starch | 50.0 |
| Sodium starch glycolate | 15.0 |
| Magnesium stearate | 5.0 |
|  | 500.0 |
| (iii) Capsule | mg/capsule |
| 'Compound X' | 10.0 |
| Colloidal silicon dioxide | 1.5 |
| Lactose | 465.5 |
| Pregelatinized starch | 120.0 |
| Magnesium stearate | 3.0 |
|  | 600.0 |
|  | mg/mL |
| (iv) Injection 1 (1 mg/mL) |  |
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |
| (v) Injection 2 (10 mg/mL) |  |
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| -continued | |
|---|---|
| (vi) Aerosol | mg/can |
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| | wt. % |
|---|---|
| (vii) Topical Gel 1 | |
| 'Compound X' | 5% |
| Carbomer 934 | 1.25% |
| Triethanolamine | q.s. |
| (pH adjustment to 5-7) | |
| Methyl paraben | 0.2% |
| Purified water | q.s. to 100 g |
| (viii) Topical Gel 2 | |
| 'Compound X' | 5% |
| Methylcellulose | 2% |
| Methyl paraben | 0.2% |
| Propyl paraben | 0.02% |
| Purified water | q.s. to 100 g |
| (ix) Topical Ointment | |
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |
| (x) Topical Cream 1 | |
| 'Compound X' | 5% |
| White bees wax | 10% |
| Liquid paraffin | 30% |
| Benzyl alcohol | 5% |
| Purified water | q.s. to 100 g |
| (xi) Topical Cream 2 | |
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method for treating a parasitic infection comprising administering to a subject in need thereof a therapeutically effective amount of a compound of Formula I or Formula II:

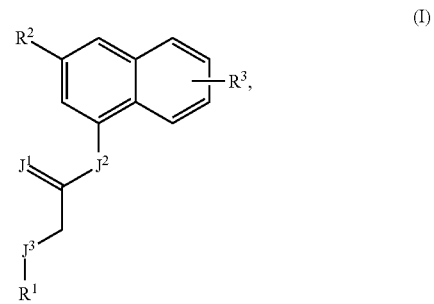

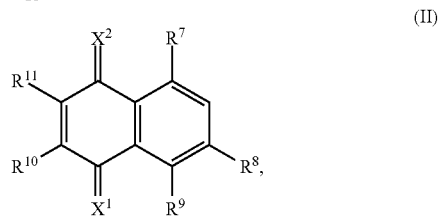

or a salt thereof;
wherein
$J^1$ and $J^3$ are each independently S, O, or $NR^Z$ wherein $R^Z$ is H, —$(C_1$-$C_6)$alkyl, or $(C_3$-$C_6)$ cycloalkyl;
$J^2$ is $NR^Z$, S, O;
$X^1$ and $X^2$ are independently O or S;
$R^1$ is aryl,

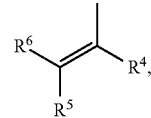

heterocycloalkyl, or heteroaryl;
$R^2$ is H, halo, OH, SH, $NR^A R^B$, —$C(=O)OR^C$, —$S(=O)_2 NR^C R^D$, —$(C_1$-$C_6)$alkyl, —$O(C_1$-$C_6)$alkyl, —$S(C_1$-$C_6)$alkyl, —$(C_3$-$C_6)$ cycloalkyl, —$O(C_3$-$C_6)$ cycloalkyl, —$S(C_3$-$C_6)$ cycloalkyl, heterocycloalkyl, aryl, or heteroaryl, wherein aryl or heteroaryl is unsubstituted or substituted;
$R^3$ is H, halo, or OH;
$R^4$ and $R^5$ are independently halo, OH, SH, $NR^A R^B$, —$C(=O)OR^C$, or —$S(=O)_2 NR^C R^D$;
$R^6$ is H, —$(C_1$-$C_6)$alkyl, or —$(C_3$-$C_6)$ cycloalkyl;
$R^7$, $R^8$ and $R^9$ are independently OH, halo, SH, $NR^A R^B$, —$C(=O)OR^C$, or —$S(=O)_2 NR^C R^D$;
$R^{10}$ and $R^{11}$ are independently halo, OH, SH, $NR^A R^B$, —$C(=O)OR^C$, —$S(=O)_2 NR^C R^D$; and
$R^A$, $R^B$, $R^C$, and $R^D$ are each independently H, —$(C_1$-$C_6)$alkyl, or —$(C_3$-$C_6)$ cycloalkyl;
thereby killing or inhibiting the growth of parasites in the subject;

wherein the parasite of the parasitic infection is *Cryptosporidium parvum*.

2. The method of claim 1 wherein the compound of Formula I is NSC158011:

(NSC158011)

3. The method of claim 1 wherein the compound is represented by Formula I parasite of the parasitic infection is *Cryptosporidium parvum*.

4. The method of claim 1 wherein the subject is infected with *C. parvum* and is shedding *C. parvum* oocysts wherein treatment reduces the shedding of oocysts to undetectable levels as quantified by real-time polymerase chain reaction.

5. The method of claim 1 wherein the subject is malnourished, immunocompromised, or a combination thereof.

6. The method of claim 1 wherein the compound selectively inhibits a lactate dehydrogenase (LDH) enzyme endogenous to the parasite and in the presence of an LDH enzyme endogenous to the subject infected with the parasite.

7. The method of claim 6 wherein the compound selectively binds to the co-factor binding site of the LDH enzyme endogenous to the parasite.

8. The method of claim 1 wherein the therapeutically effective amount of the compound is an oral dose of about 100 mg/kg to about 2000 mg/kg per day for one or more days.

9. The method of claim 1 wherein treated subject has intact intestinal epithelium with prominent villi comparable to an uninfected control subject.

10. The method of claim 1 wherein the compound of Formula I is:

11. A compound of Formula IB:

(I)

or a salt thereof;
wherein
$J^1$, $J^2$, and $J^3$ are each independently O, S, or $NR^Z$ wherein $R^Z$ is H, —($C_1$-$C_6$)alkyl, or —($C_3$-$C_6$)cycloalkyl;
$R^1$ is $R^2$ is H, halo, OH, SH, $NR^AR^B$, —C(=O)$OR^C$, —S(=O)$_2NR^CR^D$, —($C_1$-$C_6$)alkyl, —O($C_1$-$C_6$)alkyl, —S($C_1$-$C_6$)alkyl, —($C_3$-$C_6$)cycloalkyl, —O($C_3$-$C_6$)cycloalkyl, —S($C_3$-$C_6$)cycloalkyl, heterocycloalkyl, aryl, or heteroaryl, wherein aryl or heteroaryl is unsubstituted or substituted;
$R^3$ is H, halo, or OH;
$R^4$ and $R^5$ are independently halo, OH, SH, $NR^AR^B$, —C(=O)$OR^C$, or —S(=O)$_2NR^CR^D$;
$R^6$ is H, —($C_1$-$C_6$)alkyl, or —($C_3$-$C_6$)cycloalkyl; and $R^A$, $R^B$, $R^C$, and $R^D$ are each independently H, —($C_1$-$C_6$)alkyl, or —($C_3$-$C_6$)cycloalkyl.

12. The compound of claim 11 wherein $R^1$ of Formula I is 1,2-dichloroethen-1-yl, 1,2-dibromoethen-1-yl, 1,2-difluoroethen-1-yl, 1,2-dihydroxyethen-1-yl, 1,2-diaminoethen-1-yl, 1-chloro-2-hydroxyethen-1-yl, 1-hydroxy-2-chloroethen-1-yl, 1-hydroxy-2-aminoethen-1-yl, 1-amino-2-hydroxyethen-1-yl, 1-amino-2-chloroethen-1-yl, 1-chloro-2-aminoethen-1-yl, 1-bromo-2-aminoethen-1-yl, 1-bromo-2-hydroxyethen-1-yl, 1-bromo-2-aminoethen-1-yl, 1-bromo-2-chloroethen-1-yl, 1-hydroxy-2-bromoethen-1- yl, 1-amino-2-bromoethen-1-yl, 1-chloro-2-bromoethen-1-yl, 1-chloro-2-fluoroethen-1-yl, 1-amino-2-fluoroethen-1-yl, 1-hydroxy-2-fluoroethen-1-yl, or 1-bromo-2-fluoroethen-1-yl.

13. The compound of claim 11 wherein the compound of Formula I is a compound of Formula IB:

(IB)

or a salt thereof;
wherein
  $J^1$ is O or S;
  $J^2$ is O or NH;
  $J^3$ is S or NH; and
  $R^4$ and $R^5$ are independently fluoro, chloro, bromo, OH, or $NH_2$.

14. The compound of claim 11 wherein the compound is:

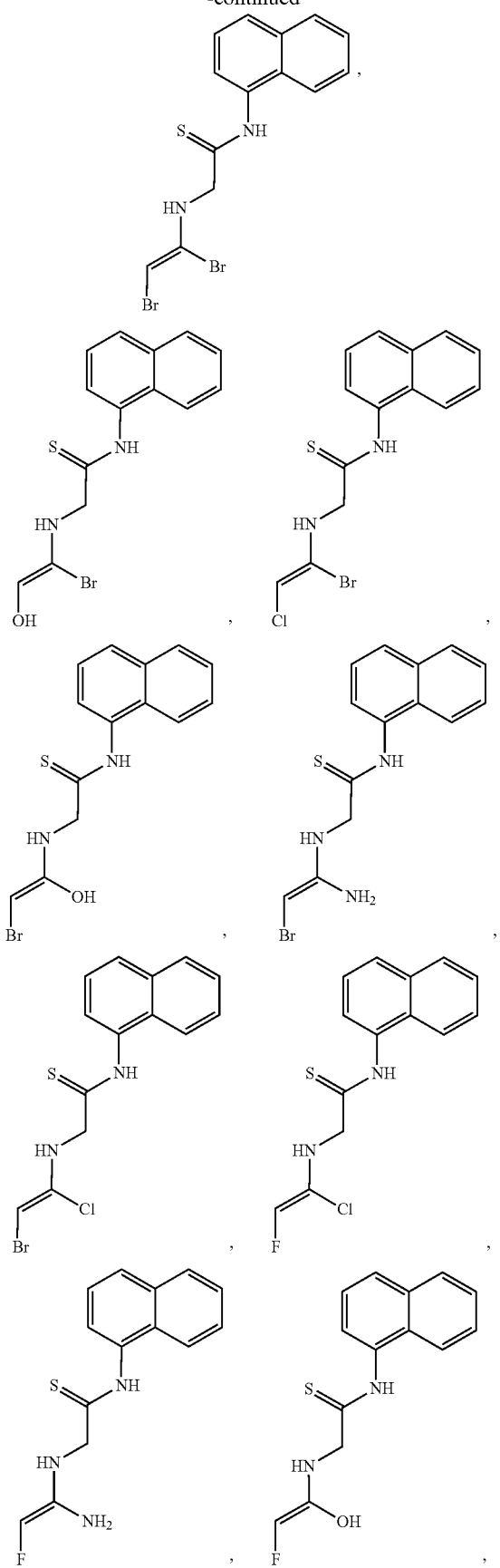
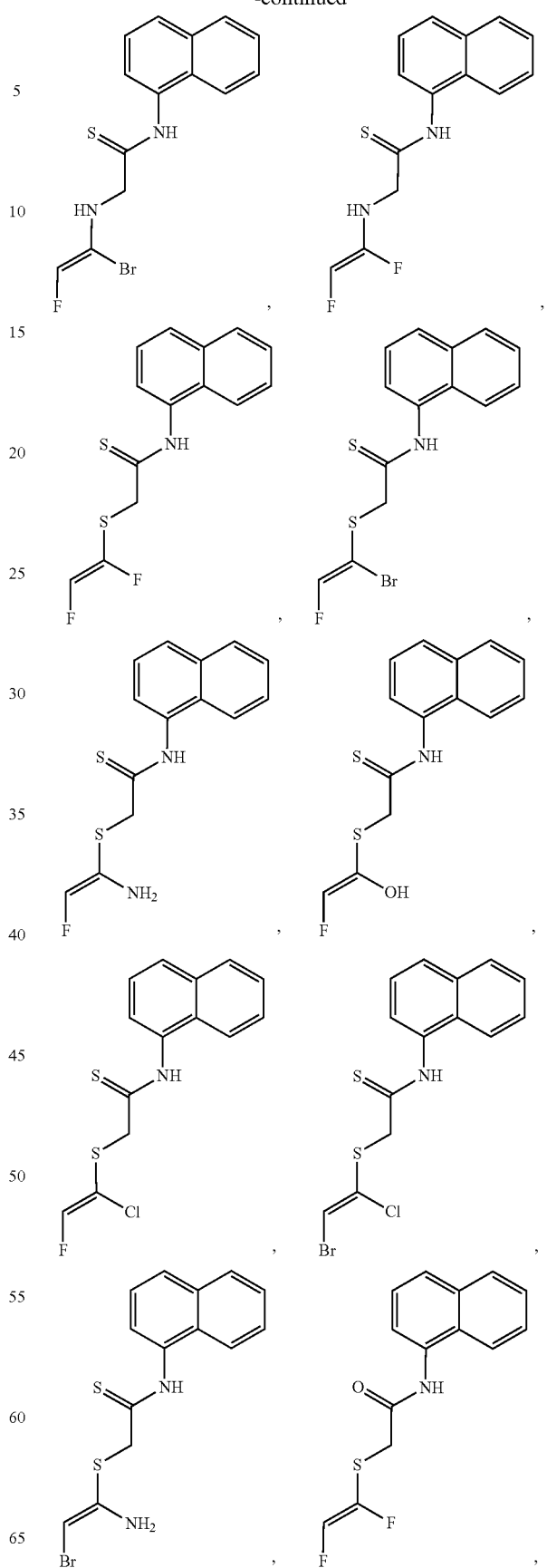

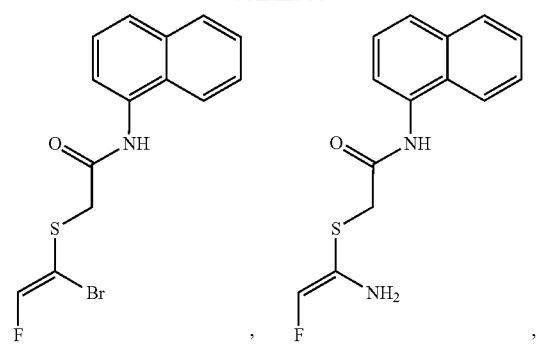
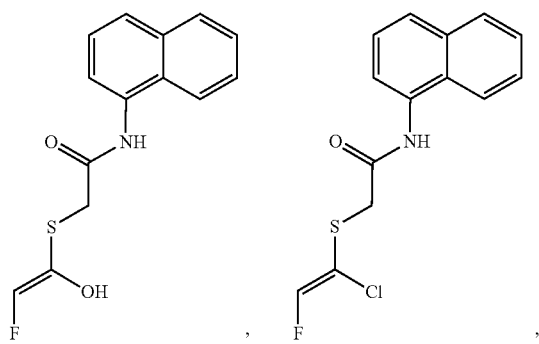
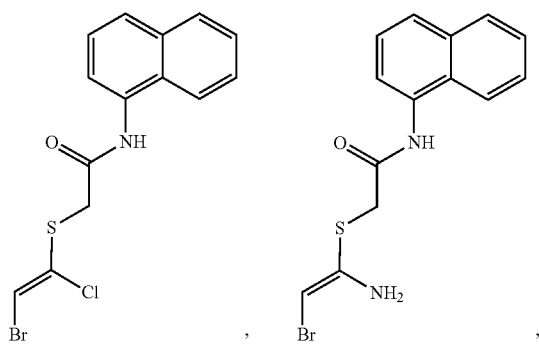
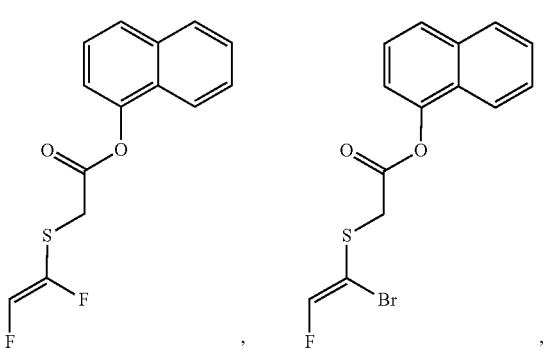
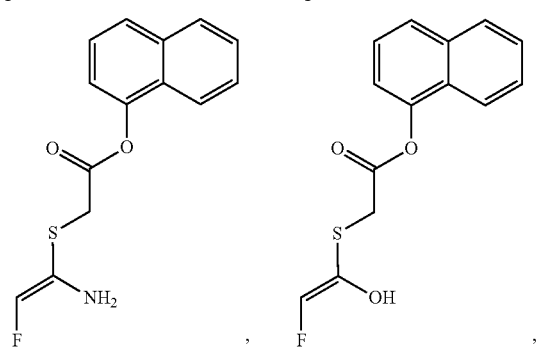
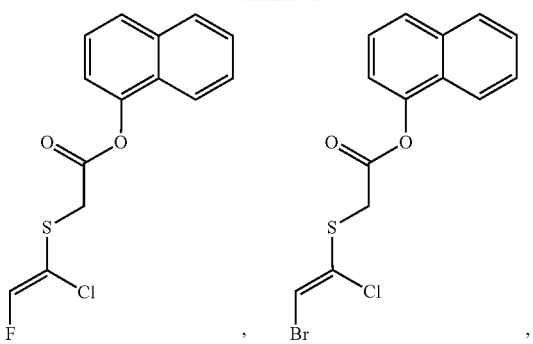
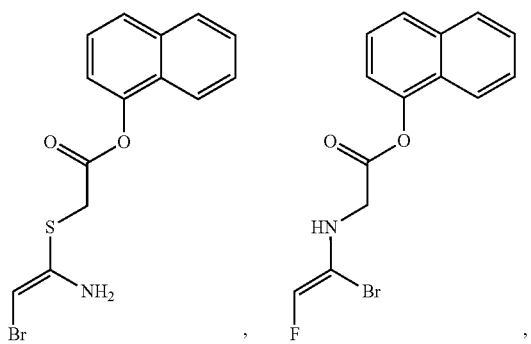
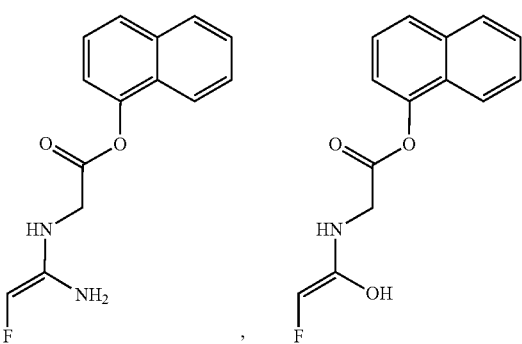
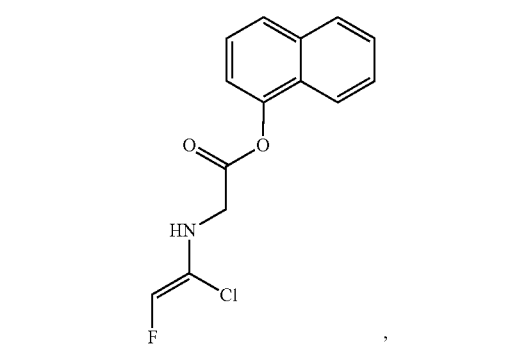
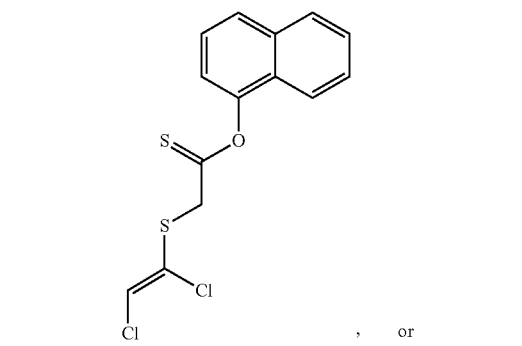, or -continued

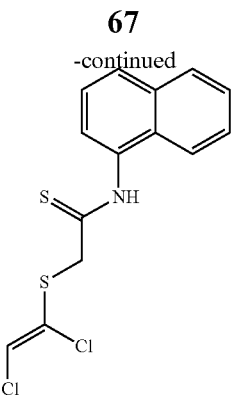

15. A compound of Formula II:

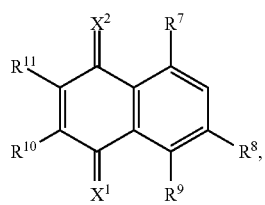

(II)

or a salt thereof;
wherein
  $X^1$ and $X^2$ are independently O or S;
  $R^7$, $R^8$ and $R^9$ are independently $NR^A R^B$, —C(=O)OR$^C$, or —S(=O)$_2$NR$^C$R$^D$;
  $R^{10}$ and $R^{11}$ are independently halo, OH, SH, NR$^A$R$^B$, —C(=O)OR$^C$, —S(=O)$_2$NR$^C$R$^D$;
  and
  $R^A$, $R^B$, $R^C$, and $R^D$ are each independently H, —(C$_1$-C$_6$)alkyl, or —(C$_3$-C$_6$)cycloalkyl.

16. The compound of claim 15 wherein $R^{10}$, and $R^{11}$ are independently halo, OH, or NH$_2$.

17. The compound of claim 15 wherein the compound is:

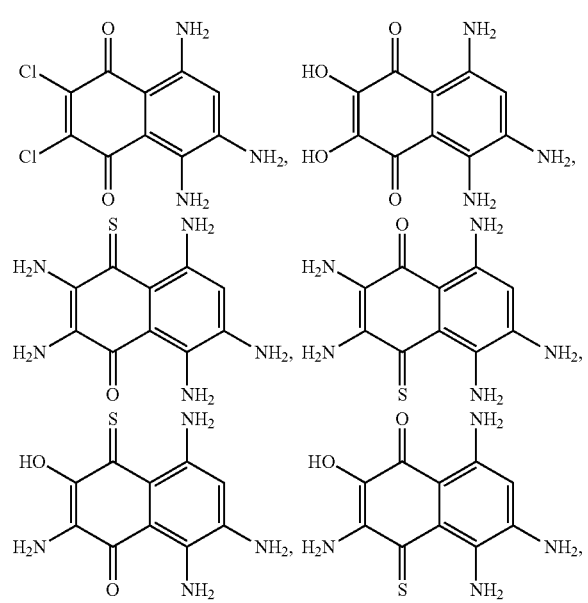

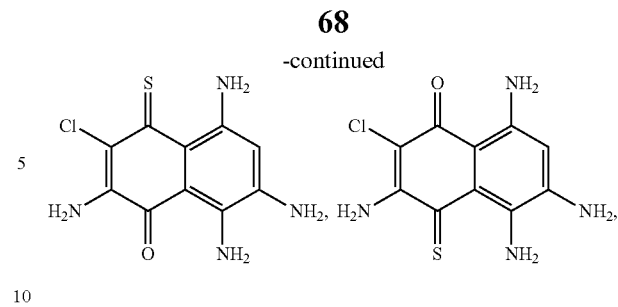

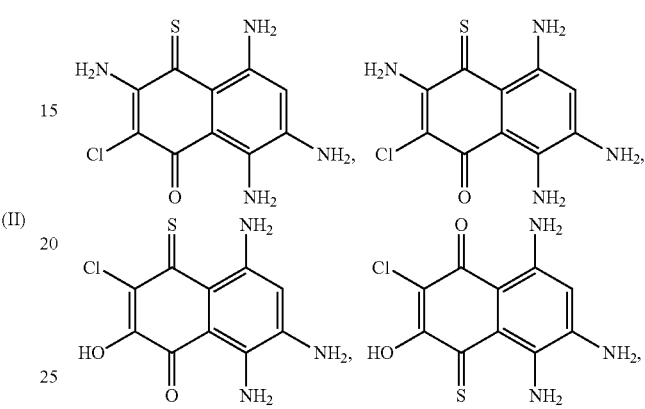

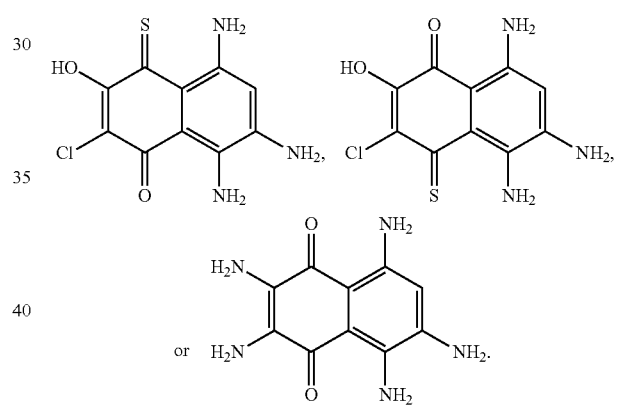

18. A pharmaceutical composition comprising a compound of claim 11 in combination with a pharmaceutically acceptable diluent, or carrier.

19. The compound of claim 15 wherein the compound is:

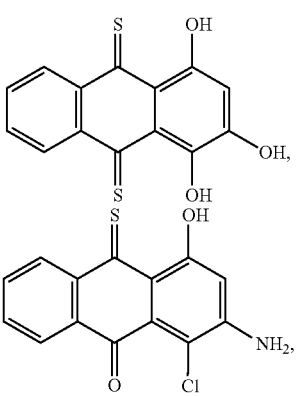

-continued
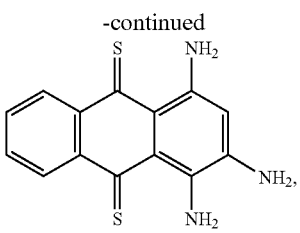
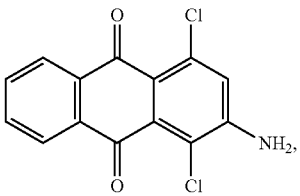
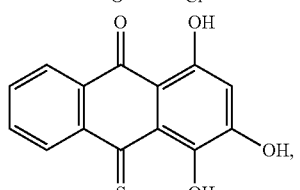
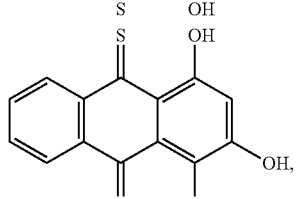
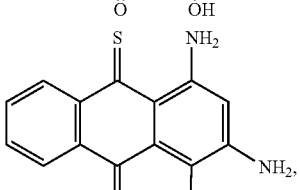
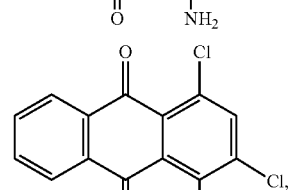
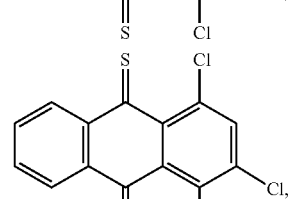
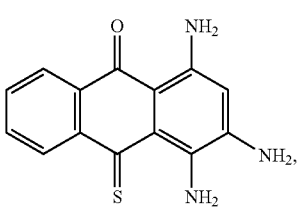
-continued
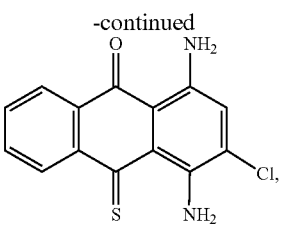
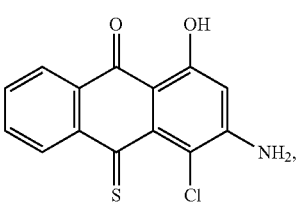
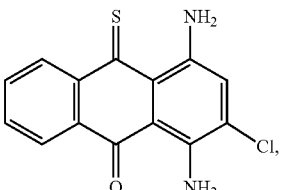
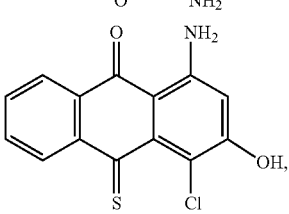
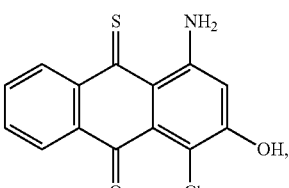
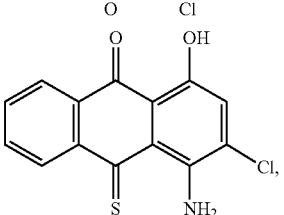
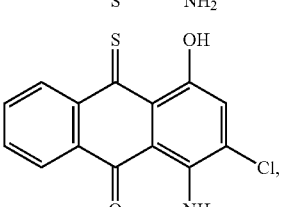
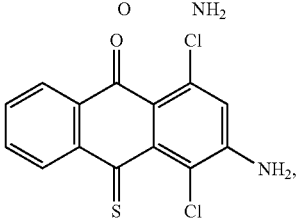

-continued
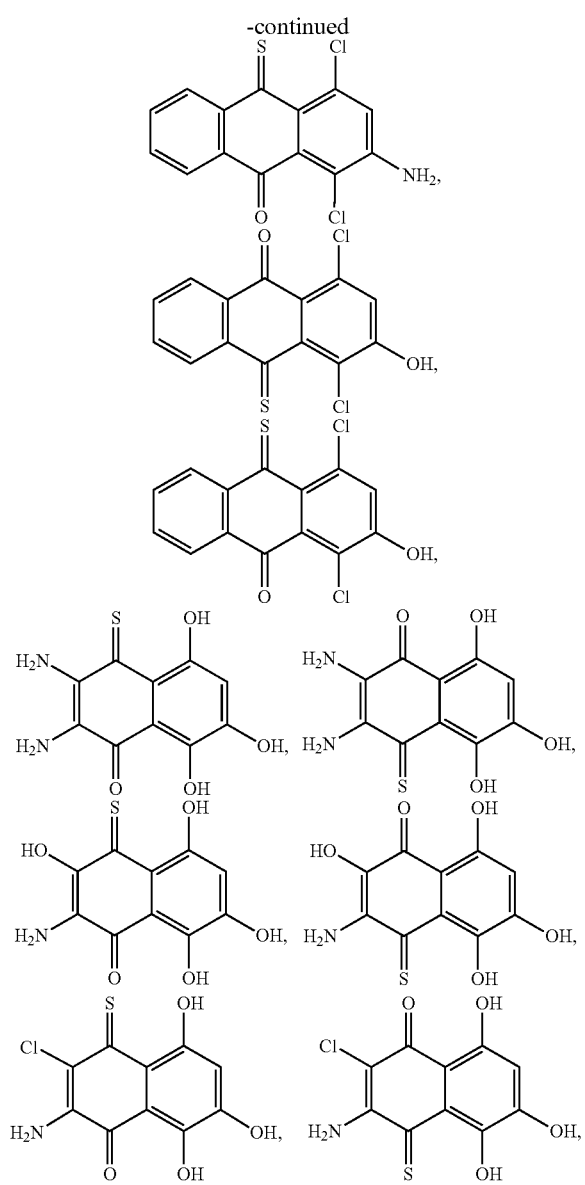
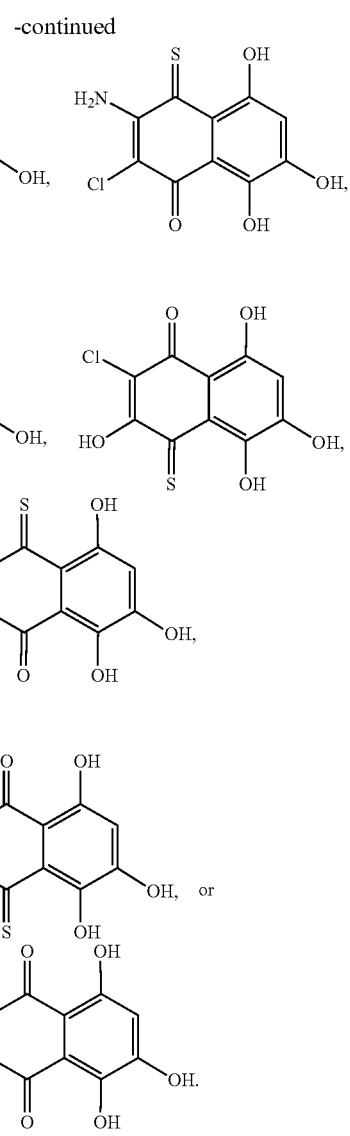
* * * * *